(12) United States Patent
Shluzas et al.

(10) Patent No.: US 10,926,038 B2
(45) Date of Patent: Feb. 23, 2021

(54) SYSTEM AND METHOD FOR SAFETY SYRINGE

(71) Applicant: Credence MedSystems, Inc., Menlo Park, CA (US)

(72) Inventors: Alan E. Shluzas, San Carlos, CA (US); Stephen H. Diaz, Palo Alto, CA (US); John F. Shanley, Emerald Hills, CA (US); Jeff Tillack, Foster City, CA (US); Dan Thayer, Trustin, CA (US); Gary Steese-Bradley, San Jose, CA (US); Mina M. Leung, Mountain View, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 541 days.

(21) Appl. No.: 15/801,239

(22) Filed: Nov. 1, 2017

(65) Prior Publication Data
US 2018/0161518 A1    Jun. 14, 2018

Related U.S. Application Data

(60) Provisional application No. 62/542,230, filed on Aug. 7, 2017, provisional application No. 62/480,276, filed
(Continued)

(51) Int. Cl.
*A61M 5/32*      (2006.01)
*A61M 5/178*    (2006.01)
(Continued)

(52) U.S. Cl.
CPC .......... *A61M 5/3221* (2013.01); *A61M 5/178* (2013.01); *A61M 5/2066* (2013.01);
(Continued)

(58) Field of Classification Search
CPC ........ A61M 2005/3231; A61M 5/3234; A61M 5/3221; A61M 5/3232; A61M 2005/323; A61M 2005/3241
See application file for complete search history.

(56) References Cited

U.S. PATENT DOCUMENTS

| 4,995,870 A | * | 2/1991 | Baskas ................... A61C 19/00 604/110 |
| 5,290,233 A | * | 3/1994 | Campbell ............. A61M 5/322 604/110 |

(Continued)

FOREIGN PATENT DOCUMENTS

| NL | 8801072 | 11/1989 |
| WO | WO 2015/164839 | 10/2015 |
| WO | WO-2015164839 A2 * | 10/2015 .......... A61M 5/5066 |

OTHER PUBLICATIONS

PCT International Search Report for PCT/US2017/059596, Applicant: Credence MedSystems, Inc., Form PCT/ISA/210 and 220, dated Apr. 4, 2018.
(Continued)

*Primary Examiner* — Jenna Zhang
(74) *Attorney, Agent, or Firm* — Vista IP Law Group, LLP

(57) ABSTRACT

A system for injecting includes a syringe body defining a proximal opening and a distal needle interface. The system also includes a plunger member defining a plunger interior and configured to be manually manipulated to insert a stopper member relative to the syringe body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle assembly includes
(Continued)

a needle having a needle proximal end feature, a hub, and a needle latching member configured to couple the needle to the hub. The needle is retractable into plunger interior upon manipulation of the plunger member to actuate the energy-storage member latching member.

10 Claims, 72 Drawing Sheets

Related U.S. Application Data on Mar. 31, 2017, provisional application No. 62/431,382, filed on Dec. 7, 2016, provisional application No. 62/416,102, filed on Nov. 1, 2016.

(51) Int. Cl.

| | | |
|---|---|---|
| *A61M 5/24* | (2006.01) | |
| *A61M 5/20* | (2006.01) | |
| *A61M 5/28* | (2006.01) | |
| *A61M 5/315* | (2006.01) | |
| *A61M 5/31* | (2006.01) | |
| *A61J 1/20* | (2006.01) | |

(52) U.S. Cl.
CPC ............ *A61M 5/2448* (2013.01); *A61M 5/28* (2013.01); *A61M 5/284* (2013.01); *A61M 5/3137* (2013.01); *A61M 5/3148* (2013.01); *A61M 5/31501* (2013.01); *A61M 5/31511* (2013.01); *A61M 5/31513* (2013.01); *A61M 5/3202* (2013.01); *A61M 5/322* (2013.01); *A61M 5/3234* (2013.01); *A61J 1/2006* (2015.05); *A61J 1/2096* (2013.01); *A61M 5/3232* (2013.01); *A61M 5/3293* (2013.01); *A61M 2005/323* (2013.01); *A61M 2005/3223* (2013.01); *A61M 2005/3231* (2013.01); *A61M 2005/3241* (2013.01)

(56) References Cited

U.S. PATENT DOCUMENTS

| | | | | |
|---|---|---|---|---|
| 5,997,511 | A  * | 12/1999 | Curie | A61M 5/322 |
| | | | | 604/195 |
| 9,814,842 | B2 | 11/2017 | Diaz et al. | |
| 2003/0004468 | A1* | 1/2003 | Righi | A61M 5/3234 |
| | | | | 604/243 |
| 2006/0106340 | A1* | 5/2006 | Goossens | A61M 5/322 |
| | | | | 604/110 |
| 2008/0140005 | A1* | 6/2008 | Luo | A61M 5/3234 |
| | | | | 604/110 |
| 2013/0035664 | A1 | 2/2013 | Mojdehbakhsh | |
| 2013/0079716 | A1* | 3/2013 | Thorley | A61M 5/31511 |
| | | | | 604/110 |
| 2014/0330217 | A1* | 11/2014 | Thorley | A61M 5/3232 |
| | | | | 604/198 |
| 2015/0005706 | A1 | 1/2015 | Diaz | |
| 2015/0148748 | A1* | 5/2015 | Shluzas | A61M 5/3221 |
| | | | | 604/196 |
| 2016/0206834 | A1* | 7/2016 | Shluzas | A61M 5/3276 |
| 2018/0117260 | A1 | 5/2018 | Shluzas | |
| 2018/0117261 | A1 | 5/2018 | Steese-Bradley | |
| 2018/0133408 | A1 | 5/2018 | Shluzas | |

OTHER PUBLICATIONS

PCT Written Opinion of the International Search Authority for PCT/US2017/059596, Applicant: Credence MedSystems, Inc., Form PCT/ISA/237, dated Apr. 4, 2018.

PCT International Preliminary Report on Patentability (Chapter I of the Patent Cooperation Treaty) for PCT/US2017/059596, Applicant: Credence MedSystems, Inc., Form PCT/ISA/326 and 373, dated May 16, 2019.

* cited by examiner

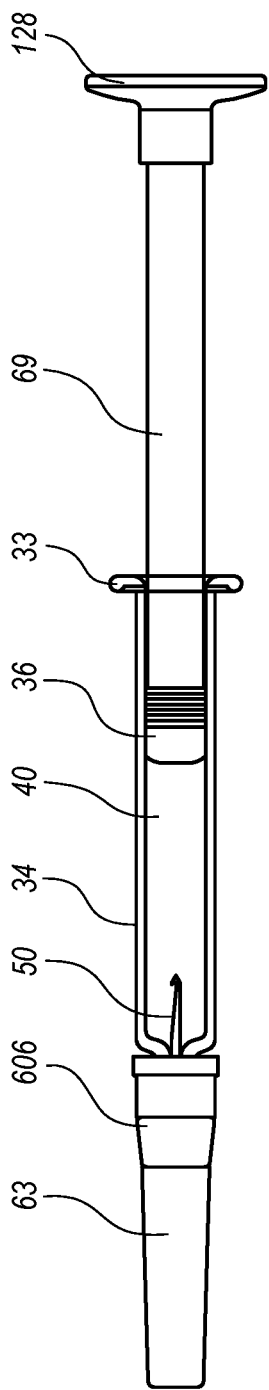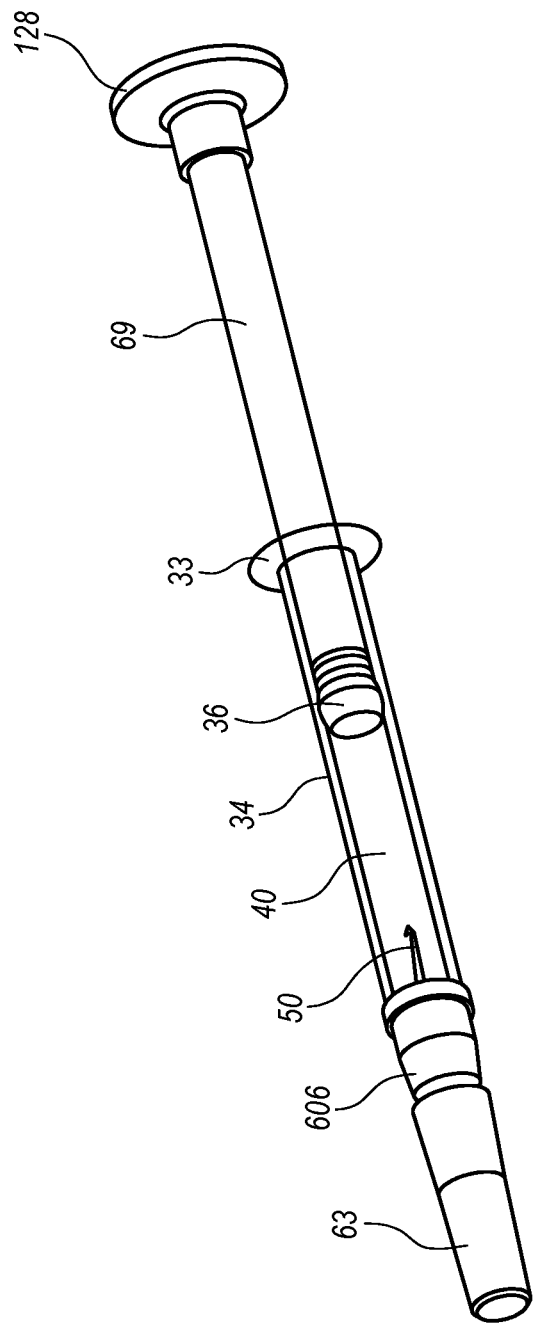

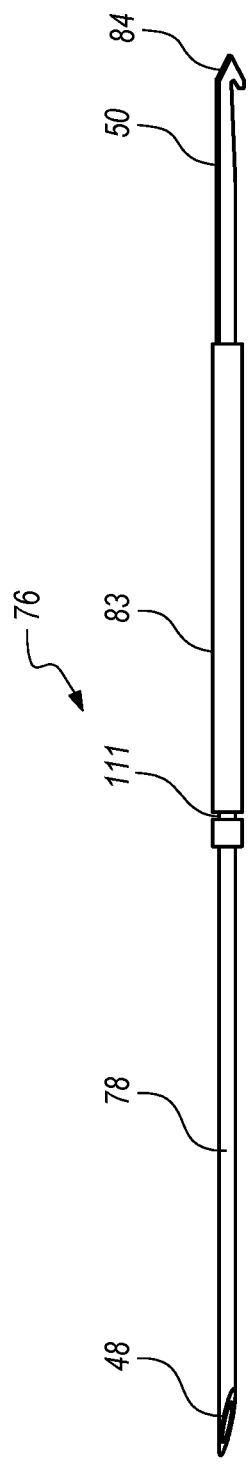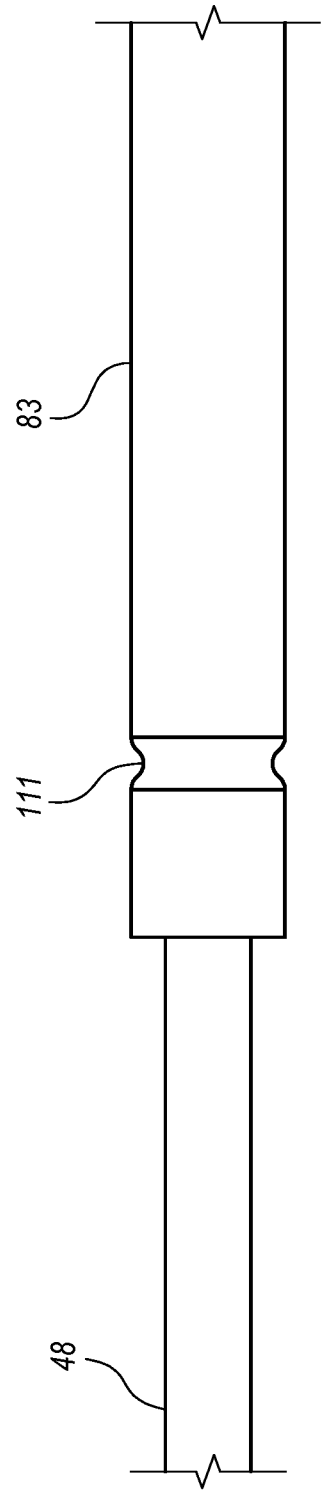

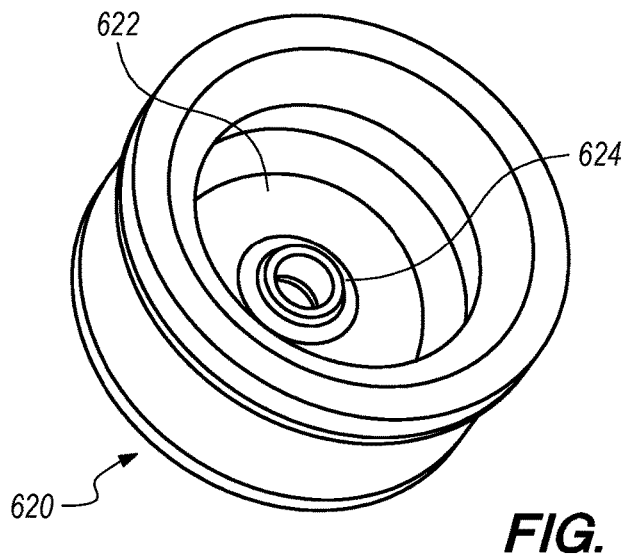
FIG. 6J
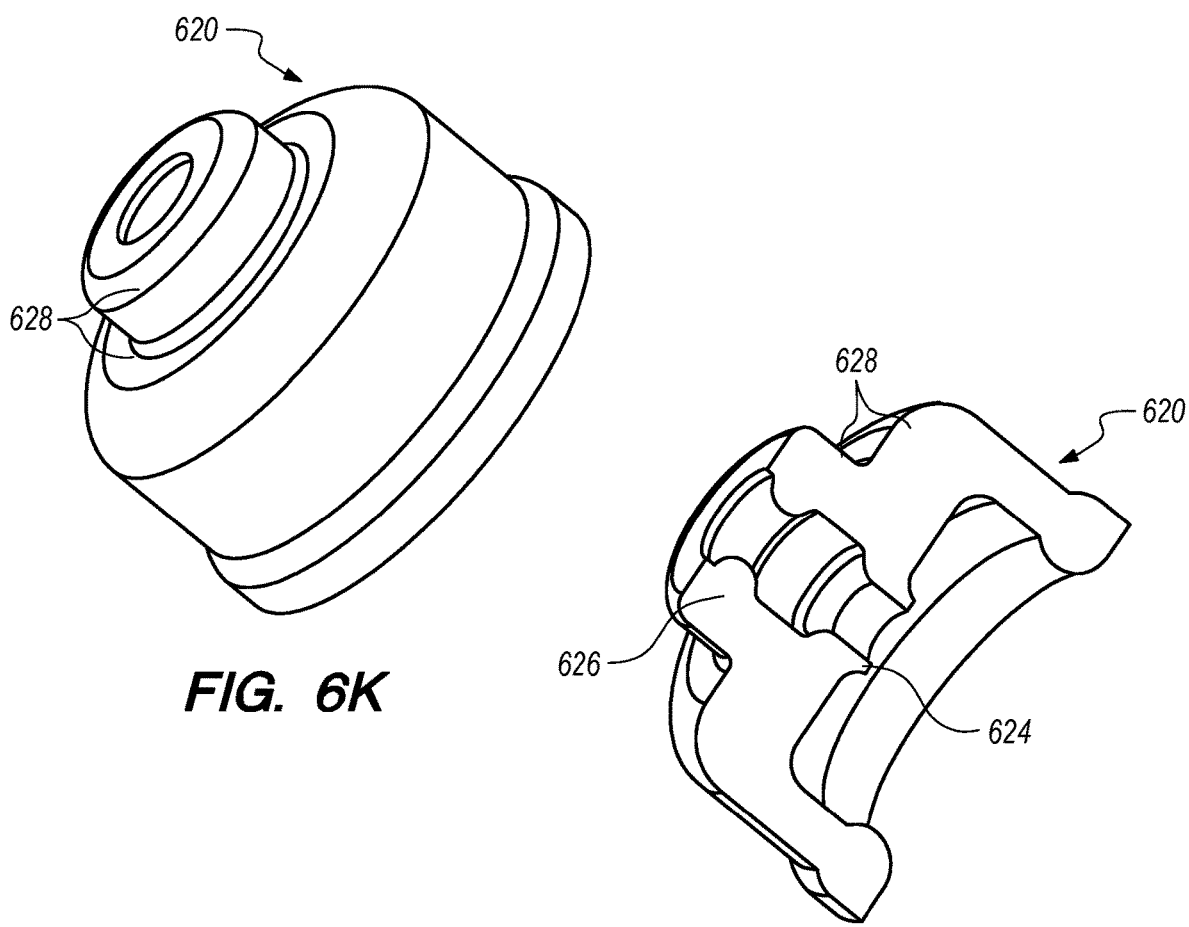
FIG. 6K
FIG. 6L

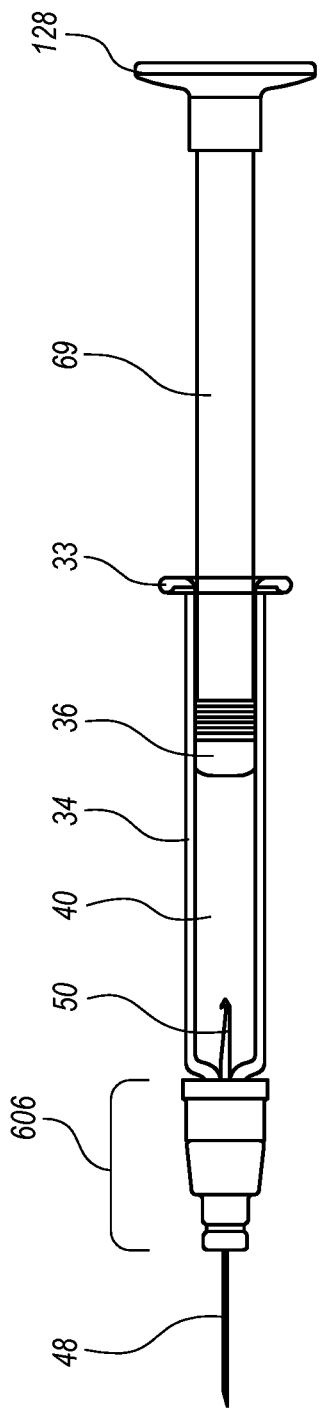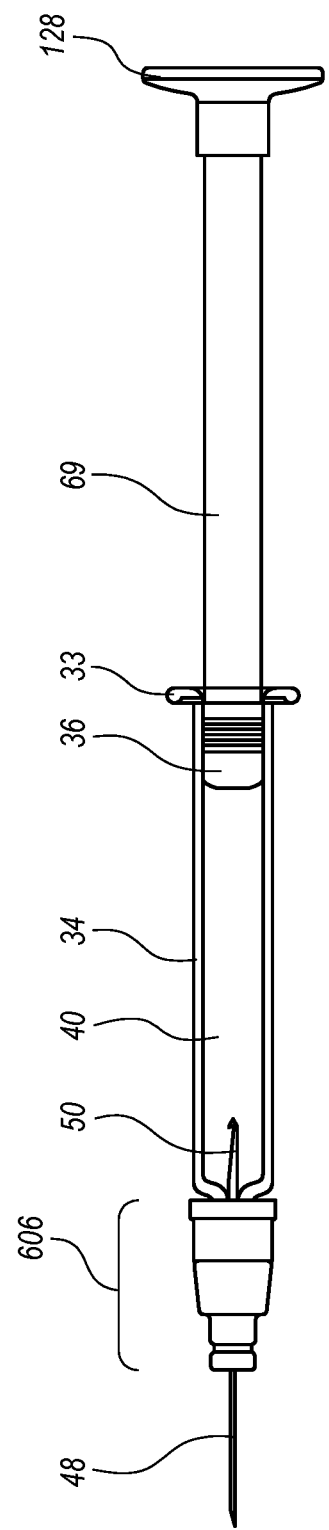
FIG. 6Q
FIG. 6R

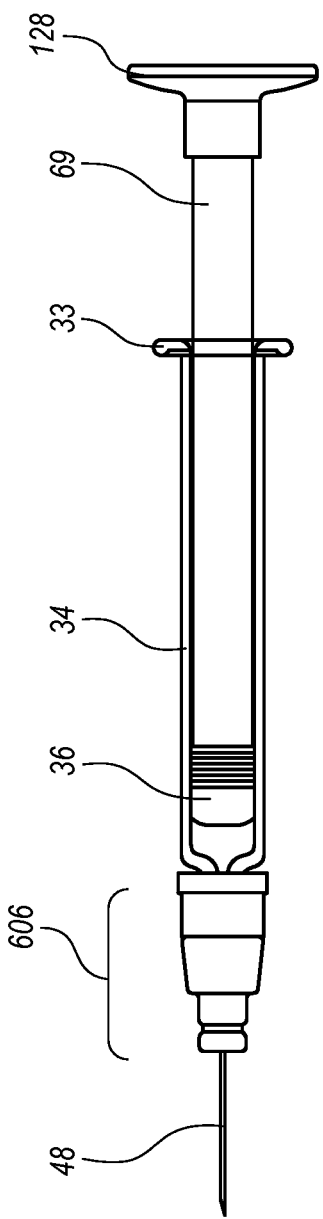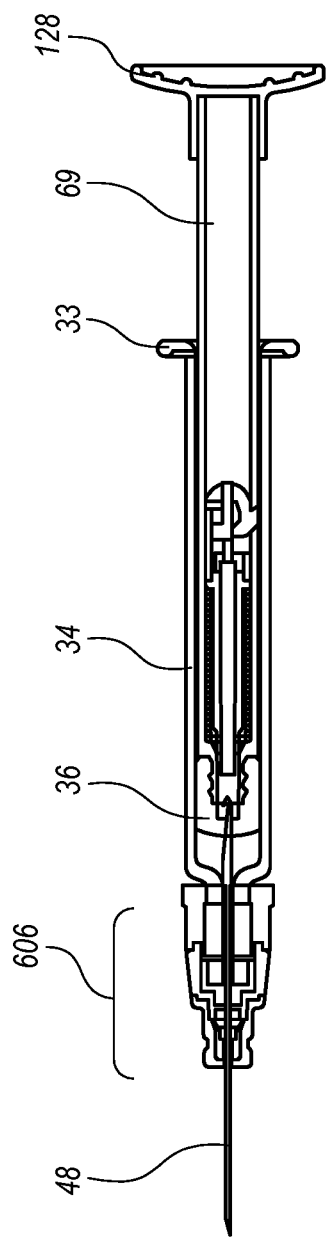

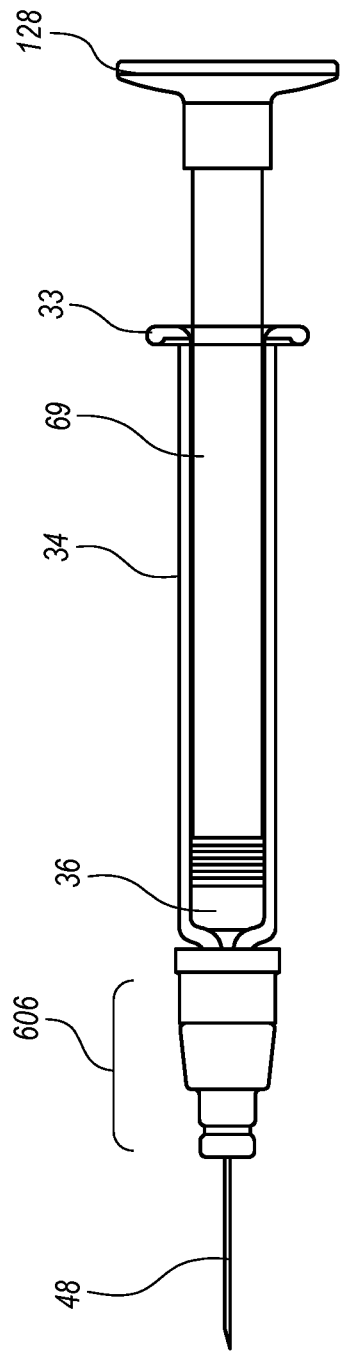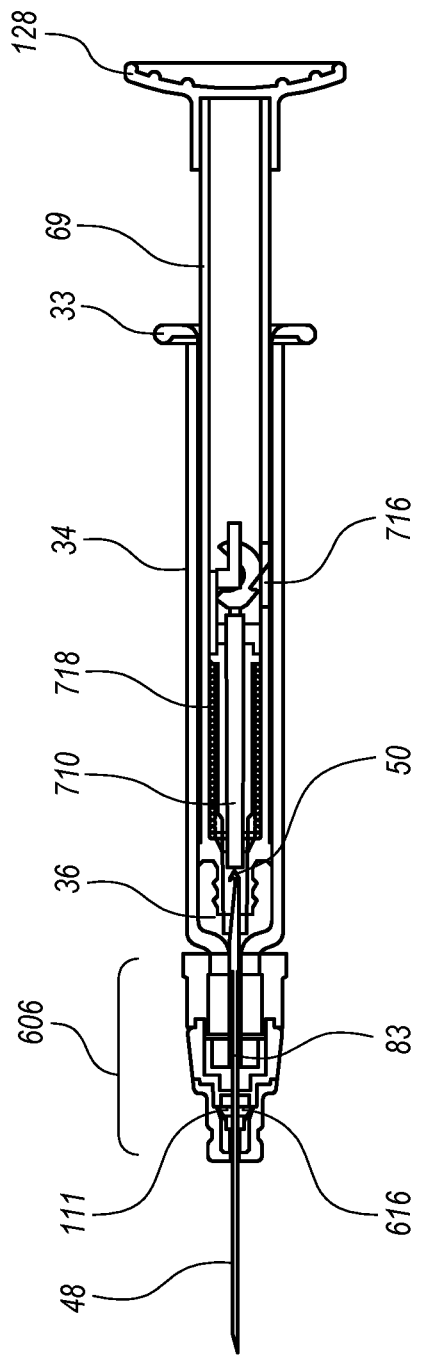

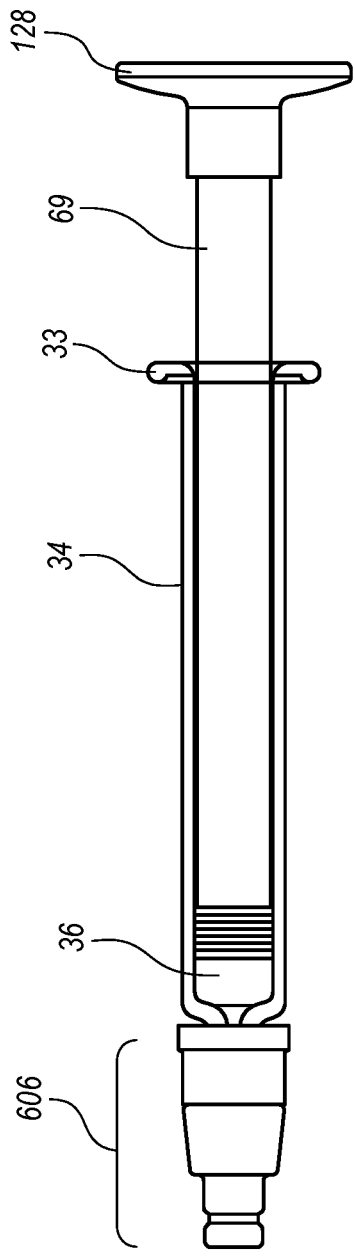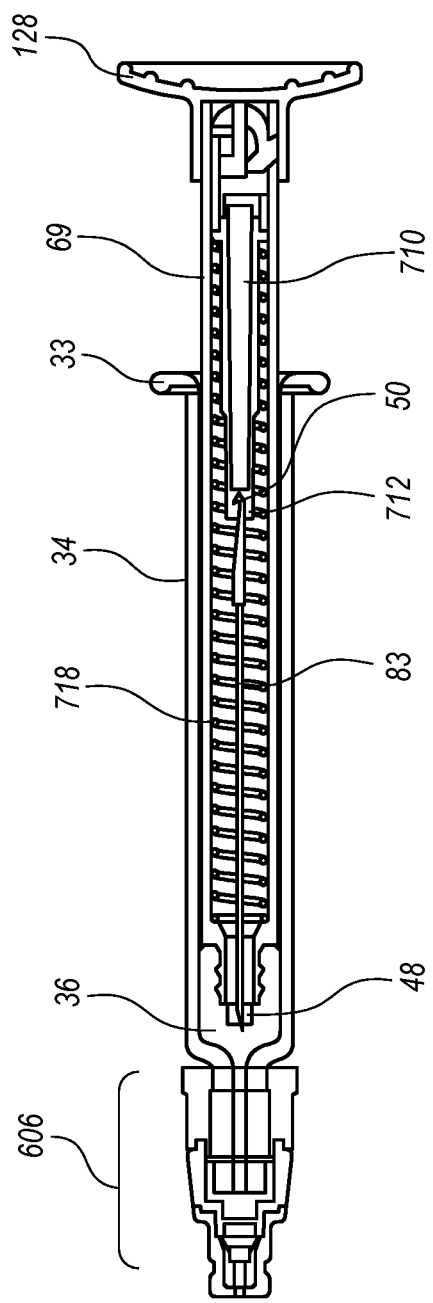
FIG. 6Y
FIG. 6Z

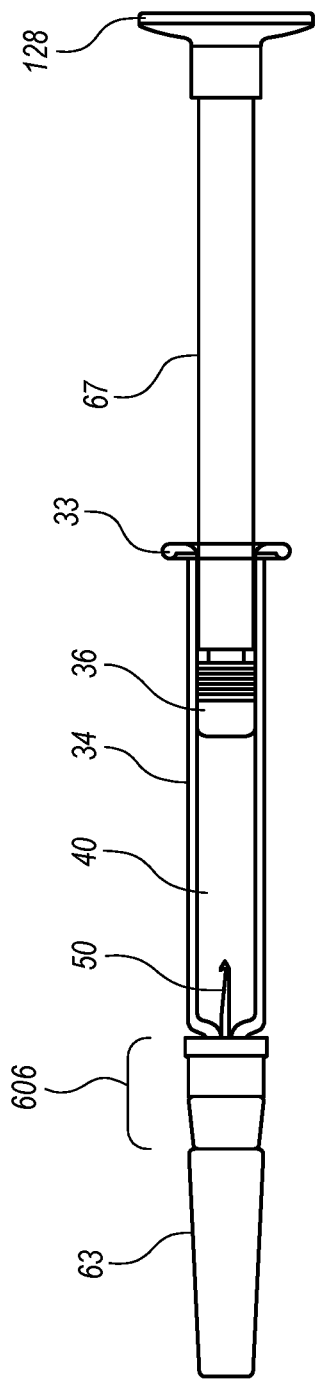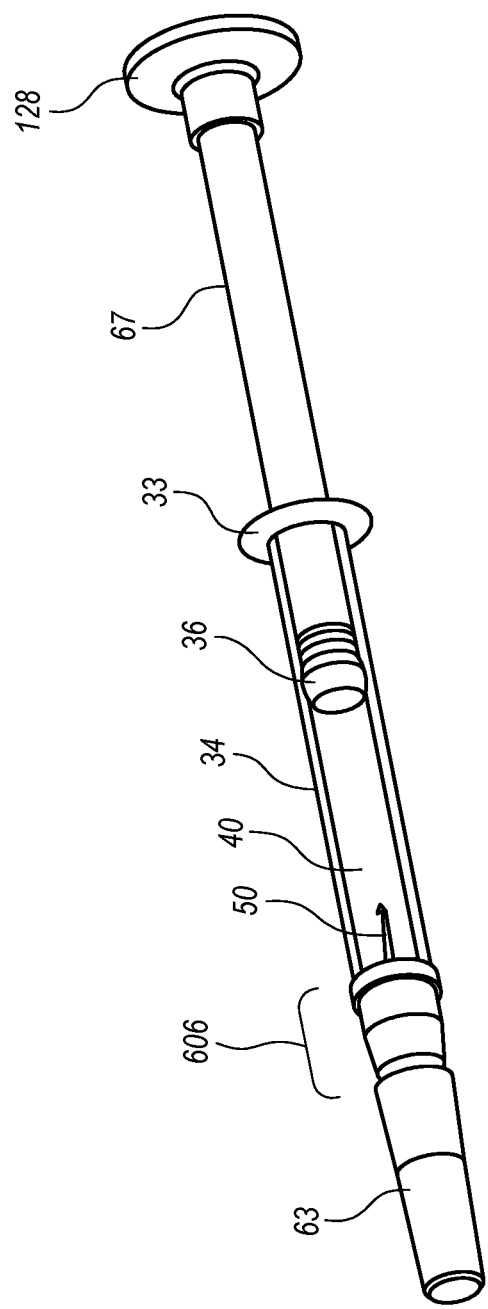
FIG. 7A
FIG. 7B

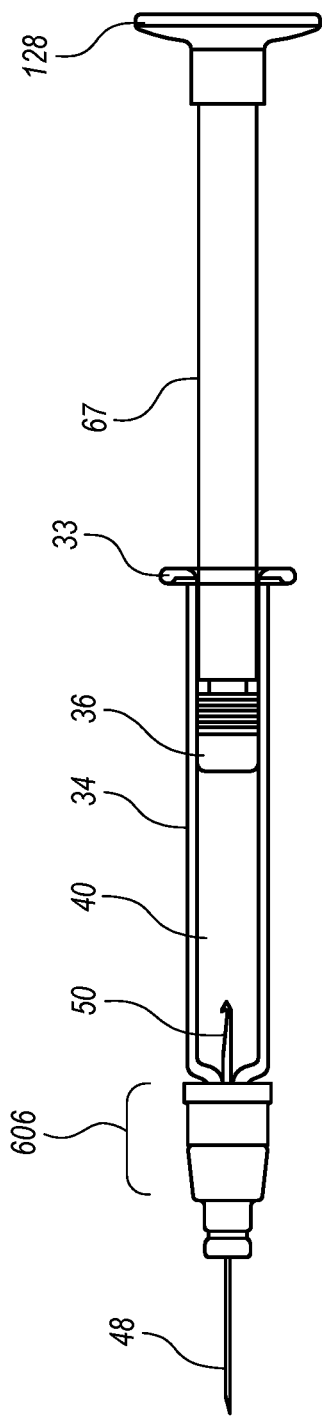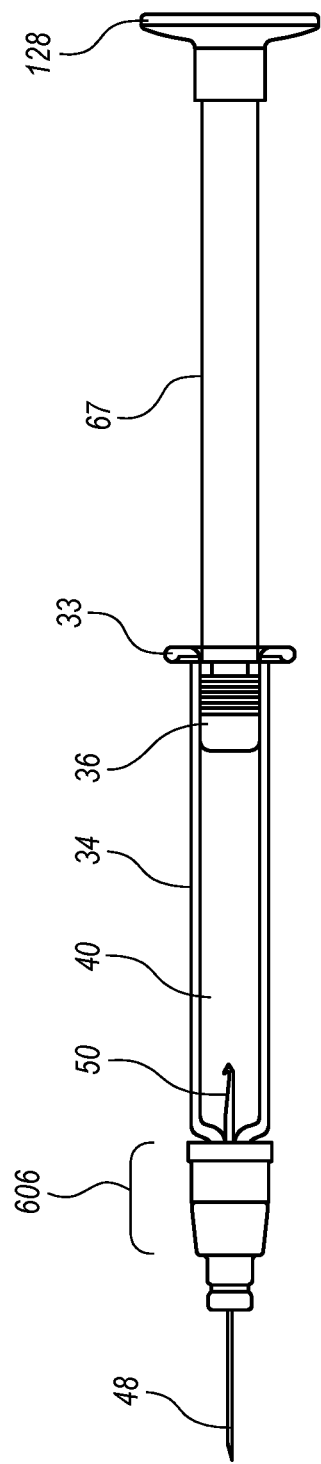
FIG. 7C
FIG. 7D

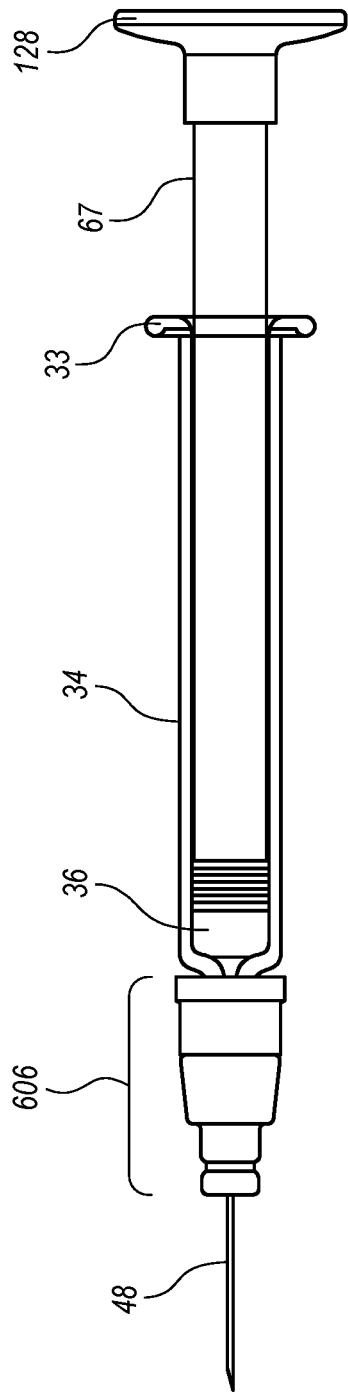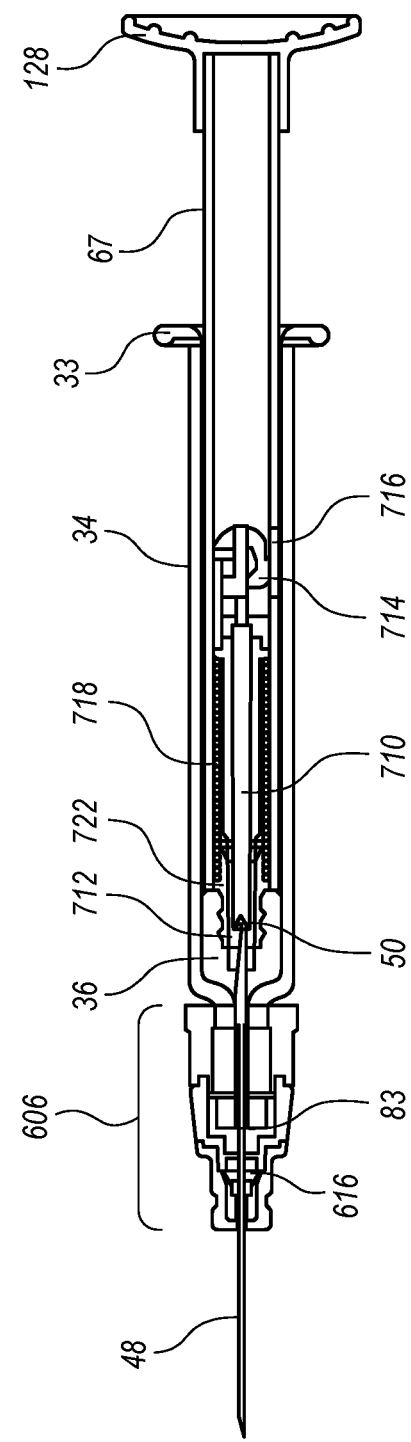

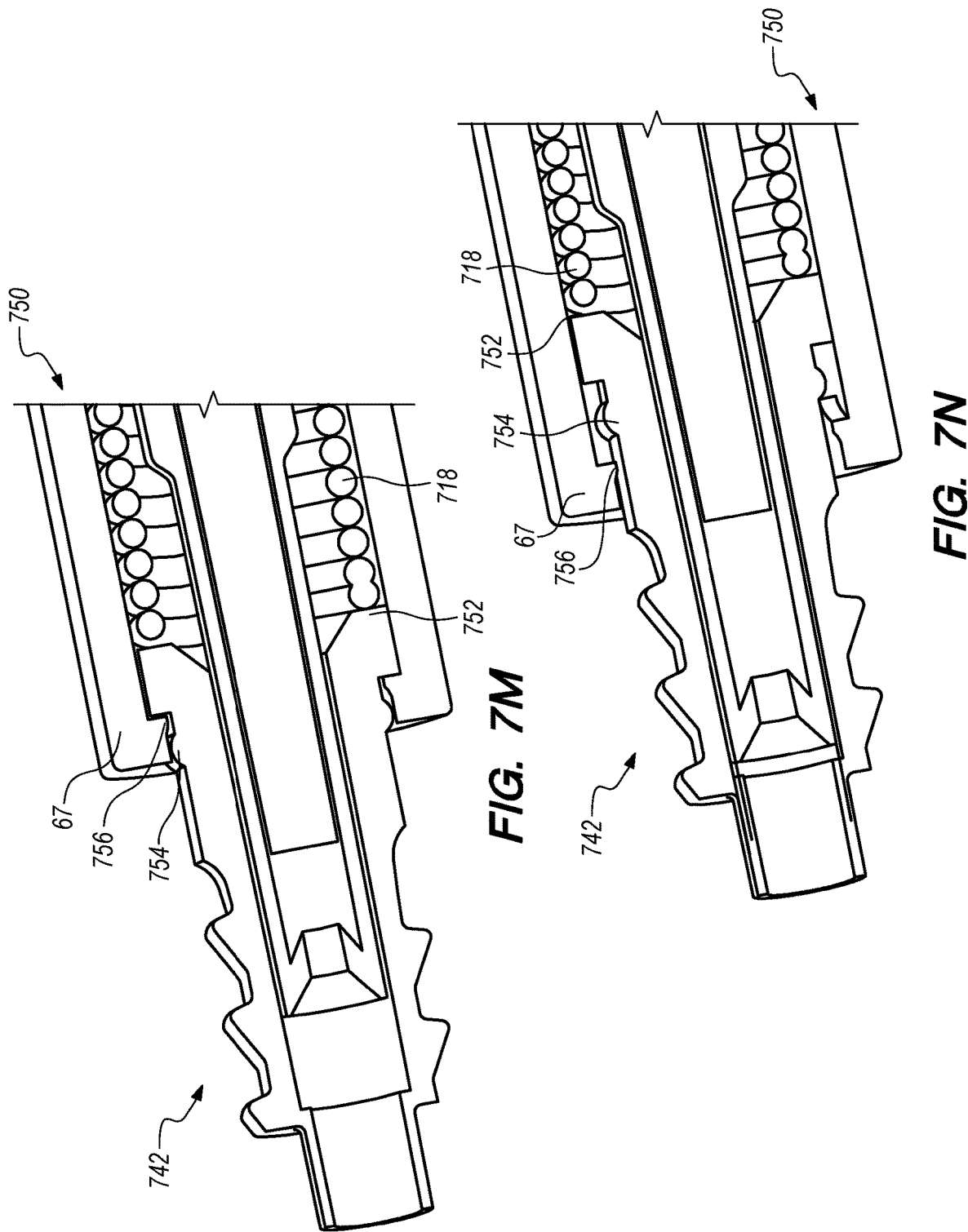

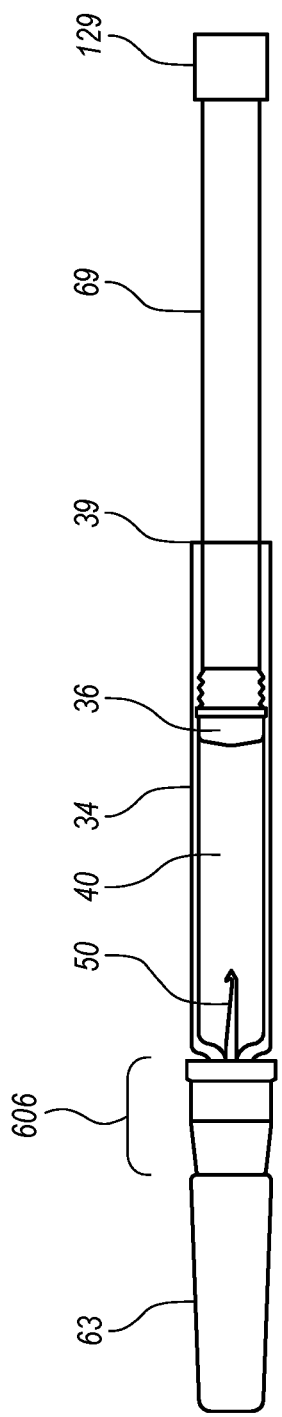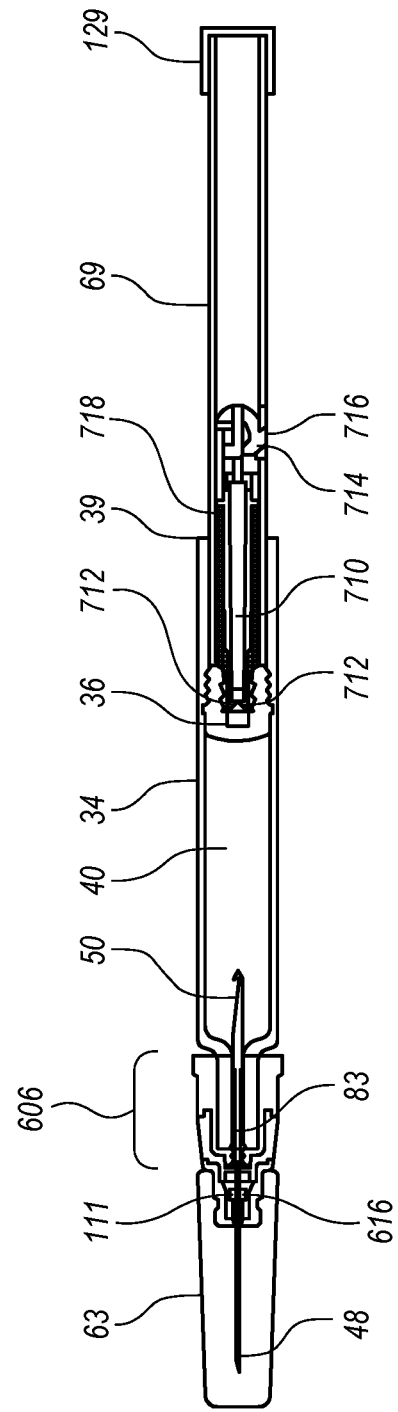

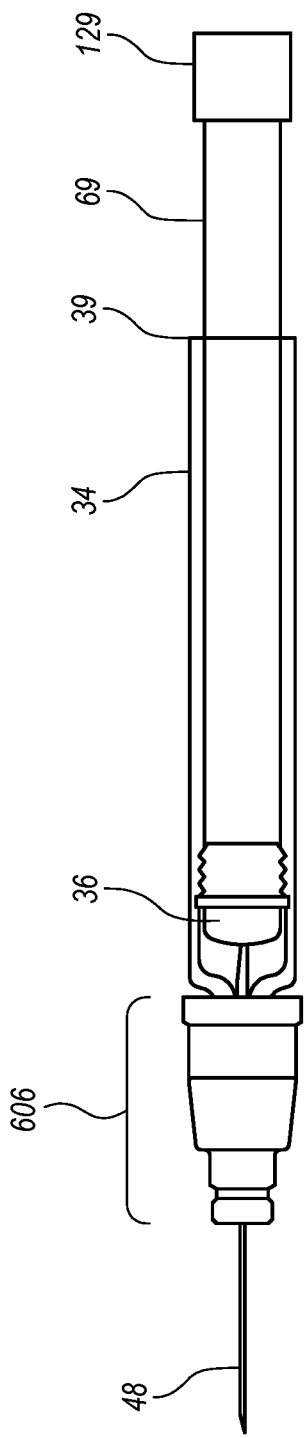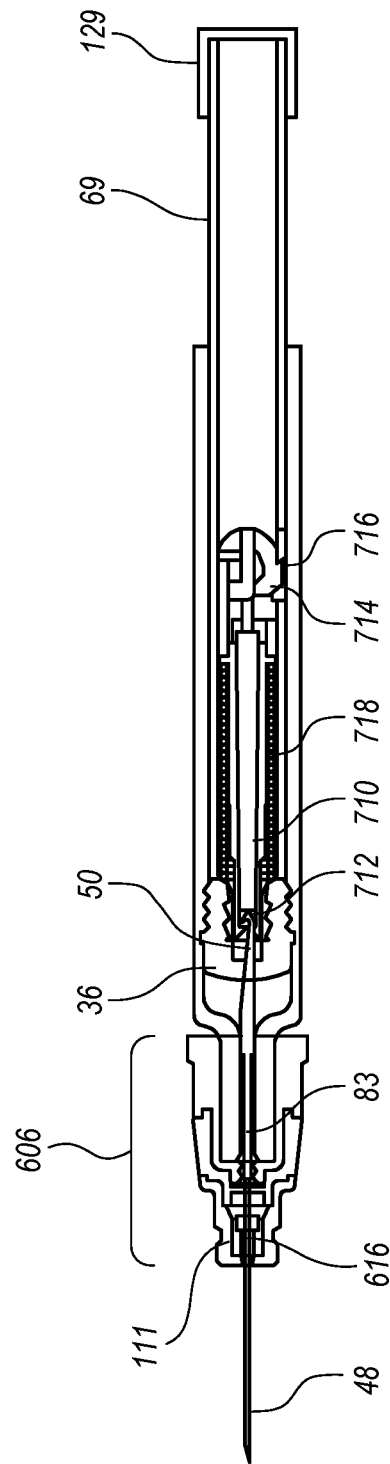
FIG. 8G
FIG. 8H

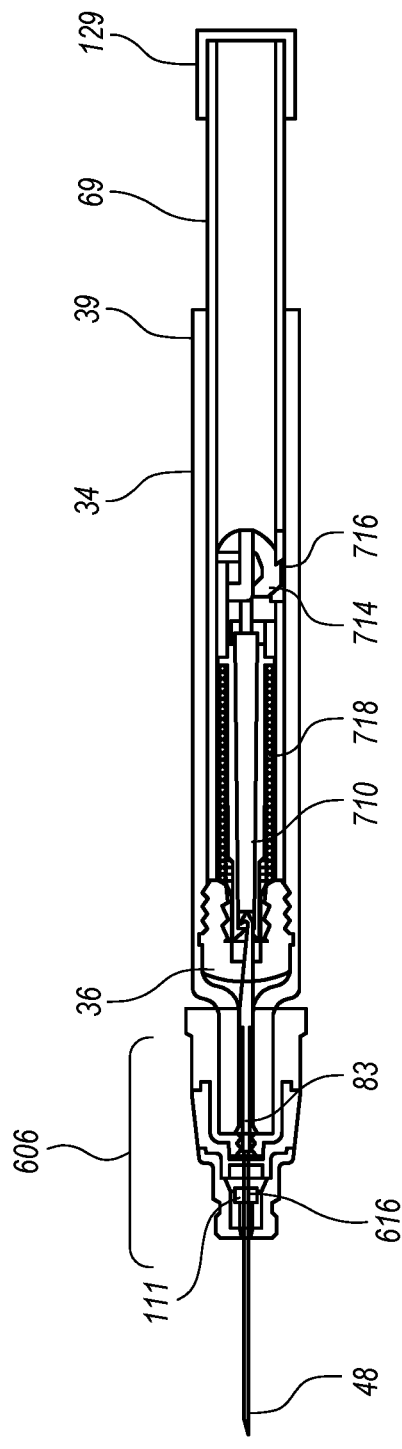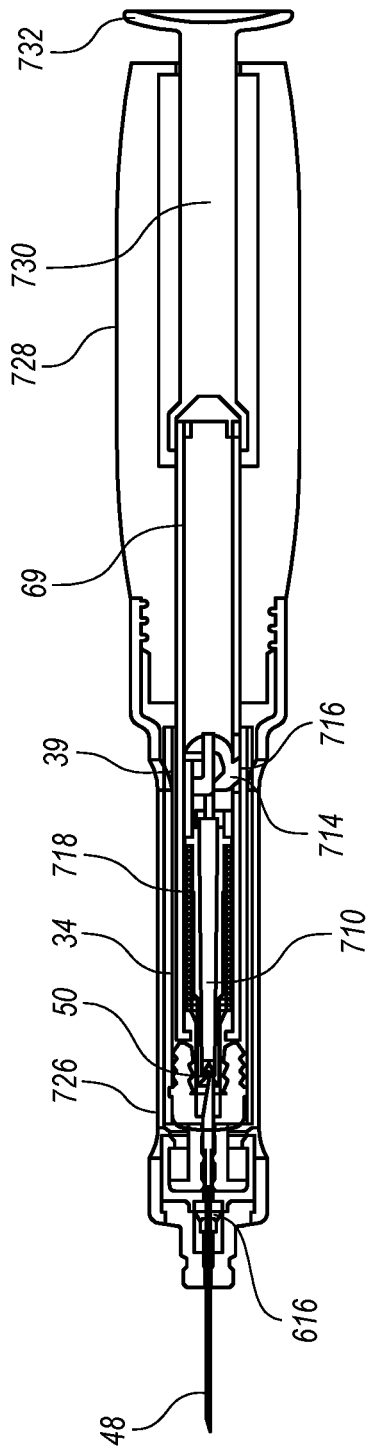
FIG. 8K
FIG. 8L

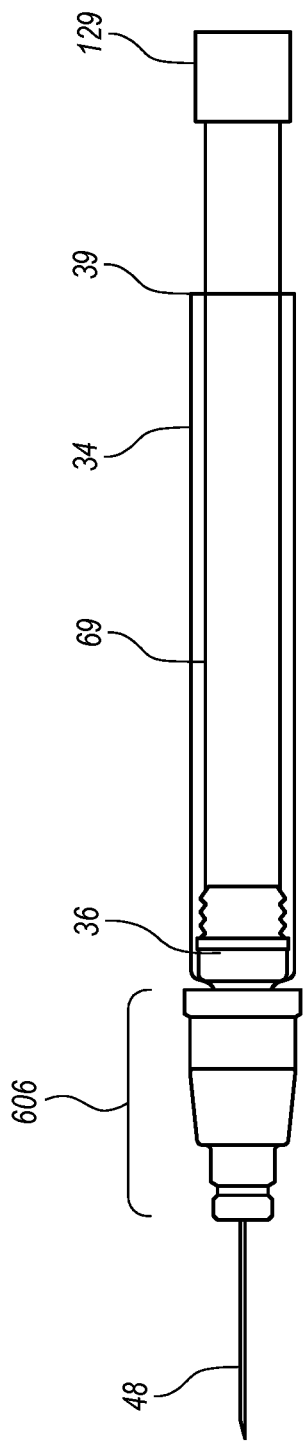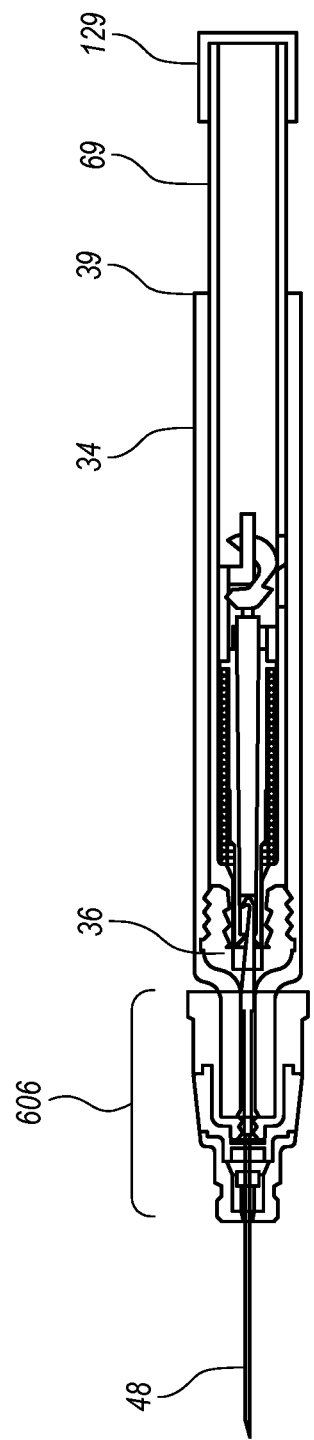

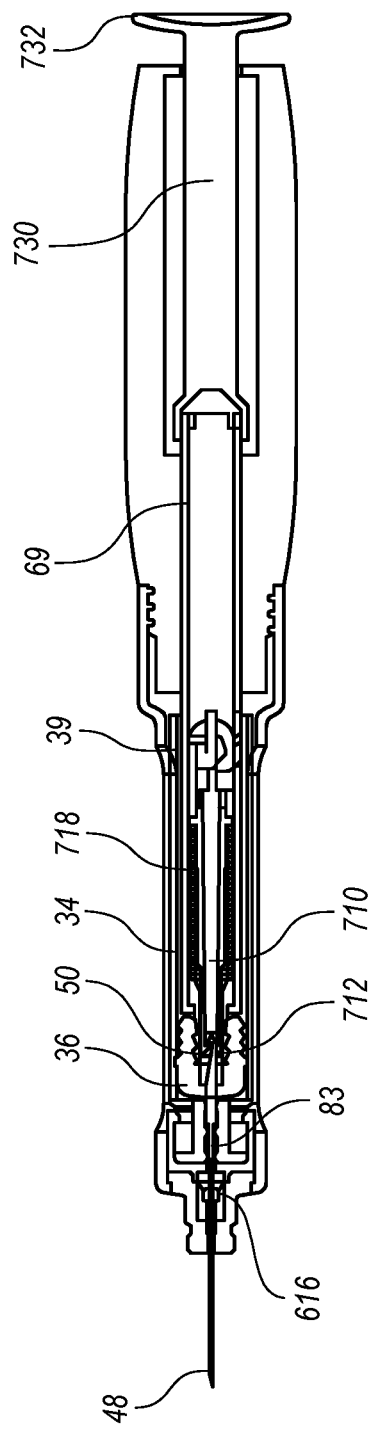
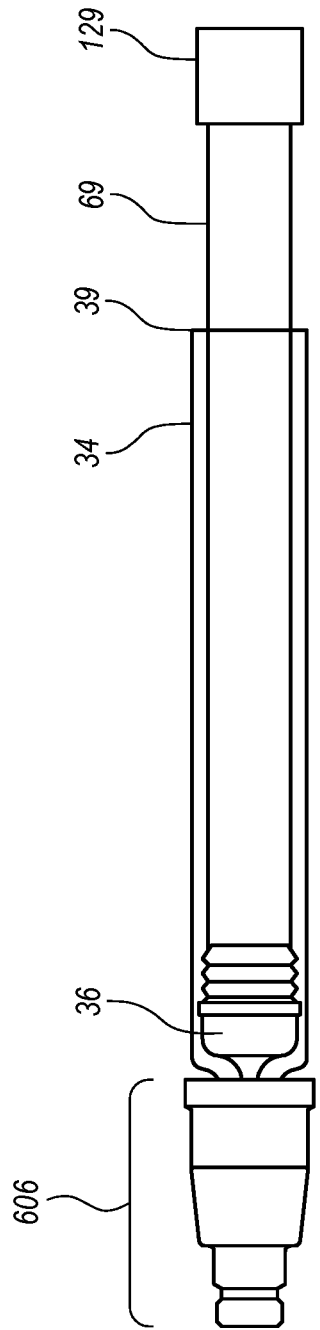
FIG. 8O
FIG. 8P

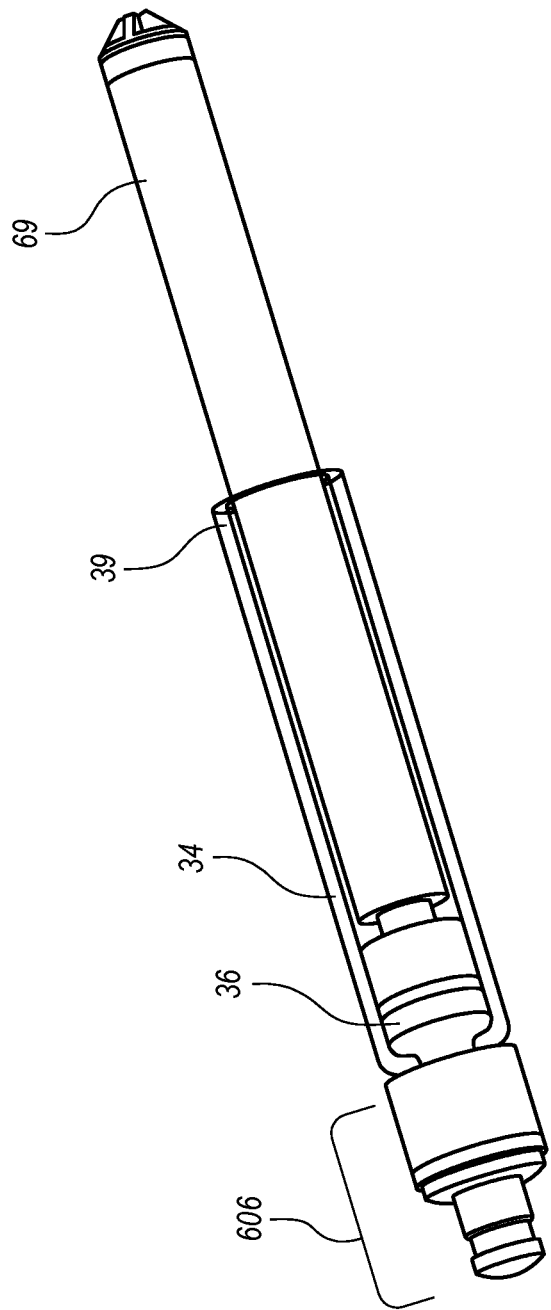

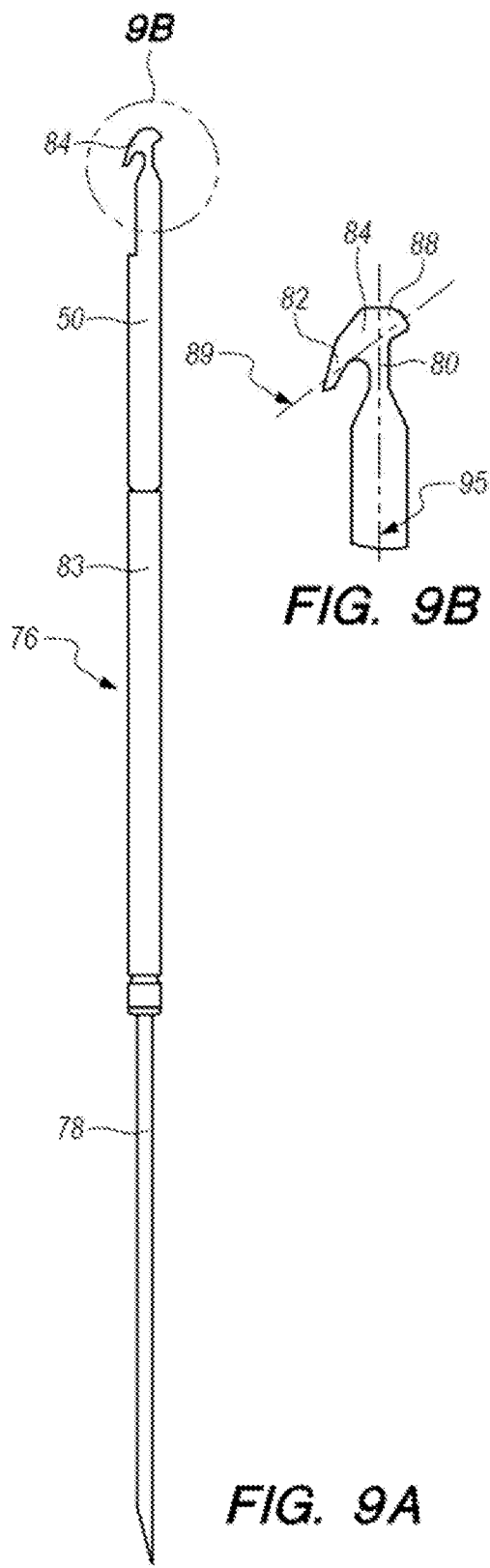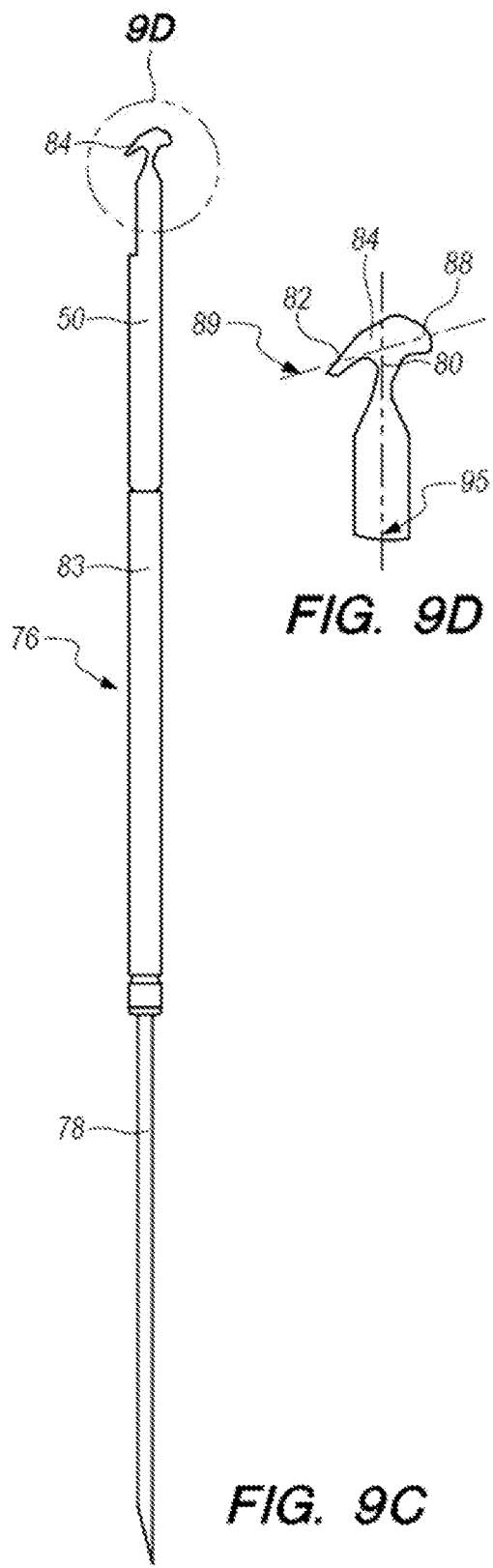

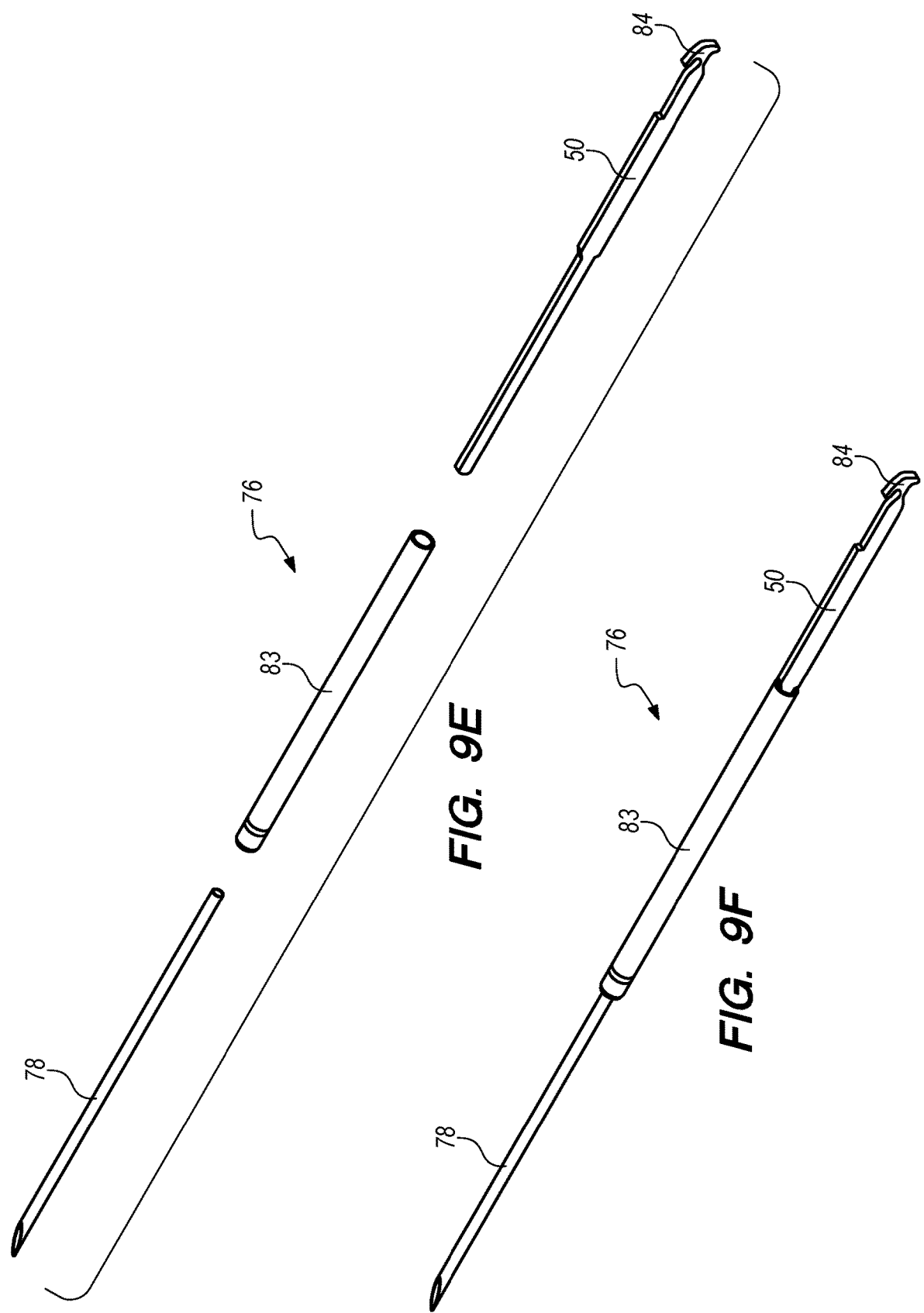

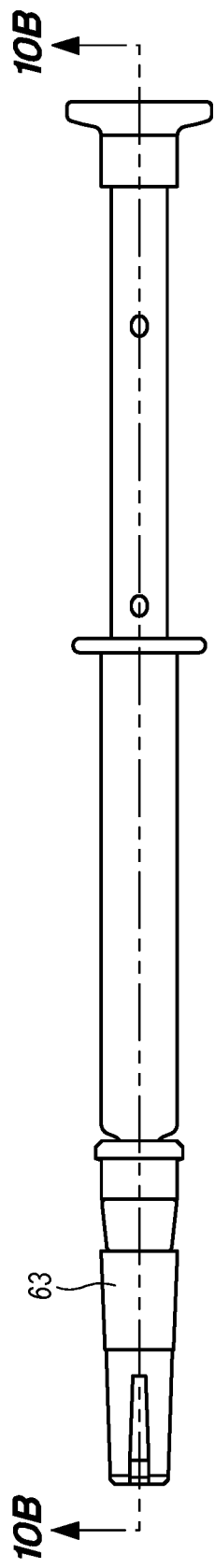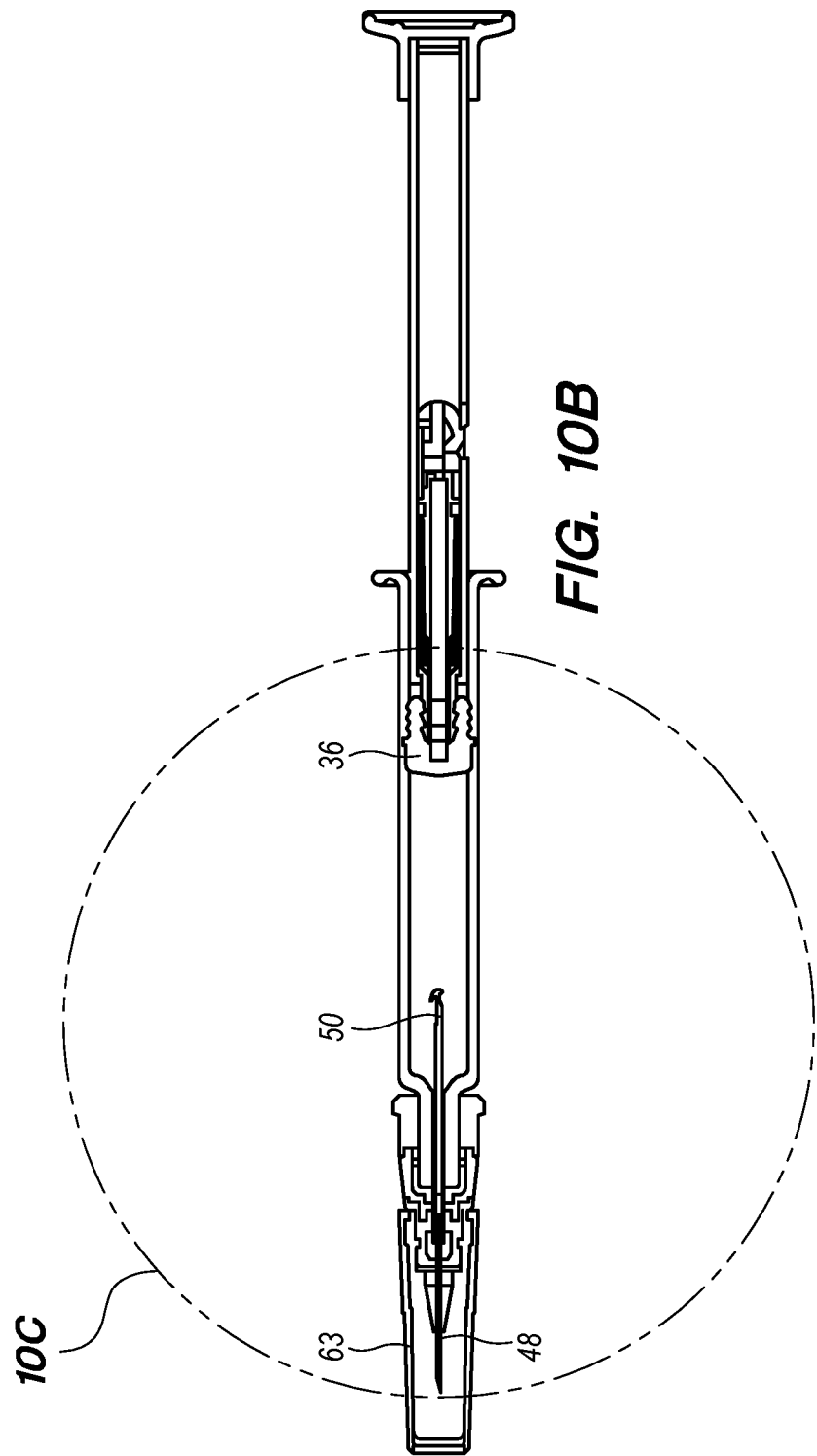

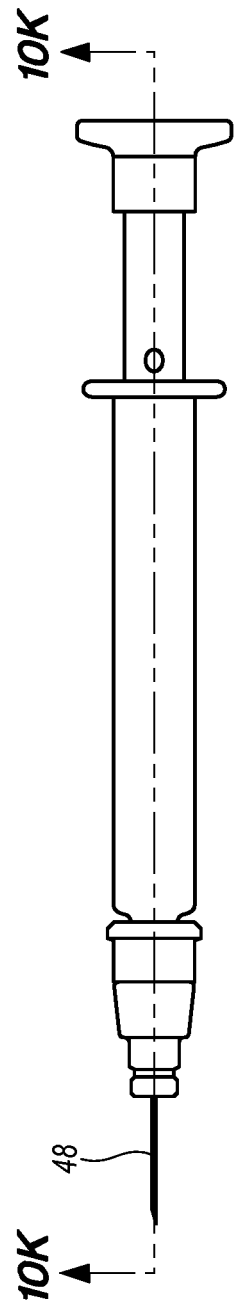
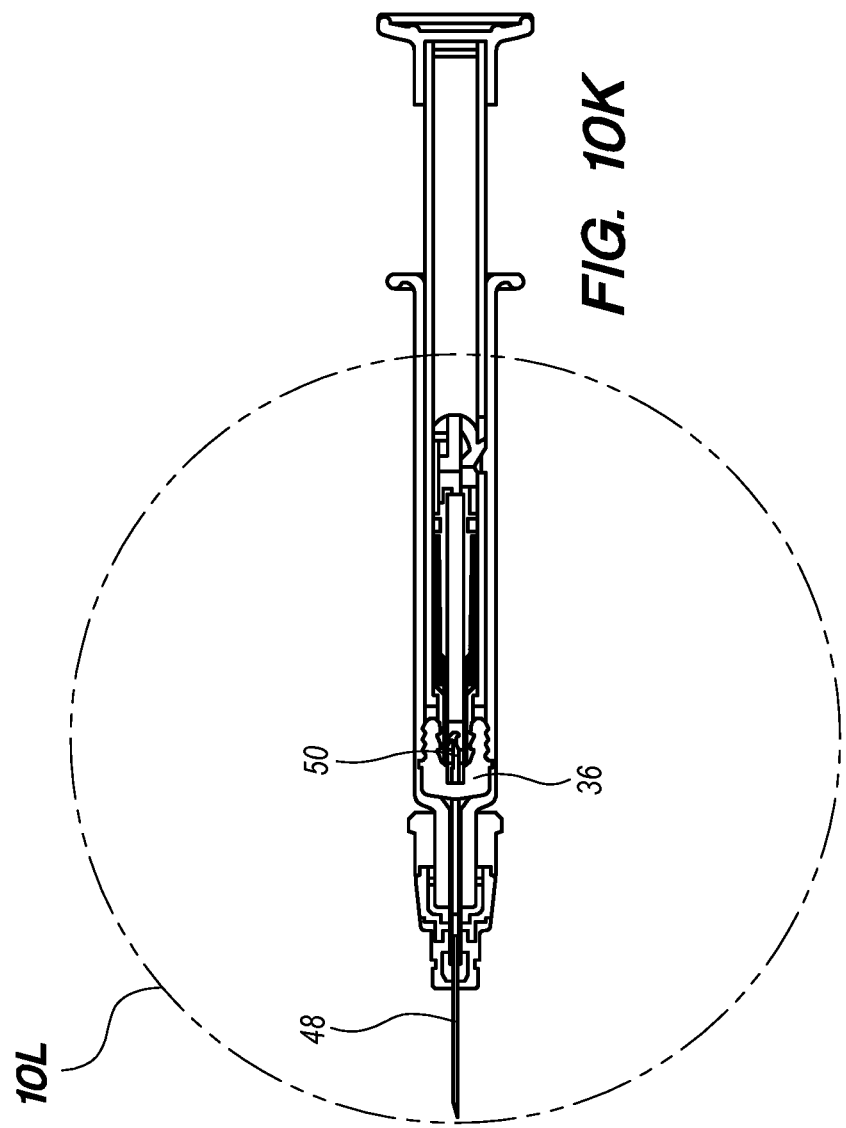

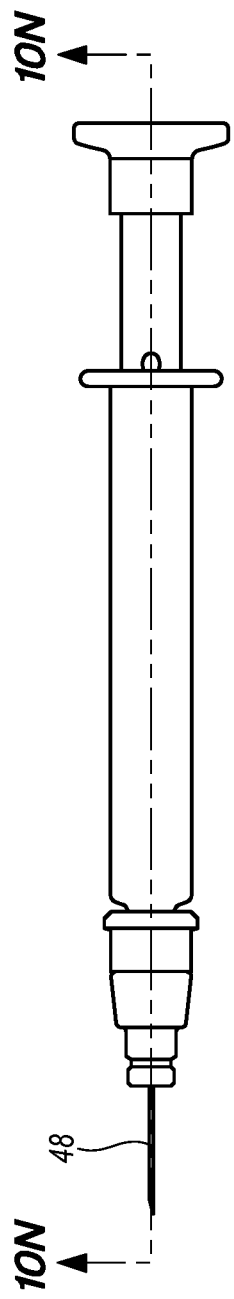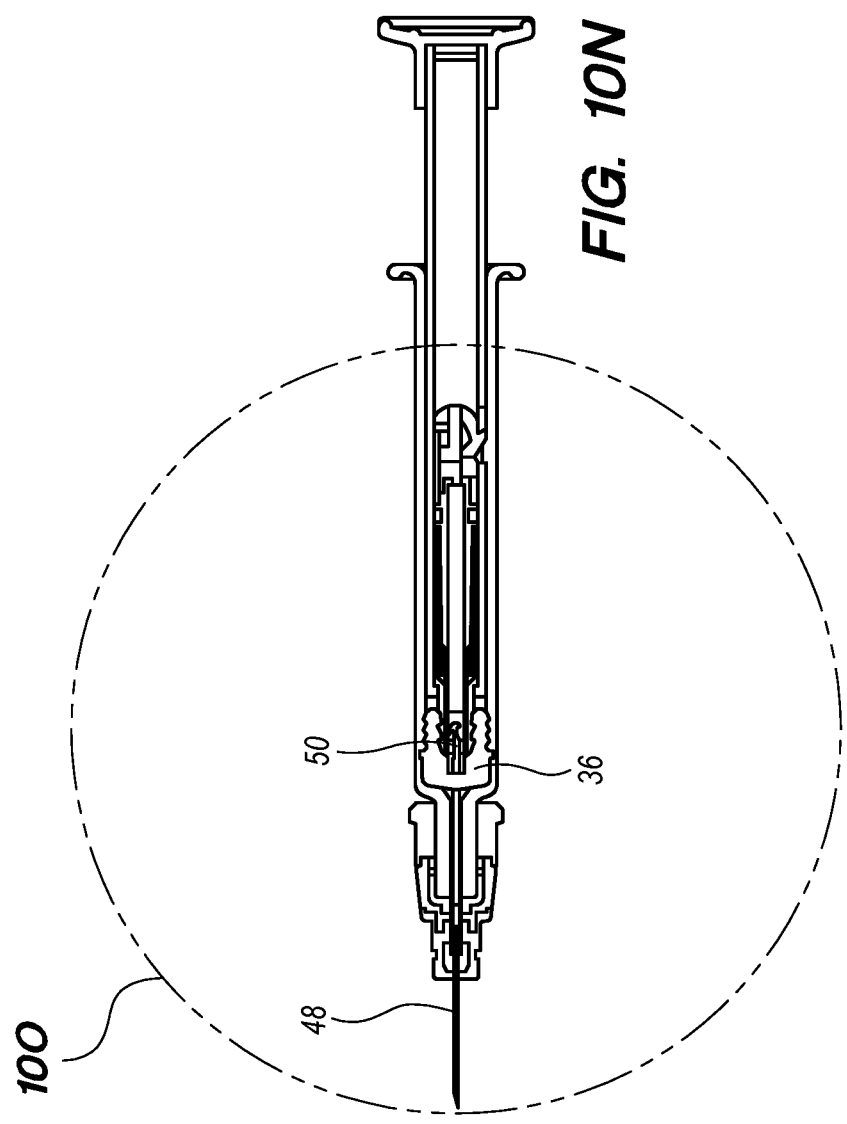

SYSTEM AND METHOD FOR SAFETY SYRINGE

CROSS-REFERENCE TO RELATED APPLICATION(S)

The present application claims priority to (1) U.S. Provisional Patent Application Ser. No. 62/416,102, filed on Nov. 1, 2016 and entitled "SYSTEM AND METHOD FOR SAFETY SYRINGE"; (2) U.S. Provisional Patent Application Ser. No. 62/431,382, filed on Dec. 7, 2016 and entitled "SYSTEM AND METHOD FOR SAFETY SYRINGE"; (3) U.S. Provisional Patent Application Ser. No. 62/480,276, filed Mar. 31, 2017 and, entitled "SYSTEM AND METHOD FOR SAFETY SYRINGE"; (4) U.S. Provisional Patent Application Ser. No. 62/542,230, filed Aug. 7, 2017 and entitled "CARTRIDGE SAFETY INJECTION SYSTEM AND METHODS." This application includes subject matter similar to the subject matter described in the following co-owned U.S. patent applications: (1) U.S. Utility application Ser. No. 14/696,342, filed Apr. 24, 2015, entitled "SYSTEM AND METHOD FOR SAFETY SYRINGE"; (2) U.S. Utility application Ser. No. 14/543,787, filed Nov. 17, 2014, entitled "SYSTEM AND METHOD FOR DRUG DELIVERY WITH A SAFETY SYRINGE"; (3) U.S. Utility application Ser. No. 14/321,706, filed Jul. 1, 2014, entitled "SAFETY SYRINGE"; (4) U.S. Utility application Ser. No. 14/801,259, filed on Nov. 1, 2017 and entitled "SYSTEM AND METHOD FOR SAFETY SYRINGE"; (5) U.S. Utility application Ser. No. 14/801,304, filed on Nov. 1, 2017 and, entitled "SYSTEM AND METHOD FOR SAFETY SYRINGE"; and (6) U.S. Utility application Ser. No. 14/801,281, filed on Nov. 1, 2017 and, entitled "CARTRIDGE SAFETY INJECTION SYSTEM AND METHODS." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating, to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross sectional shape may establish a seal against the syringe body (34)), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

There is a need for injection systems which address the shortcomings of currently-available configurations. In particular, there is a need for safety injection solutions which may utilize the existing and relatively well-controlled supply chain of conventionally delivered pre-filled syringe assemblies such as those described in reference to FIGS. 5A and 5B.

SUMMARY

Embodiments are directed to injection systems. In particular, the embodiments are directed to safe injection systems that move the needle into a protected configuration to minimize accidental user injury and contamination with used needles.

In one embodiment, a system for injecting includes a syringe body defining a proximal opening and a distal needle interface. The system also includes a plunger member defining a plunger interior and configured to be manually manipulated to insert a stopper member relative to the syringe body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the syringe body. The needle assembly includes a needle having a needle proximal end feature, a hub, and a needle latching member configured to couple the needle to the hub. The needle is at least partially retractable into plunger interior upon manipulation of the plunger member relative to the syringe body to transform the energy-storage member latching member from a latched state to an unlatched state. The energy-storage member latching member is intercoupled between an interior surface of the plunger member and the needle retention feature.

In one or more embodiments, the needle proximal end feature and the needle retention feature are configured to selectively couple the needle to the needle retention feature.

The needle proximal end feature may have a reduced axial profile in the first configuration relative to the second configuration.

In one or more embodiments, the needle proximal end feature includes an articulating hinge and has first and second configurations, and the needle retention feature includes an opening sized to allow passage of the needle proximal end feature in the first configuration and to prevent passage of the needle proximal end feature in the second configuration. The articulating hinge may be a living hinge. The needle proximal end feature may include a proximal end coupled to an articulating portion by the articulating hinge. The proximal end may have a proximal end longitudinal axis that is closer to orthogonal to a longitudinal axis of the articulating portion in the second configuration compared to the first configuration. The needle proximal end feature may have a "T" shape. The needle proximal end feature may have a flat cross-section. The needle retention feature may include a funnel-shaped flange defining the opening and configured to guide the needle proximal feature into the opening. After a proximal end of the needle proximal end feature has been inserted through the opening into the needle retention feature, proximal movement of the needle retention feature may move the needle proximal end feature from the first configuration to the second configuration.

In one or more embodiments, the needle proximal end feature includes an extending portion and has a first configuration where the extending portion is at least partially retracted and a second configuration where the extending portion is extended, and the needle retention feature includes an opening sized to allow passage of the needle proximal end feature in the first configuration and to prevent passage of the needle proximal end feature in the second configuration. The extending portion may be biased to extend to place the needle proximal end feature in the second configuration. The needle proximal end feature may have a flat cross-section. The extending portion may extend by pivoting out of a plane of the flat cross-section. The needle proximal end feature may also include a second extending portion. The extending portion and the second extending portion may pivot out of the plane of the flat cross-section in opposite directions.

In one or more embodiments, the needle proximal end feature includes an angled portion, and the needle retention feature includes a tubular member sized to allow passage of the needle proximal end feature in a first direction and to prevent passage of the needle proximal end feature in a second direction opposite to the first direction. The tubular member may be elastically deformable. The needle proximal end feature may include a cylindrical body. The angled portion may be a barb biased to extend radially outward and proximally from the cylindrical body. The needle retention feature may include a funnel-shaped flange around a distal opening. The needle retention feature may also include a second barb biased to extend radially outward and proximally from the cylindrical body. The barb and second barb may be on opposite sides of the cylindrical body and offset along a longitudinal axis of the cylindrical body. The needle proximal end feature may include a flat body. The angled portion may be a non-articulating tooth extending outward and proximally from a longitudinal axis of the flat body.

In one or more embodiments, the needle proximal end feature includes a pointed end without sharp edges.

In one or more embodiments, the needle latching member includes a locking detent releasable by distal movement of the needle to uncouple the needle from the hub.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein.

Figure 1A:
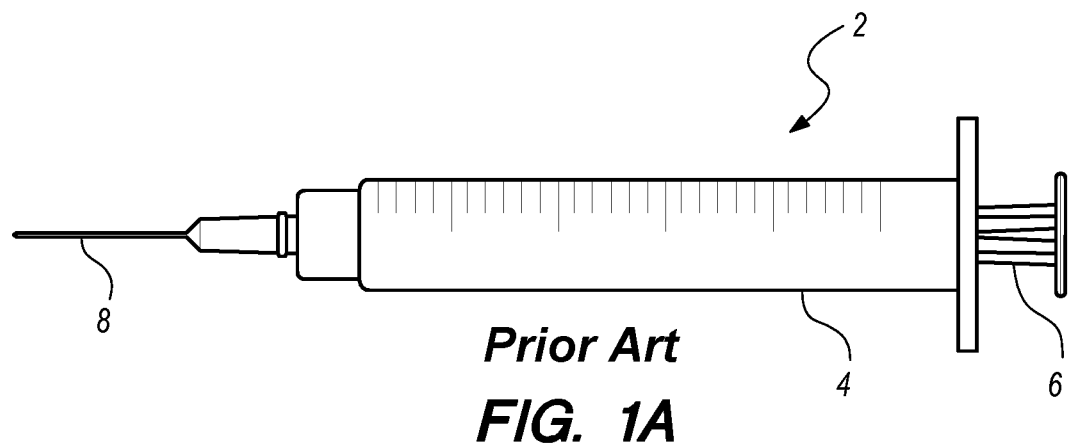
FIGS. 1A-5C illustrate various aspects of conventional injection syringe configurations.
Figure 1B:
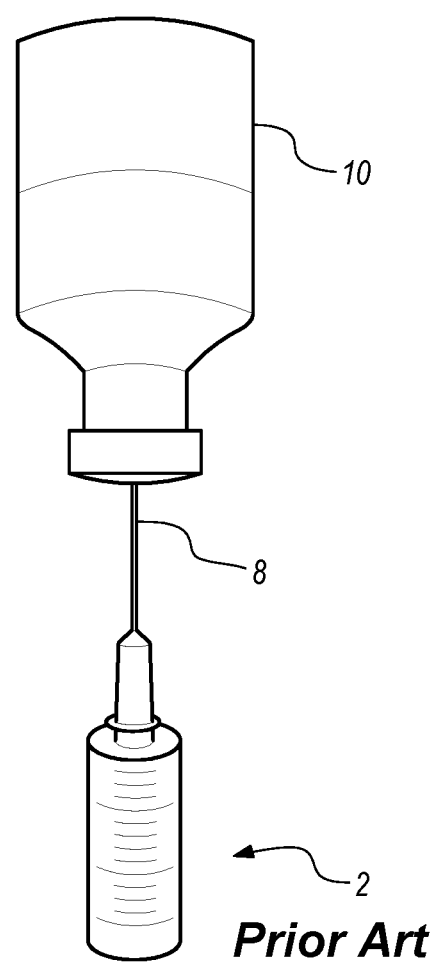
Figure 2A:
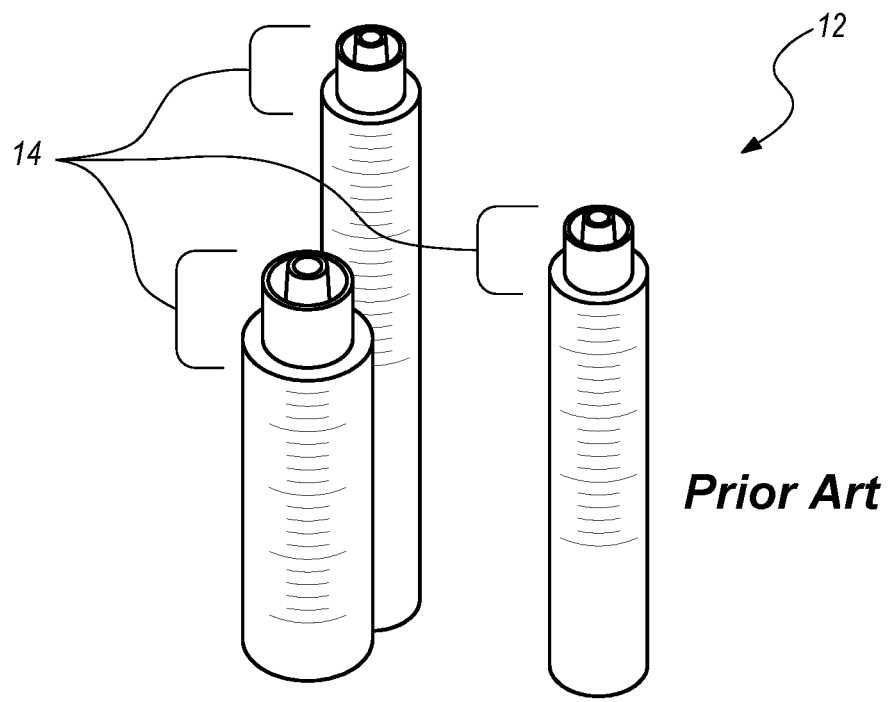
Figure 2B:
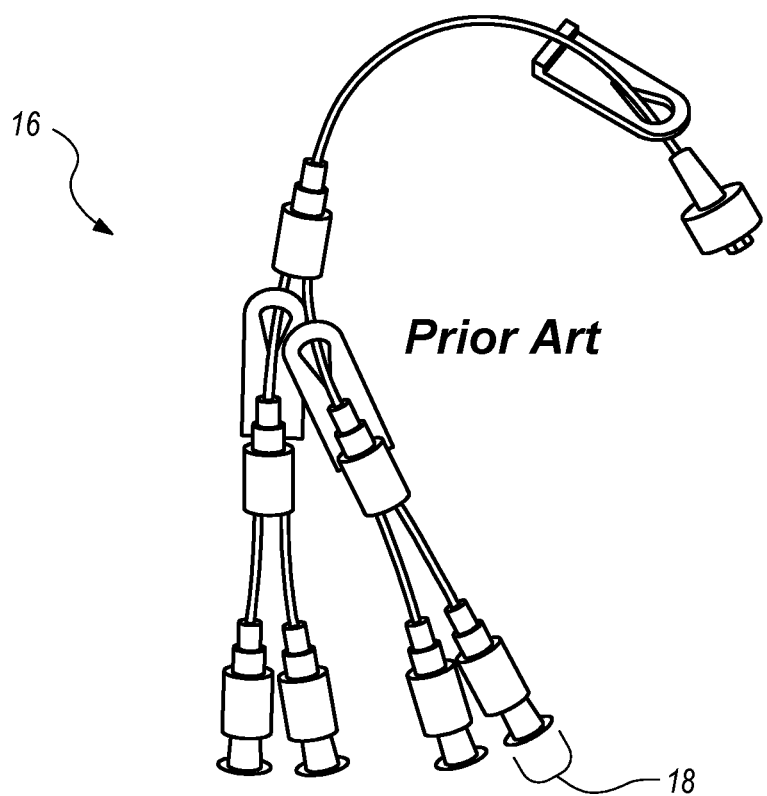
Figure 3:
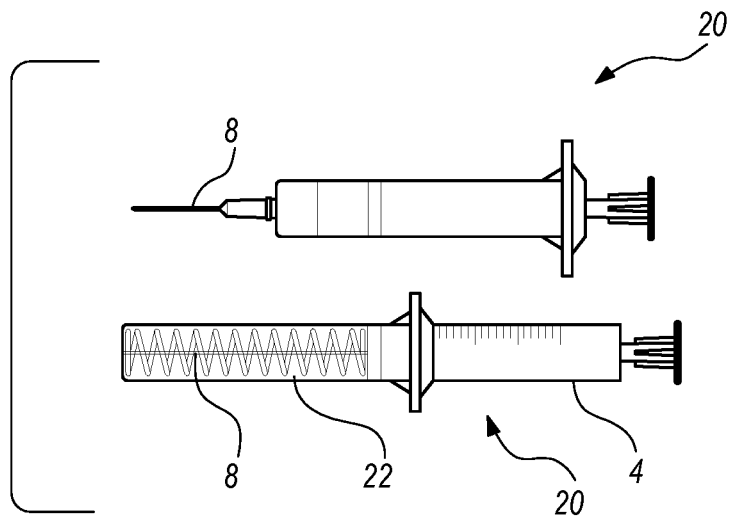
Figure 4A:
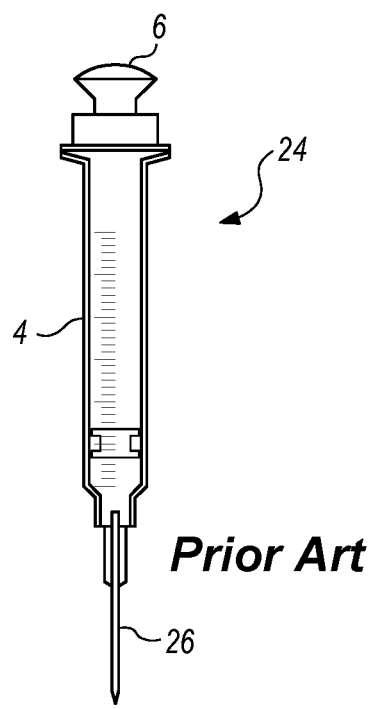
Figure 4B:
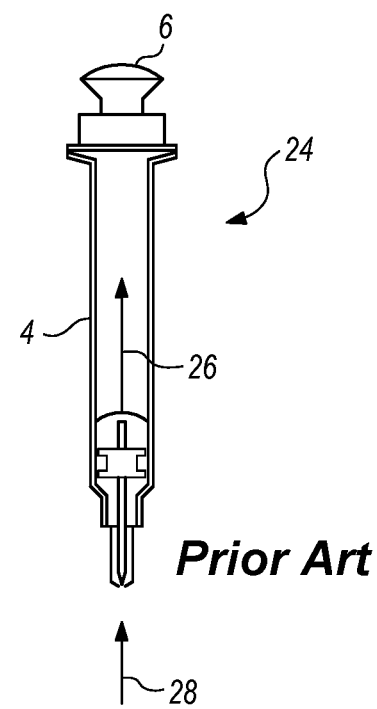

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Safe Syringe Systems

Referring to FIGS. 6A-6B, a side and a perspective view of a safe injection system are shown, with a conventional off-the-shelf pre-filled syringe body (34) defining a medicine chamber (40), a stopper member (36) occluding the proximal aspect of the medicine chamber (40), and a needle coupling assembly (606) disposed at the distal aspect of the medicine chamber (40) with a needle cover member (63) installed for storage. The safe injection system controls exit of medicine from the chamber (40) distally subject to insertion of a plunger assembly relative to the syringe body (34) by a user. The plunger assembly includes a stopper member (36), a plunger housing member (69) and a plunger manipulation interface (128).

Figure 6C:
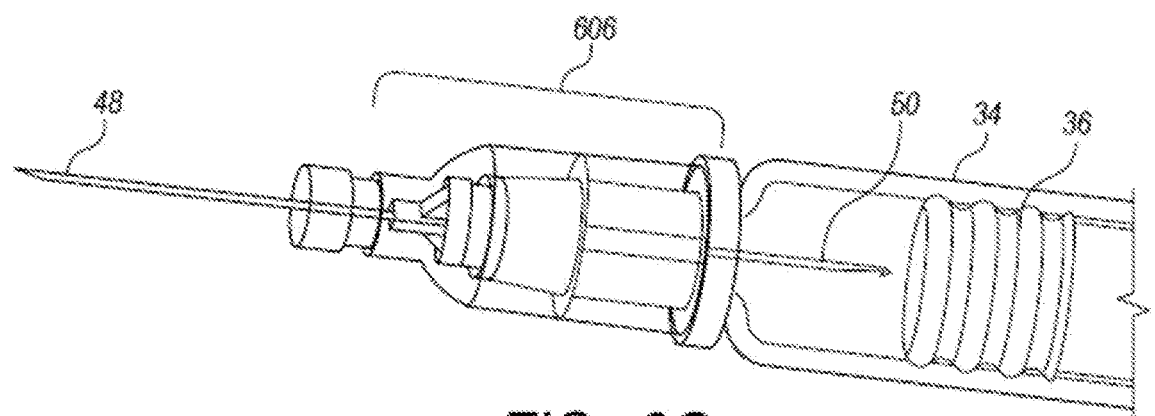
FIGS. 6A-8U illustrate various aspects of safe injection systems wherein a distal needle tip may be withdrawn into a protected configuration after use according to various embodiments.
Figure 6D:
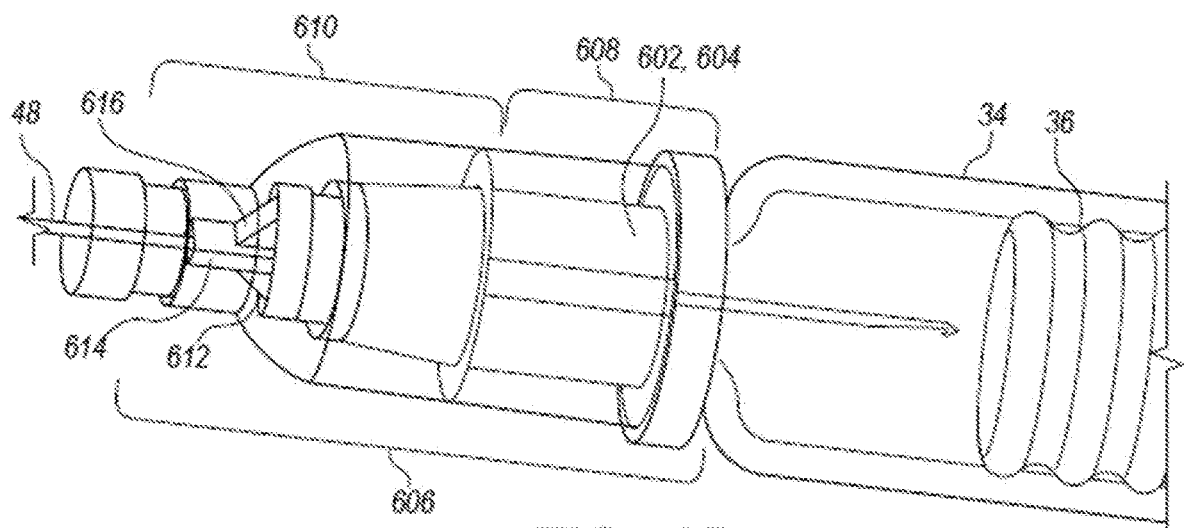

Referring to FIG. 6C-6D the safe injection system has a staked needle configuration wherein upon presentation to the user, a needle assembly, comprising a needle coupling assembly (606; itself comprising a proximal housing portion (608) and a distal housing portion 610), a needle distal tip (48), a needle joining member (83—see, for example, FIG. 6E), and a needle proximal end (50) are mounted in position ready for injection after removal of a needle cover member (63) which may comprise an elastomeric sealing material on its internal surface to interface with the needle distal tip (48) or the distal housing portion (610) during storage. While, the staked needle is depicted as mounted in position, the staked needle may be removably coupled to the syringe body (34) using a Luer interface (not shown), with the proximal end (50) of the needle member extending through the Luer interface and into the medicine chamber (40). In the embodiments depicted in FIGS. 6A-8U, a significant portion of the safe needle retraction hardware resides within a plunger housing.

Referring to FIGS. 6E and 6F, the needle spine assembly (76) includes an injection member having a distal needle tip (48), and a needle proximal end (50) coupled to a needle joining member (83). The needle joining member (83) is configured to have a necked-down or radially-reduced portion (111) that is configured to interface with a latching member (612) and movable block member (614) such that during injection, the needle distal tip (48), needle joining member (83), and needle proximal end (50) remain fixed in position relative to the syringe body (34), but after complete insertion of the plunger assembly relative to a small diameter flange (33—see, for example, FIG. 6A) (i.e., after full expulsion of the medicine which may be contained within the medicine chamber 40 of the syringe body 34), the movable block member (614) is advanced relative to the distal housing portion (610) such that the plurality (two are illustrated) of cantilevered latch members (616) of the latch member (612) are urged out of the way by the movable block member (614) to allow the needle distal end (48), joining member (83), and proximal end (50) to be retracted through their coupling (as described below), thereby placing the needle distal end (48) safely within the plunger housing member (69). In other words, the cantilevered latch members (616) retain the position of the needle distal end (48) during injection, until they are pushed out of the way by the movable block member (614) during plunger insertion, after which the needle is free to be withdrawn as described below. As depicted in FIGS. 6C, 6D and 6E, the needle spine assembly (76), the needle coupling assembly (606) and the latch member (612) form respective portions of a needle hub assembly.

Figure 6G:
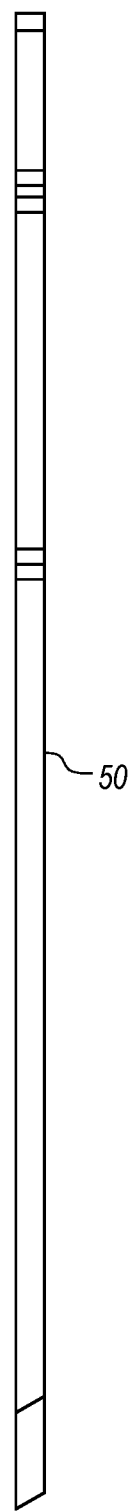
Figure 6H:
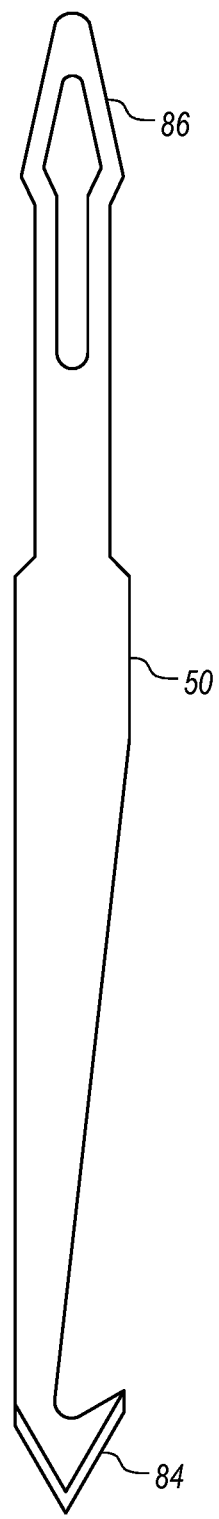
Figure 6I:
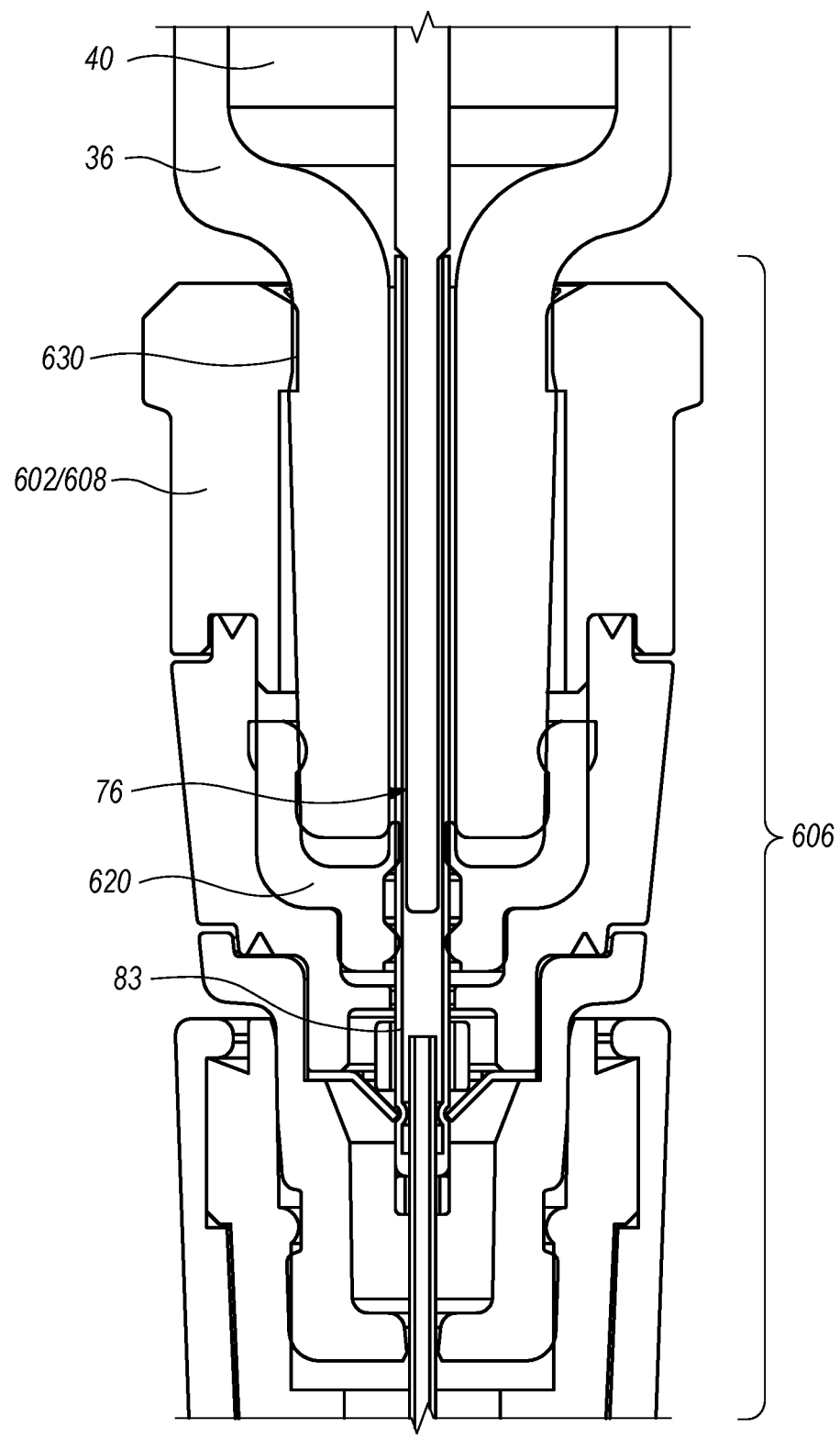
Figure 6M:
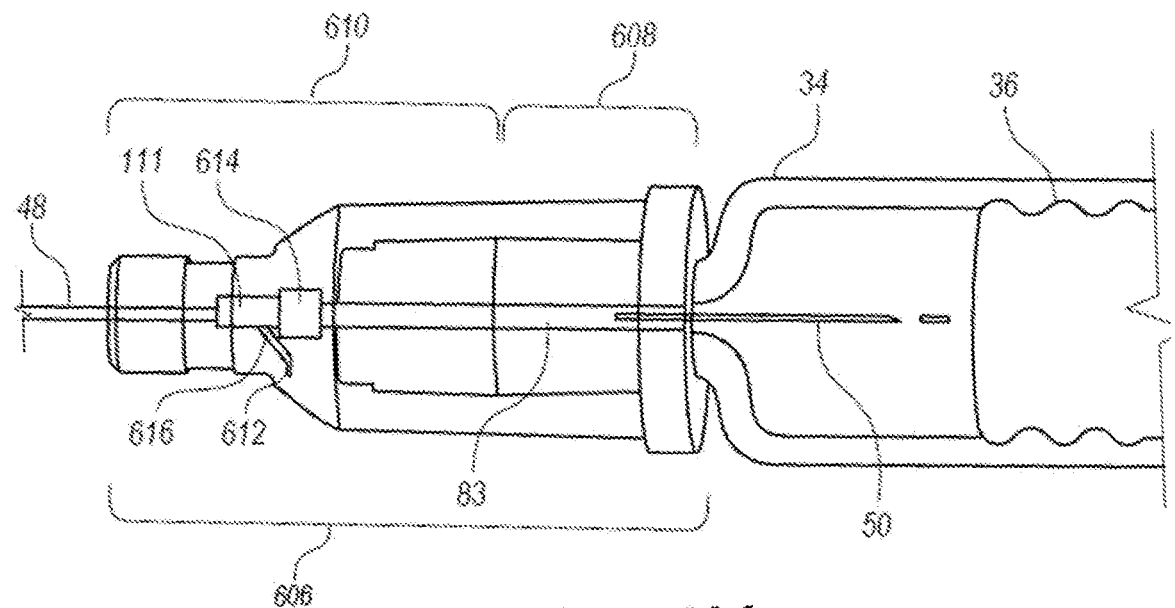
Figure 6N:
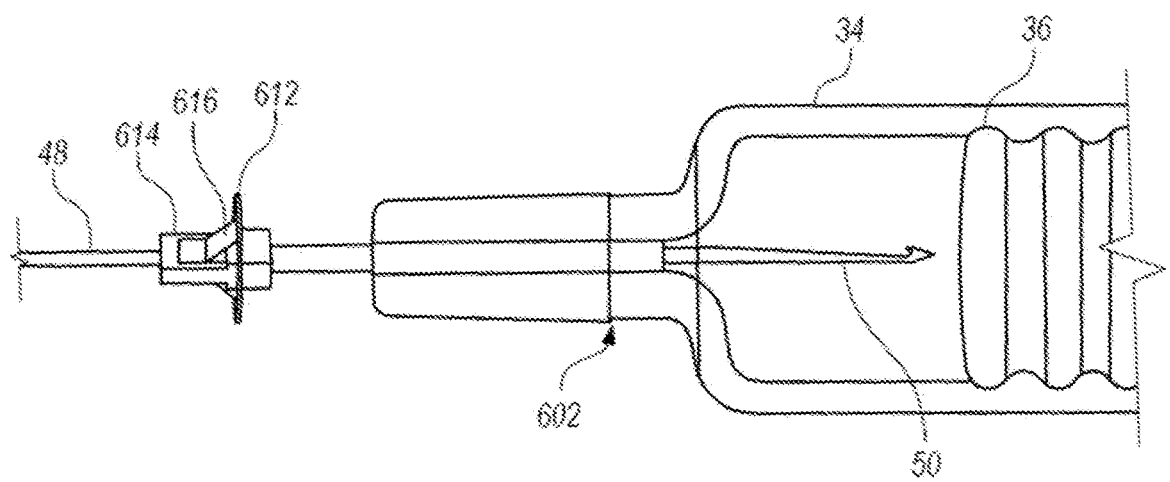
Figure 6O:
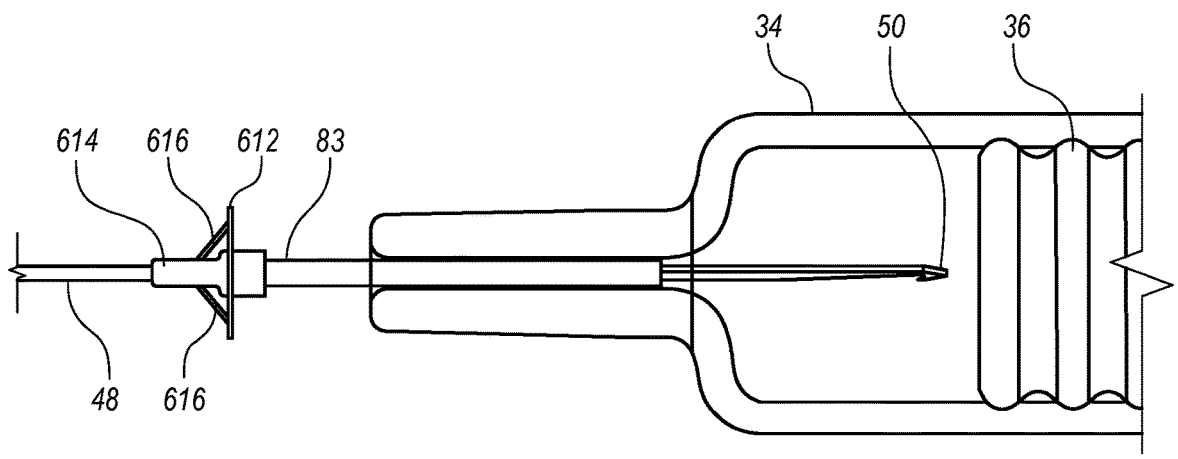
Figure 6P:
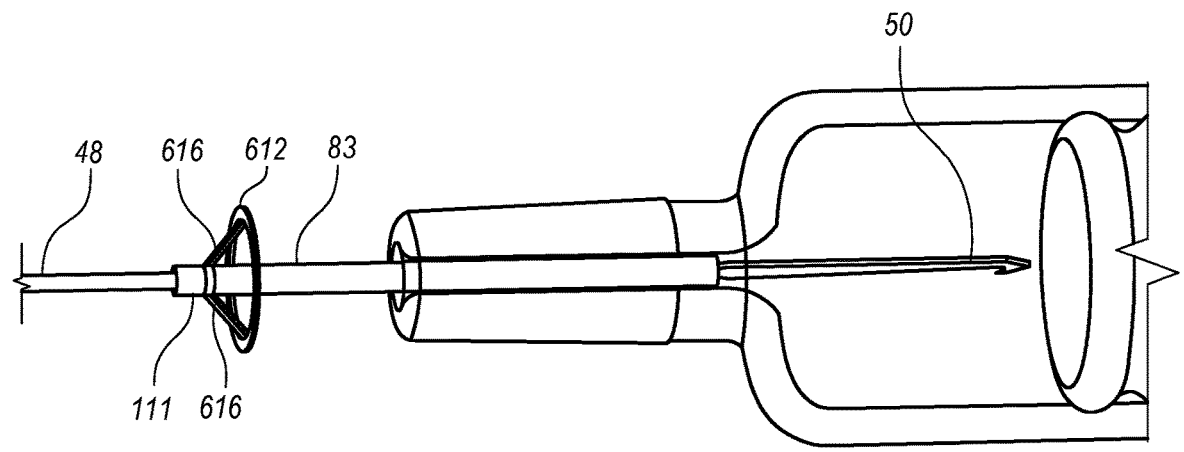

Referring to FIG. 6D, at initial assembly time (i.e., in the factory or processing facility—not in the field in a "staked needle" configuration), the proximal housing portion (608) is configured to snap-fit (i.e., using a snap ring element 604 comprising or coupled to the proximal housing portion (608)) over a slightly recessed radial portion (602) of the syringe body which is formed into the syringe body upon manufacture of the syringe body. FIG. 6I illustrates a cross sectional view of such constructs in action, and FIGS. 6H-6N illustrate partial perspective wireframe views to more directly visualize the latching member (612) and cantilevered members (616) relative to the needle portions (48, 83, 50, 111).

FIG. 6I also illustrates a distal seal (620) configured to provide a seal between the medicine chamber (40) in a medicine container (e.g., syringe body (34)) and the exterior surfaces of the needle spine assembly (76). Preferably, the distal seal (620) is configured to provide a seal around the outside of the needle joining member (83). This seal is further configured to provide a seal between the medicine chamber (40) and the interior surfaces of the needle coupling assembly (606). FIG. 6I also shows a snap fit (630) between a distal end of the medicine container (e.g., syringe body (34)) and a proximal end of the needle coupling assembly (606).

Referring to FIGS. 6J-6L, the distal seal (620) is shown in perspective views (FIGS. 6J-6K) and a cross sectional view (FIG. 6L). The distal seal (620) includes a medicine container contact seal surface (622). This contact seal surface (622) further includes a proximally projecting seal (624) configured to seal against the outside surfaces of the needle spine assembly (76) when the distal seal (620) is coupled to the medicine container (e.g., syringe body (34)) and the needle coupling assembly (606). The distal seal (620) is also includes internal sealing glands (626) to seal on the outside of the needle joining member (83). Moreover, the distal seal (620) includes a needle coupling assembly contract surface (628) configured to seal against an inside surface of the needle coupling assembly (606) when the distal seal (620) is coupled to the needle coupling assembly (606). The distal seal (620) is constructed of an elastomer material, such as butyl rubber, thermoplastic elastomer, silicone, or other material which is compliant to conform to the surfaces of the needle spine assembly (76), distal end of the syringe (34), and/or needle coupling assembly (606).

FIG. 6E illustrates aspects of a needle spine assembly (76), comprising the elements of a needle assembly without the needle coupling assembly (606). The distal portion (48) of the needle spine assembly (76) comprises a sharpened hypodermic needle tip formed on an injection member (78). As shown in FIGS. 6G and 6H, the needle proximal end (50) also comprises a sharpened tip (86) that is formed into a coupling member that forms the distal portion. A hollow joining member (83) couples the coupling member to the tubular injection member (78). The injection member (78), sharpened tip (86) on the needle proximal end (50), and hollow joining member (83) may be held together with interference fits, welds, and/or adhesives. The most proximal end (84) of the needle proximal end (50) in the depicted embodiment comprises a "harpoon" style geometry configured to stab into and hold onto a compliant member to which it may be interfaced, as described in further detail below, for withdrawal of the needle spine assembly (76) into the plunger housing member (69). The needle proximal end (50) may be formed from a thin sheet metal component using laser cutting, etching, stamping, and/or machining techniques, for example.

Returning to FIGS. 6A-6B, for example, a safe injection configuration comprises a conventional syringe body (34), fitted with a plunger tip (36) configured to be pierced by proximal needle end (50) at an appropriate time to assist with needle retraction; this plunger tip (36) is coupled to a plunger manipulation interface (128) by a plunger housing member (69) defining an inner volume occupied by various other portions of the assembly, as described below, which are configured to retract the needle at an appropriate time in the sequence of use. A needle coupling assembly (606) described above is included in the illustrated embodiment; other embodiments may comprise Luer type needle assembly coupling to the syringe body (34). The depicted version of the syringe body (34) comprises a conventional small-diameter flange (33) geometry which may be manipulated or interfaced between the index and middle fingers of the operator, for example, while a thumb of the operator is interfaced with the plunger manipulation interface (128). FIGS. 6A and 6B illustrate pre-utilization assemblies with a needle cover (63) in place to mechanically isolate the distal needle tip (48). Referring to FIG. 6Q, the needle cover (63) has been removed and the assembly is readied for injection into a patient. Referring to FIG. 6R, after the distal needle end (48) has been inserted or stabbed into a tissue structure of a patient, the plunger manipulation interface (128) may be briefly pulled away from the syringe body (34) to "aspirate" or check to confirm that the needle distal tip (48) has not come to rest within an unwanted tissue structure portion, such as a vessel. For example, if the distal needle tip (48) has come to rest within a vessel, upon slightly pulling out the plunger tip (36), a small marking of blood of the patient is likely to appear within the medicine chamber (40), and the operator can see this and reposition the distal needle tip (48).

Figure 6U:
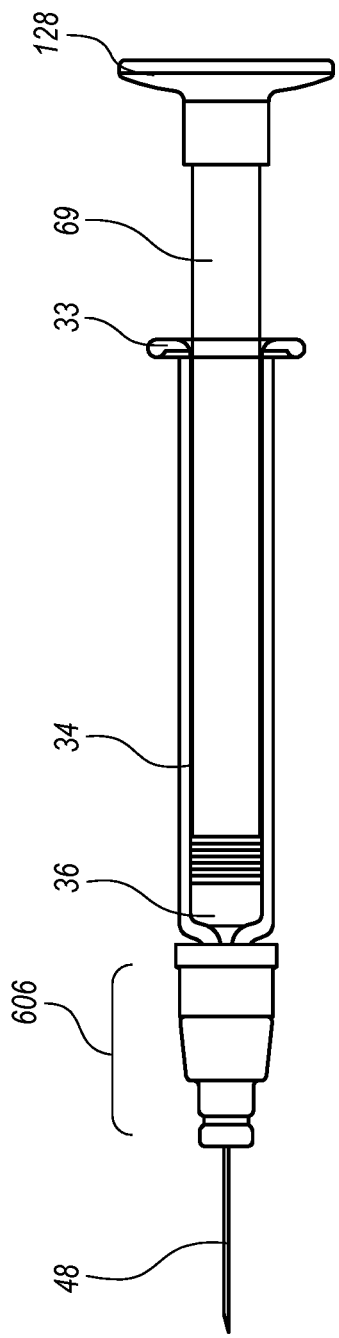
Figure 6V:
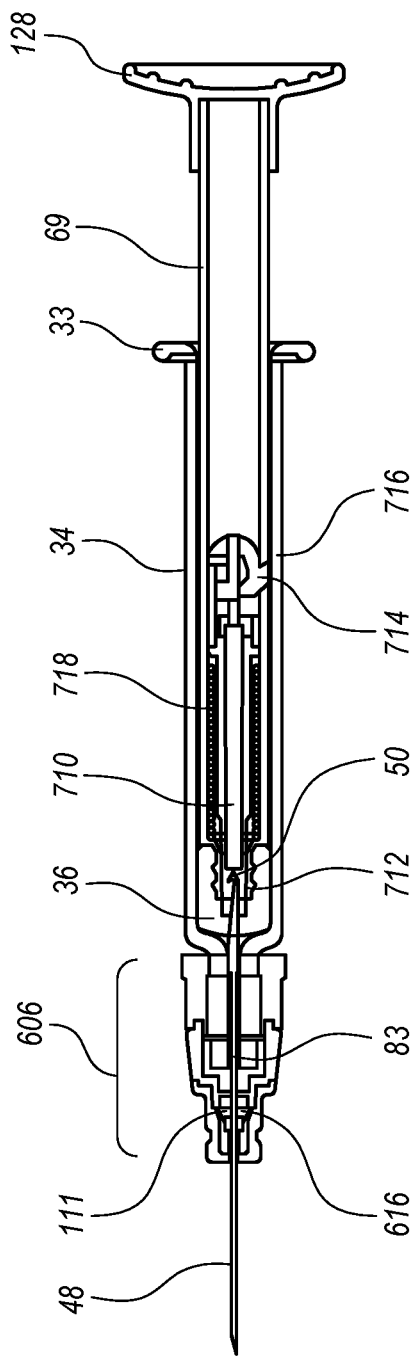

Referring to FIG. 6S, with the desired distal needle tip position confirmed, the plunger manipulation interface (128) is inserted relative to the syringe body (34) and the medicine is expelled out of the medicine chamber (40), through the needle tip (48), and into the patient. FIG. 6T illustrates a cross sectional view of the configuration of FIG. 6S. Referring to FIG. 6U, with complete seating of the plunger tip (36) into the syringe body (34), the proximal needle end (50) is stabbed through the plunger tip (36), while elastic deformation of the material comprising the plunger tip (36) allows the plunger tip to reach the bottom of the syringe body to expel all of the medicine, and trigger the spring to retract the needle while accounting for geometric variation of syringe body and other components due to manufacturing and assembly tolerances. Referring to FIG. 6V, the needle retention feature (712) is configured to prevent pull-out of the proximal needle end (50) once it has been stabbed into and captured by the needle retention feature (712). The capturing interaction between the needle retention feature (712) and the proximal end harpoon (84) of the needle proximal end (50) is configured to allow relatively easy motion (using less force) in the compressive/coupling direction (i.e., during the stabbing-in motion with the proximal end harpoon 84 of the needle proximal end 50), and relatively difficult motion (withstanding more force) in the axial tension/decoupling motion (i.e., with a needle retracting load from the plunger assembly to pull the needle distal tip into a safe configuration).

Figure 5A:
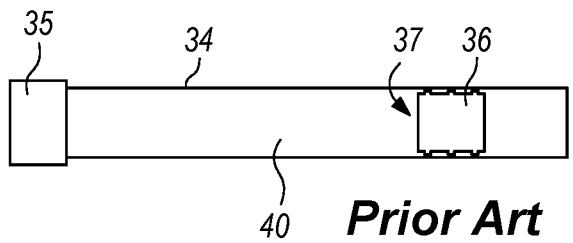
Figure 5B:
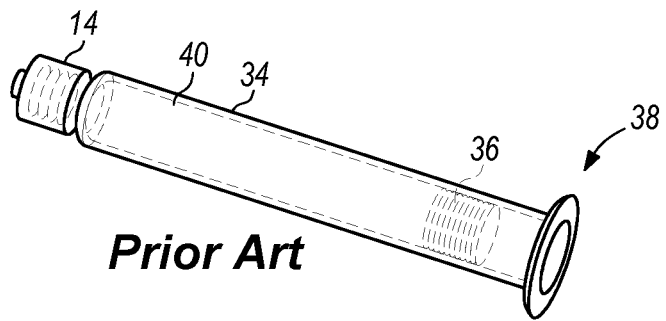
Figure 5C:
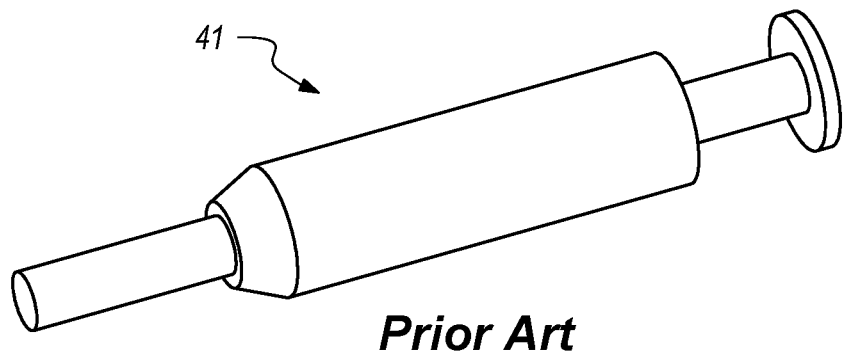

With insertion of the plunger tip (36), the needle latch (616) is configured to become unseated from its previous interface position (111) against the needle body, as shown in FIG. 6V, to allow for retraction of the needle; concomitantly, as is shown in the progression from FIGS. 6U/6V to FIGS. 6W/6X, the proximal needle end (50) is configured to directly abut or compress against an unlatching member (710) or rod that is configured to allow a rotatable latching member (714) to be positioned or configured into either of two states. The first configuration of the rotatable latching member (714), shown in FIG. 6U and associated cross section FIG. 6V, is the "latched" condition, where the rotatable latching member (714) is retained in the position shown in FIG. 6V by a proximal feature comprising the proximal aspect of the unlatching member (710). In this latched condition, a load generated by a compressed energy-storing member (718), such as a spring, is reacted by the geometric state of the latching member (714), maintaining the compressed state of the energy-storing member (718). The second configuration of the rotatable latching member (714), shown in FIG. 6W and associated cross section FIG. 6X, may be termed the "unlatched" condition wherein the unlatching member (710) has been moved more proximally with loading from the needle proximal end (50) to cause the rotatable latching member (714) to be free to rotate. In this second configuration, with rotation of the rotatable latching member (714) out of the lock interface window (716) as shown in FIG. 6X, the load generated by the compressed energy-storing member (718) is not reacted by the rotatable latching member (714), and the energy-storing member (718) is free to expand longitudinally, as shown in FIG. 6Y and associated cross section FIG. 6Z, thereby pulling the needle retention feature (712) and intercoupled needle spine assembly (76) proximally, which retracts the needle spine assembly (76) through the plunger tip (36) where the needle distal tip (48) is safely encapsulated in at least a portion of the plunger housing member (69) and/or inside at least a portion of the needle coupling assembly (606) and/or recessed below the distal end (37 in FIG. 5A) of the plunger tip (36). As such, the rotatable latching member (714) is a "living hinge". Thus referring to FIG. 6X, in the unlatched configuration, the unlatching member (710) is moved proximally and the rotatable latching member (714) is configured to rotate from a latched position, wherein the rotatable latching member (714) is seated within a lock interface window (716), and wherein this interfacing of the latch position maintains the energy storage member (718), which may comprise a spring, in a stored configuration, to an unlatched position, wherein the rotatable latching member (714) is rotated slightly out of the lock interface window, as shown in FIG. 6W, and the cross sectional view of FIG. 6X, to free the energy storage member (718) to accelerate and move the unlatching member (710) and intercoupled retention features (712) to the right as the potential energy stored in the energy storage member (718) is released, thereby pulling the intercoupled proximal needle end (50) along with it, as shown in FIG. 6Y and the cross sectional view of FIG. 6Z, such that the needle distal tip (48) becomes safely encapsulated within the plunger tip (36) and the plunger housing member (69) (i.e., into a protected configuration). Once in this configuration, the needle coupling assembly (606) preferably is configured to prevent any further re-insertion of the distal needle tip (48) relative to the syringe body (34); in other words, needle tip re-exposure is prevented with such a safety configuration. In one embodiment the plunger tip (36) may be solid, not having any pre-formed through-holes to facilitate transection of the needle proximal end (50). As shown, for example, in FIG. 6Z, complete retraction of the needle through the plunger tip (36) requires the needle to penetrate the plunger tip. To pull the needle through the plunger tip (36) without losing "grip" on the needle proximal end (50), the penetration force of the needle through the plunger tip (36) generally must be low enough so as not to exceed the "gripping load" provided by the interface that has been formed between the proximal needle end (50) and the needle retention features (712) with stabbing of the proximal needle end (50) through the plunger tip (36). With one embodiment, experimentation has shown that the penetration force between the needle spine assembly (76) and the plunger tip (36), or the needle joining member (83) and the plunger tip (36), is between about 1 lb. and about 4 lbs., depending upon the rubber or elastomeric material used to manufacture the plunger tip (36), or the plastic or metal used to manufacture the needle joining member (83). To further minimize resistance as the needle spine assembly (76) is pulled through the elastomeric plunger tip (36), in one embodiment it is desirable to create a chamfered geometry on the proximal geometric aspects of the needle joining member (83).

As was discussed above in reference to FIGS. 6U and 6V, in the embodiment of FIGS. 6A-6Z, the elastomeric material comprising the plunger tip (36) is utilized to assist in dealing with slight geometric tolerances which may be present due to manufacturing, assembly, temperature, or other factors. In use, the operator feels the full insertion position of the plunger tip (36) relative to the syringe body (34) coming by an increased insertion load required to continue inserting the plunger tip (36). The operator may be trained to continue such insertion against such increasing insertion resistance load until a "click" sound is heard, which signifies that the needle latching mechanism (616) has been triggered, thereby releasing the needle longitudinally relative to the syringe body (34) so that it may be retracted. In one embodiment, the "click" sound is caused by rotation of the rotatable latching member (714), which is driven by the energy storage member (718).

Figure 7E:
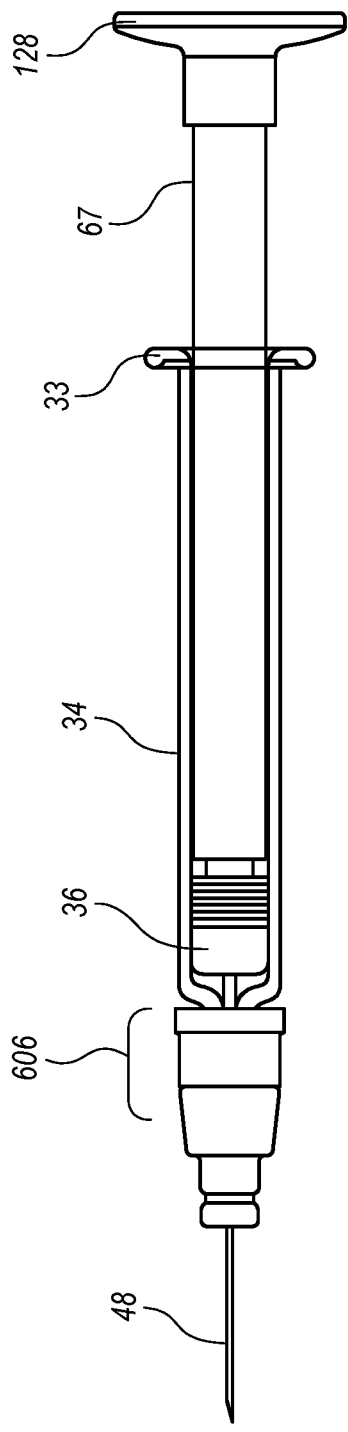
Figure 7F:
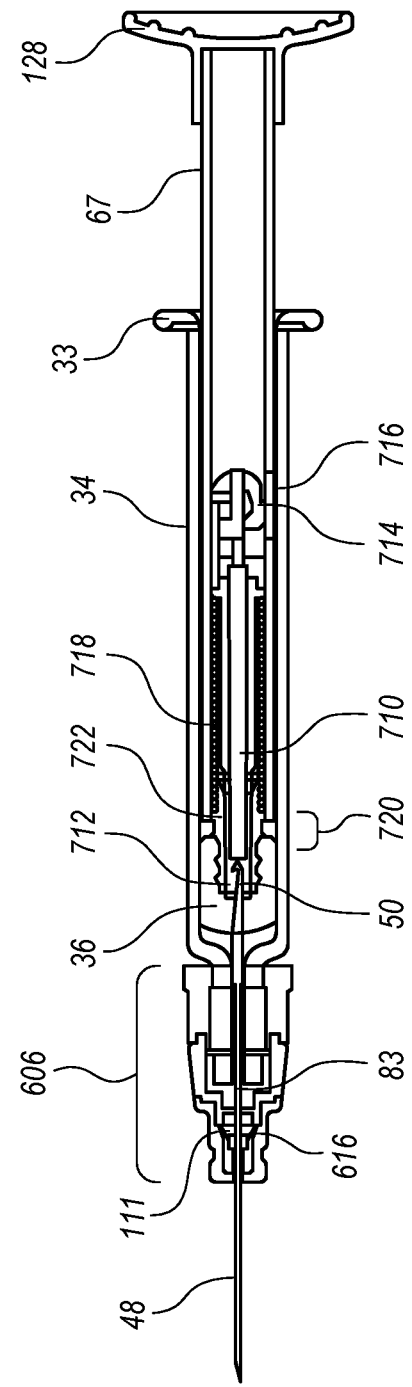
Figure 7I:
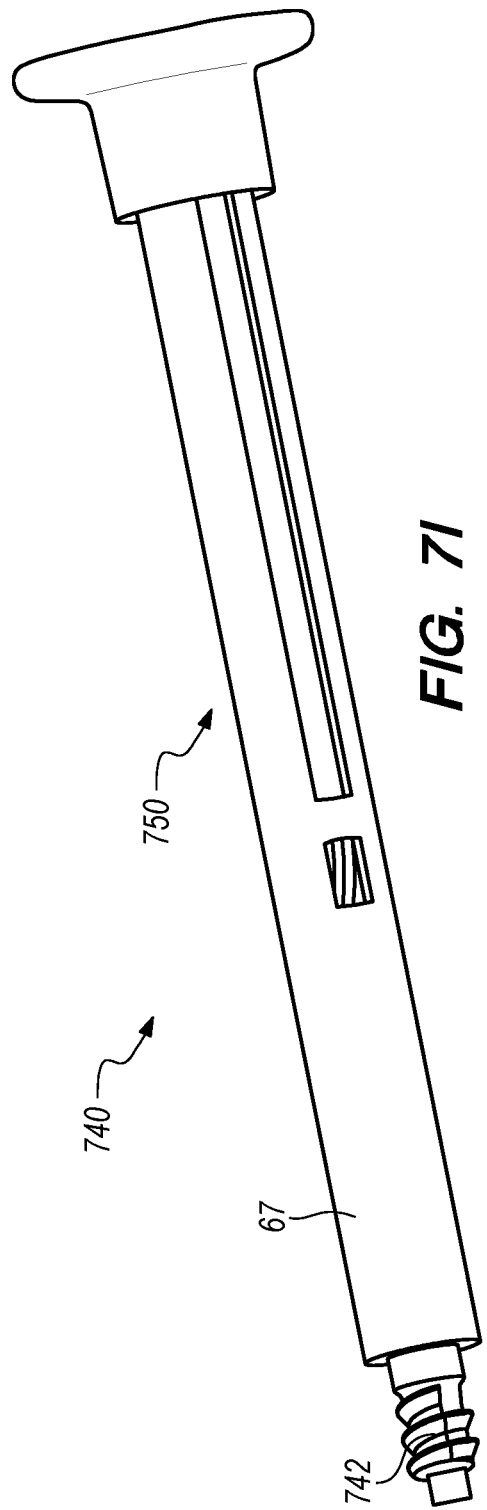
Figure 7J:
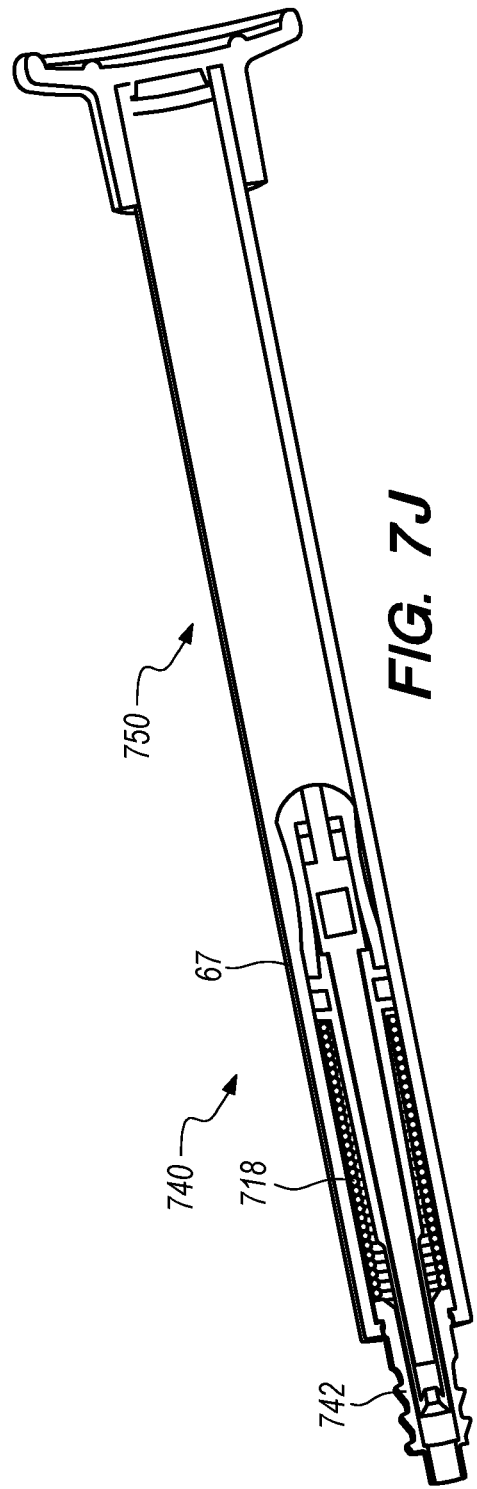
Figure 7K:
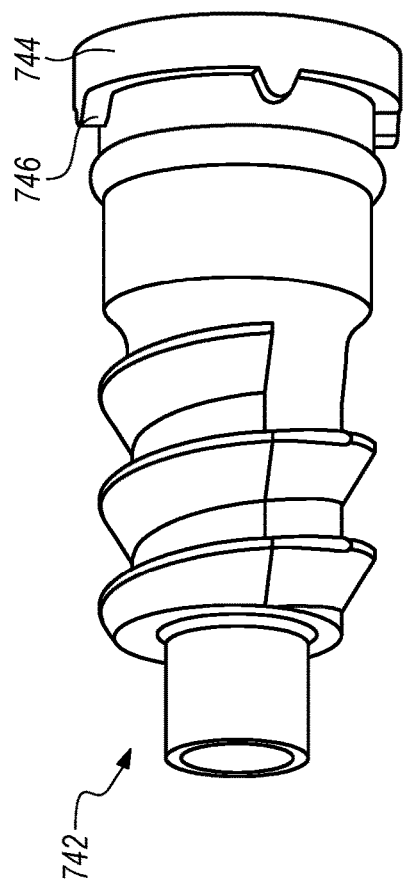
Figure 7L:
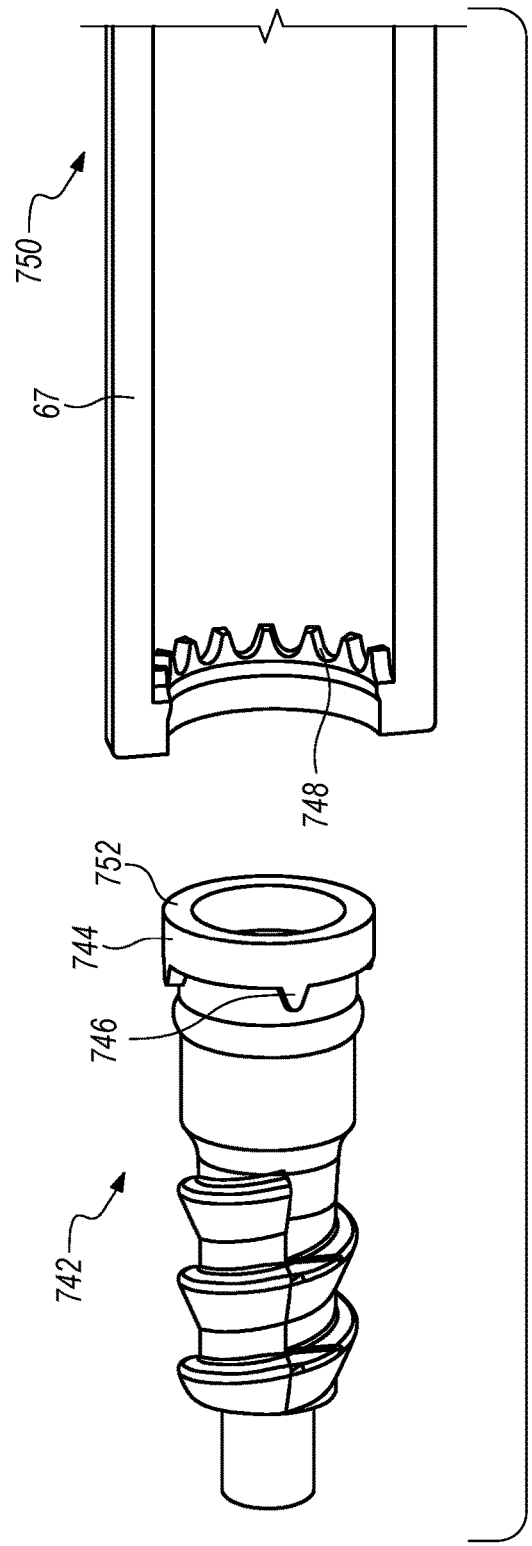
Figure 7O:
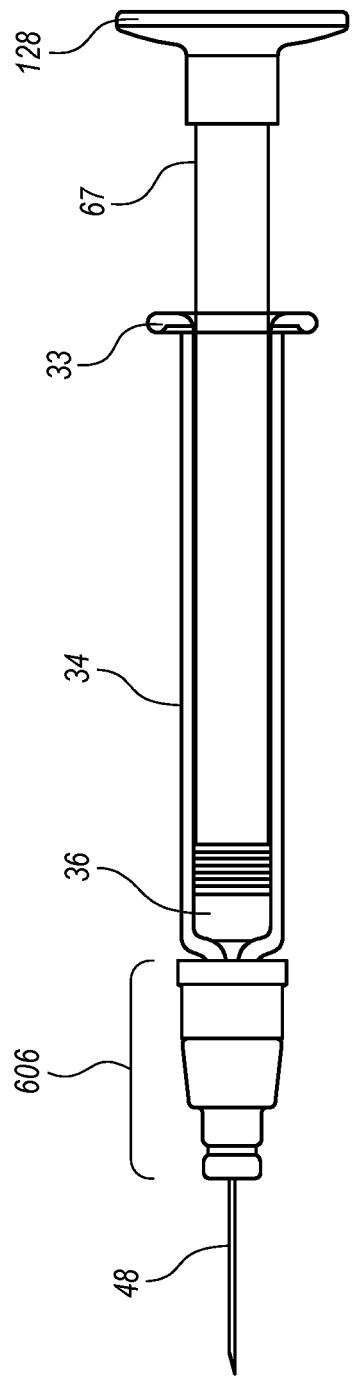
Figure 7P:
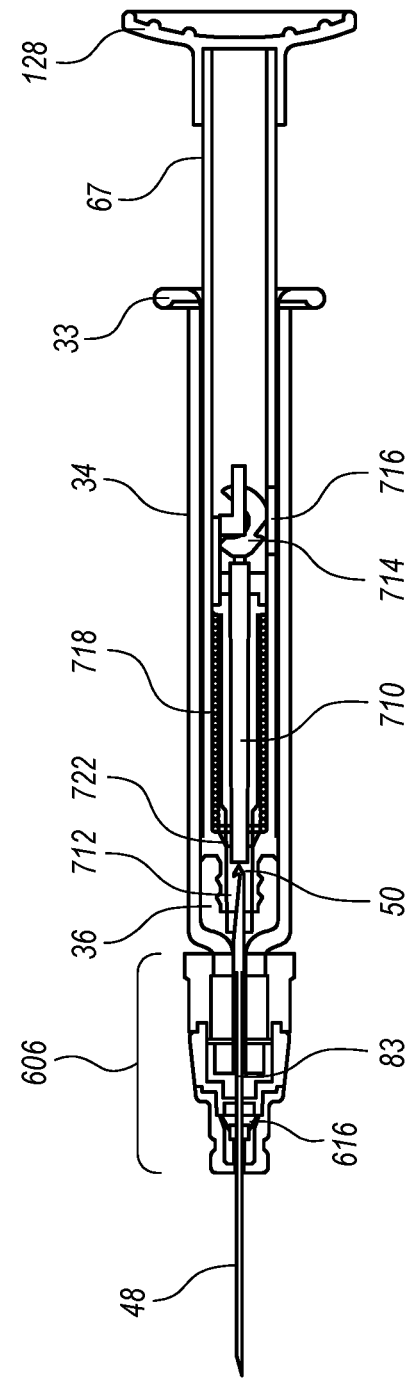
Figure 7Q:
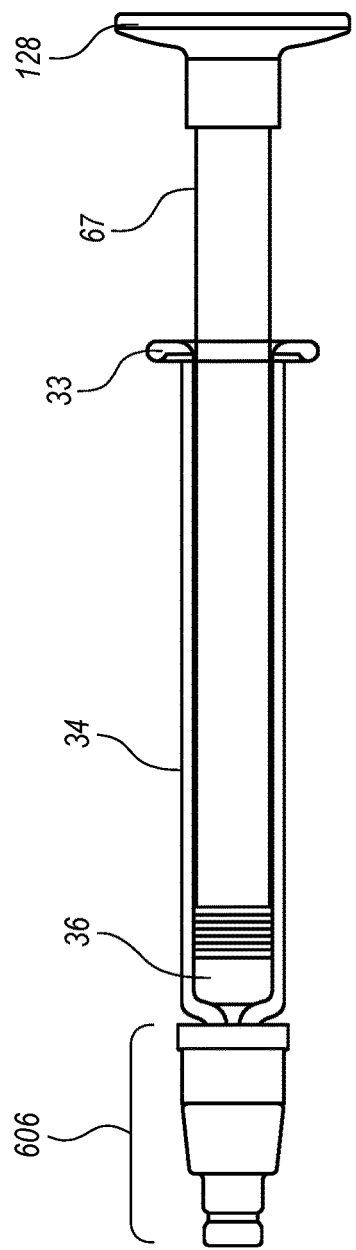
Figure 7R:
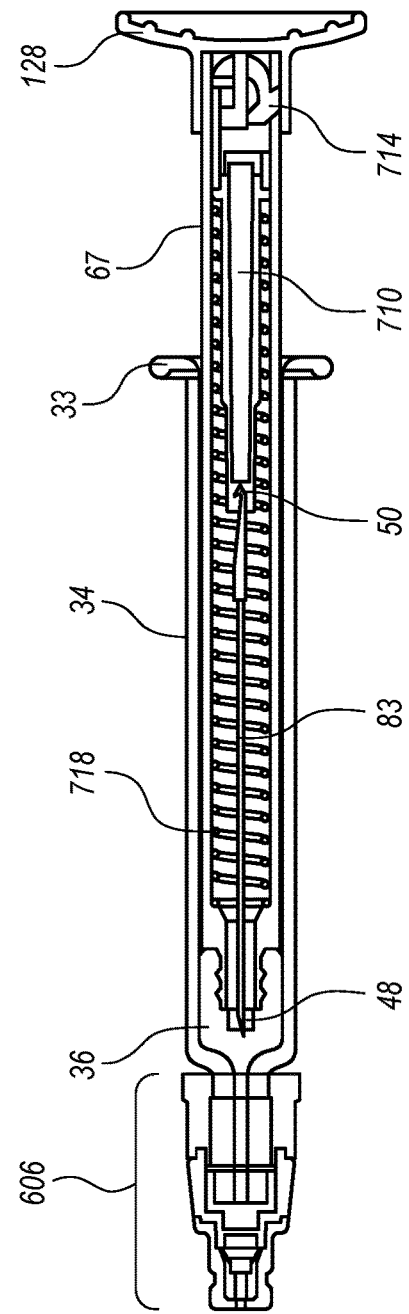

Referring to the embodiment of FIGS. 7A-7R, rather than solely relying upon the elastomeric compliance of the plunger tip (36) for such geometric tolerance accommodation, a coupling member (722) may be movably intercoupled between the plunger tip (36) and the plunger housing (67) such that a gap (720, as shown, for example, in FIG. 7F) is retained until a certain insertional load is obtained, after which this gap (720) is closed by virtue of the proximal end of the coupling member (722) sliding to the right relative to plunger housing (67), to eliminate the gap, as shown in FIG. 7G and associated cross sectional view, FIG. 7H. FIGS. 7A and 7B illustrate such an injection assembly ready to use with a protective cap (63) isolating the distal needle tip (48). FIG. 7C illustrates the protective cap (63) removed, ready for injection. FIG. 7D illustrates an aspiration step, as described above, wherein the plunger may be pulled backwards relative to the patient to confirm needle location.

Thus in operation, upon full insertion of the plunger tip (36) relative to the syringe body (34), several things happen: the needle latching (616) mechanism becomes unlatched, allowing for retraction of the needle; the insertional load threshold is passed, causing the coupling member (722) to collapse the gap (720) and allow for full capture of the needle proximal end (50) by the needle retention features (712), and compressive loads from the needle proximal end (50) abutting the unlatching member (710) cause the rotatable latching member (714) to be free to rotate out of the latched position relative to the lock interface window (716) defined into the plunger housing member (67), as shown in FIG. 7O and associated cross sectional view FIG. 7P;

Referring to FIG. 7I-7L the plunger assembly (740) includes a plunger screw (742) partially housed within the plunger housing member (67). The plunger screw may be configured to be the coupling member (722) and to provide the gap (720) between the stopper (36) and the plunger housing (67) The plunger screw (742) is configured to be coupled to a plunger rod (750) such that the two components are not allowed to rotate relative to one another (i.e., rotationally coupled) when the plunger assembly (740) is in its latched configuration. This rotational lock allows the plunger assembly (740) to be inserted into the stopper member (36) by using a screwing-in motion. Alternatively the plunger assembly (740) can be configured to be inserted into the stopper member (36) via a push-in method.

The plunger screw (742) is configured to be inserted through the plunger rod (750) and forced distally, forcing the intercoupling of the rotational lock by the energy storage member (718) and the intercoupled latch. Additionally, the rotational lock can be configured to slip at a predetermined rotational force (torque) by modulating the projection geometries and axial force applied by the energy storage member (718) to allow rotational slipping at a predetermined torque to prevent over-insertion of the plunger assembly (740) into the stopper member (36). This over-insertion protection is configured to prevent plunger assembly (740) rotation during insertion of the plunger assembly (740) into the stopper member (36). Essentially, the plunger screw (742) is inserted into the plunger rod (750), and the two are rotationally locked together so that the plunger assembly (740) can be screwed into the stopper member (36).

Referring to FIGS. 7K-7L, the plunger screw (742) is configured with a proximal flange (744) and distally projecting features (746) configured to engage with matching proximally facing projections (748) on the inside of the plunger rod (750). These proximally and distally facing features (748, 746) intercouple the plunger rod (750) and the plunger screw (742) components to prevent rotation during the intercoupling of the plunger assembly (740) into the stopper member (36). The plunger screw (742) also includes a proximally facing surface (752) configured to provide a bearing surface to interface with the energy storage member (718)

Referring to FIGS. 7M-7N the plunger screw (742) may further include an axial detent (754) configured to connect to the plunger housing member (67). This axial detent (754) is an external radial protrusion on the plunger screw (742), which interferes with an internal radial protrusion (756) on the plunger housing member (67). The interference between the external and internal radial protrusions (754) (756) is configured to be overcome when a predetermined amount of force is applied to the plunger rod (750) and reacted by the bottom of the syringe medicine chamber (40) (see FIG. 7N).

The amount of force required to overcome the interference between the axial detent (754) and the internal radial protrusion (756) is also configured to be higher than the amount of force required to deliver medicine through the needle. The interference fit is configured such that even viscous medicines can be delivered through the internal diameter passage of the needle spine assembly (76; FIG. 6E) without overcoming the interference fit. As such, the axial detent (754) prevents premature telescoping of the plunger rod (750) due to back pressure of the fluid onto the plunger rod (75) during injection. Once the stopper member (36) reaches the bottom of the syringe body (38) interference from the axial detent (754) is overcome by pressure from the user's finger, and the needle can be triggered to retract.

FIG. 7Q and associated cross sectional view FIG. 7R illustrate the condition of the assembly after the needle has been retracted such that the distal needle tip (48) is housed within the plunger housing member (67) and the plunger tip (36) (i.e., into a protected configuration).

Exemplary Reusable Safe Injection Systems

Figure 8C:
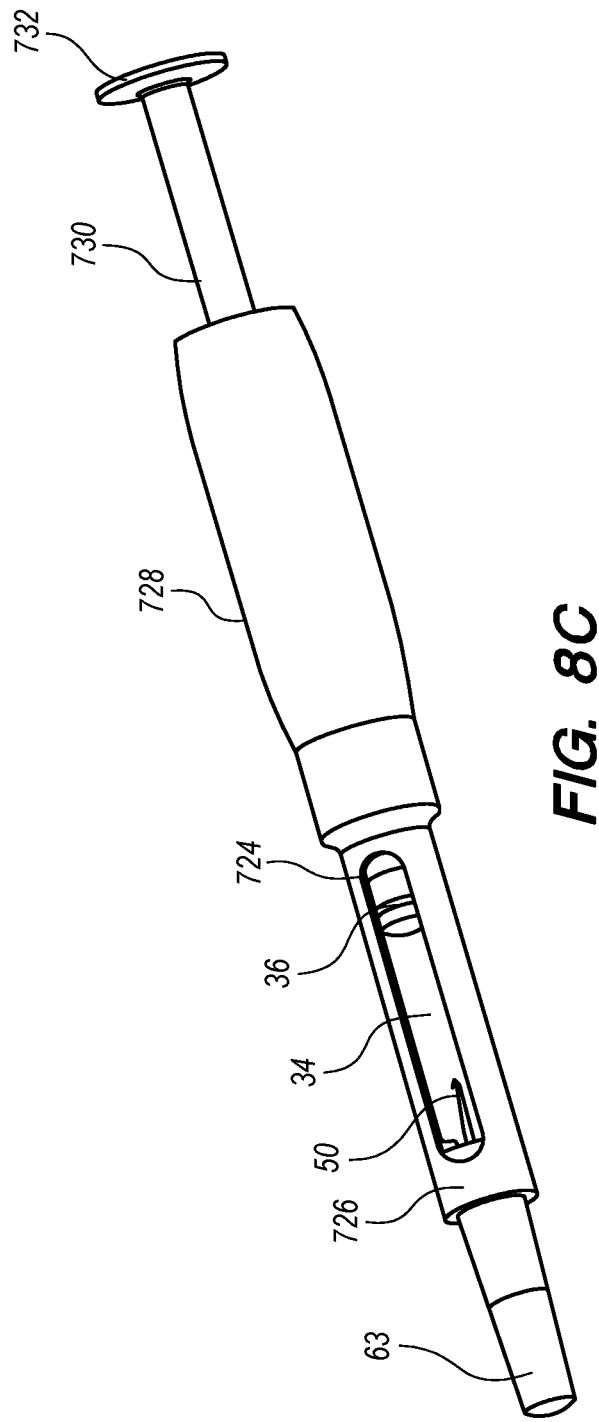
Figure 8D:
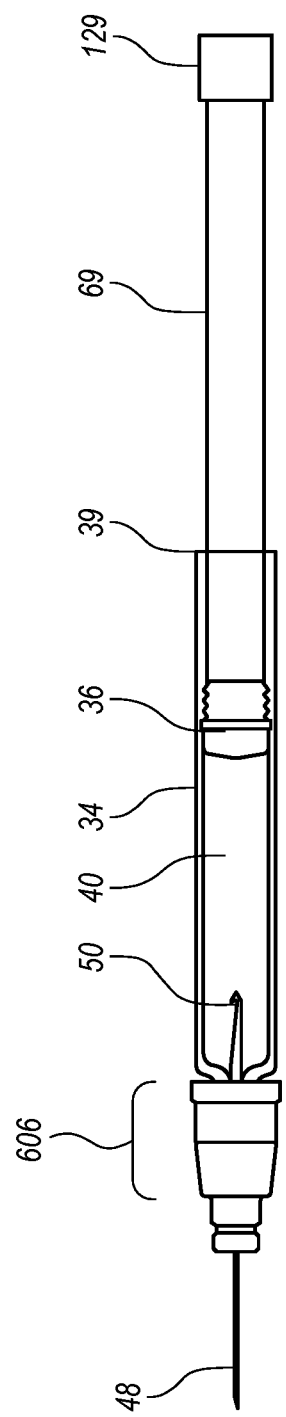
Figure 8E:
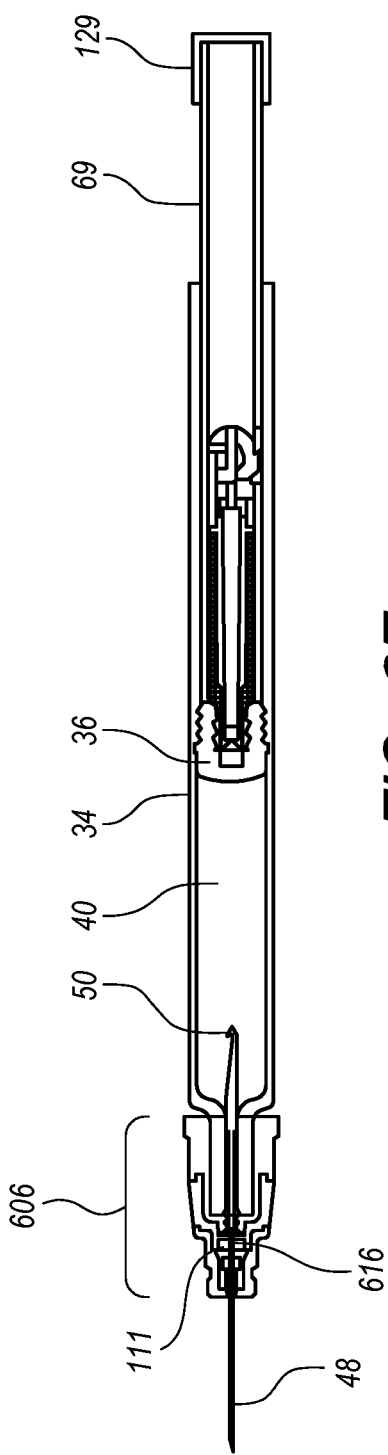
Figure 8F:
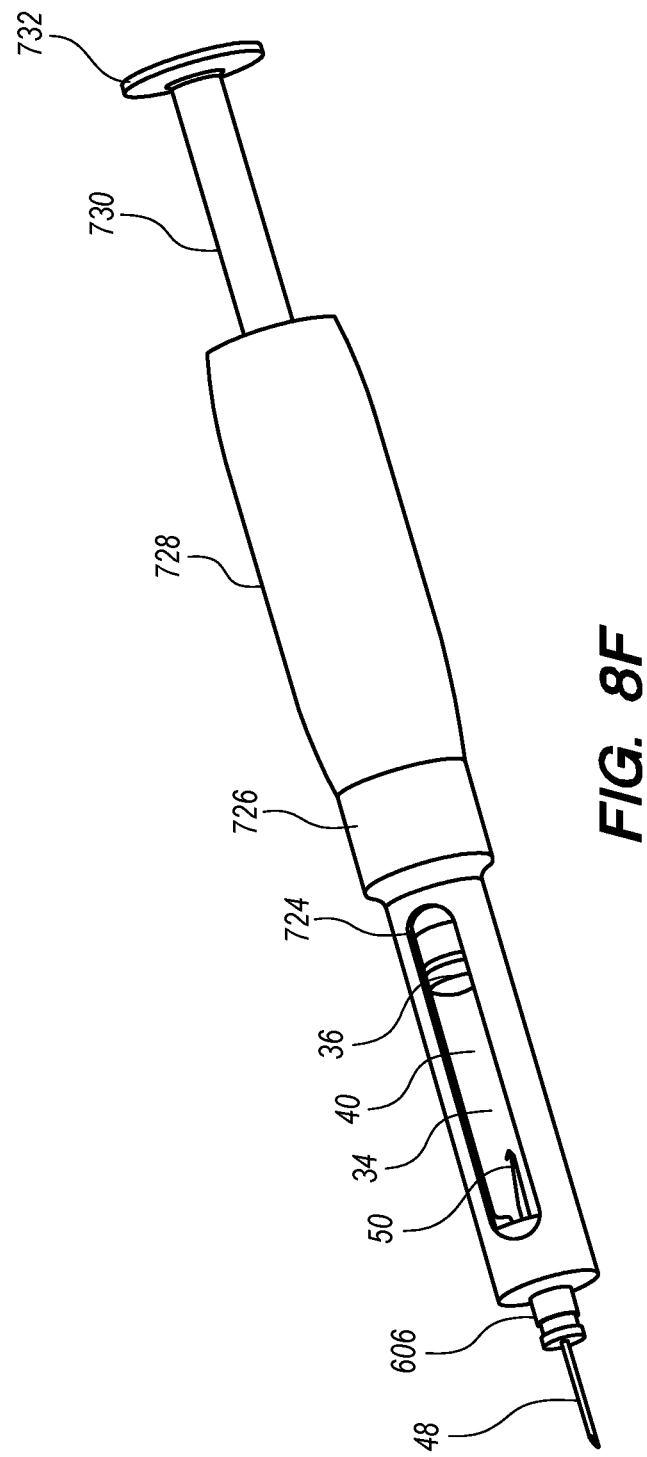
Figure 8I:
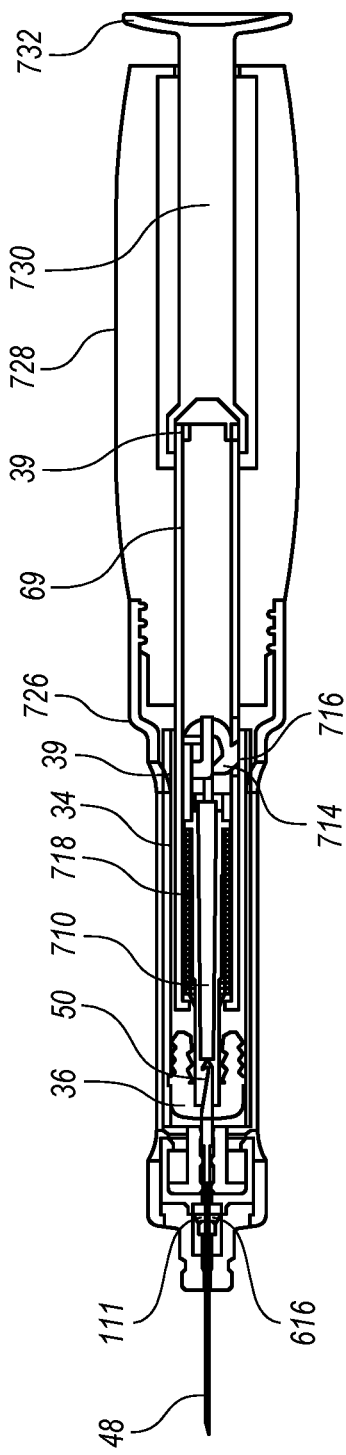
Figure 8J:
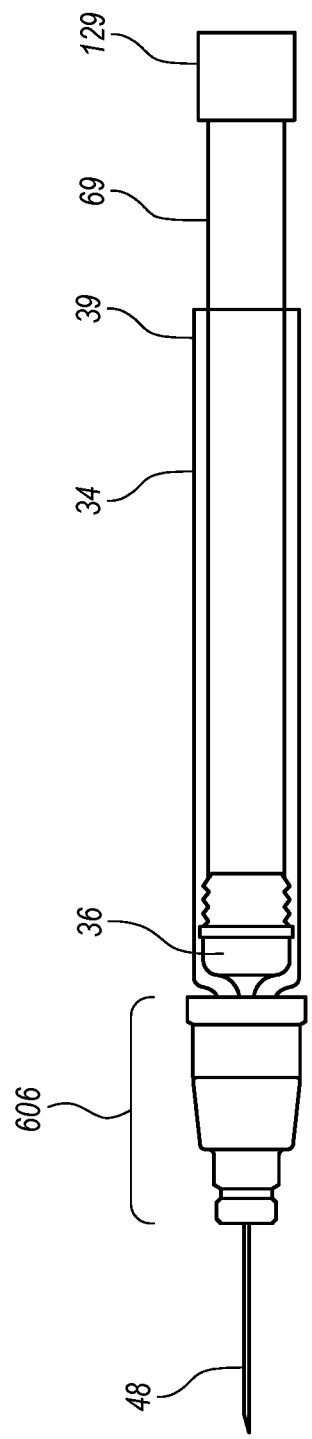
Figure 8Q:
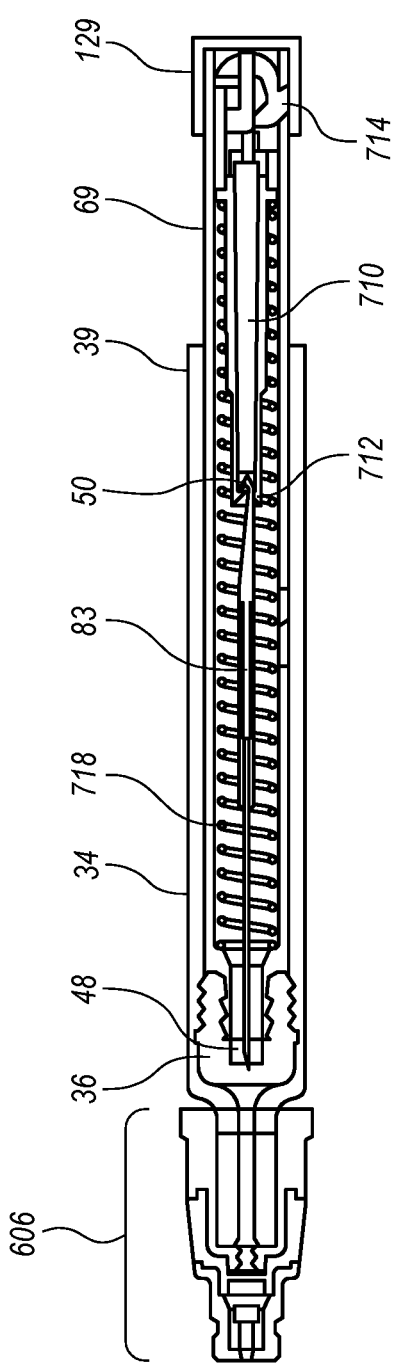
Figure 8R:
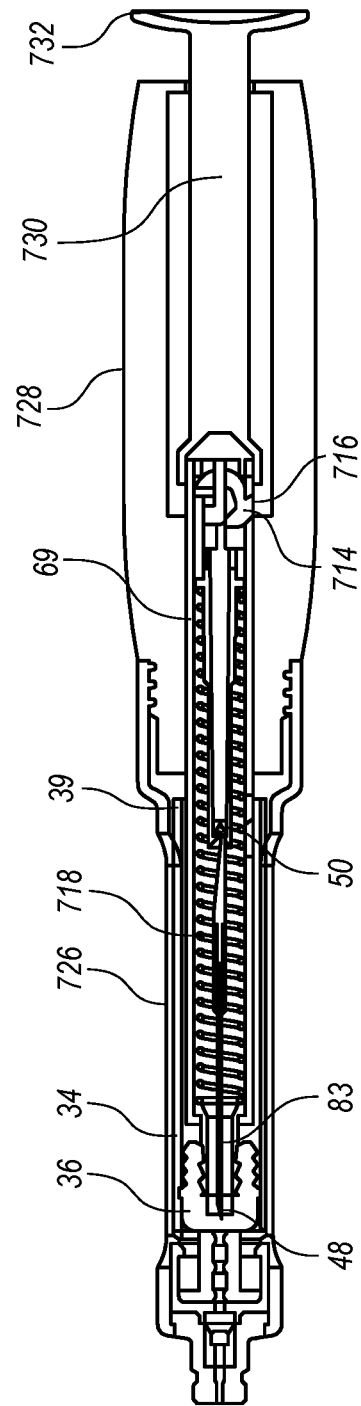
Figure 8T:
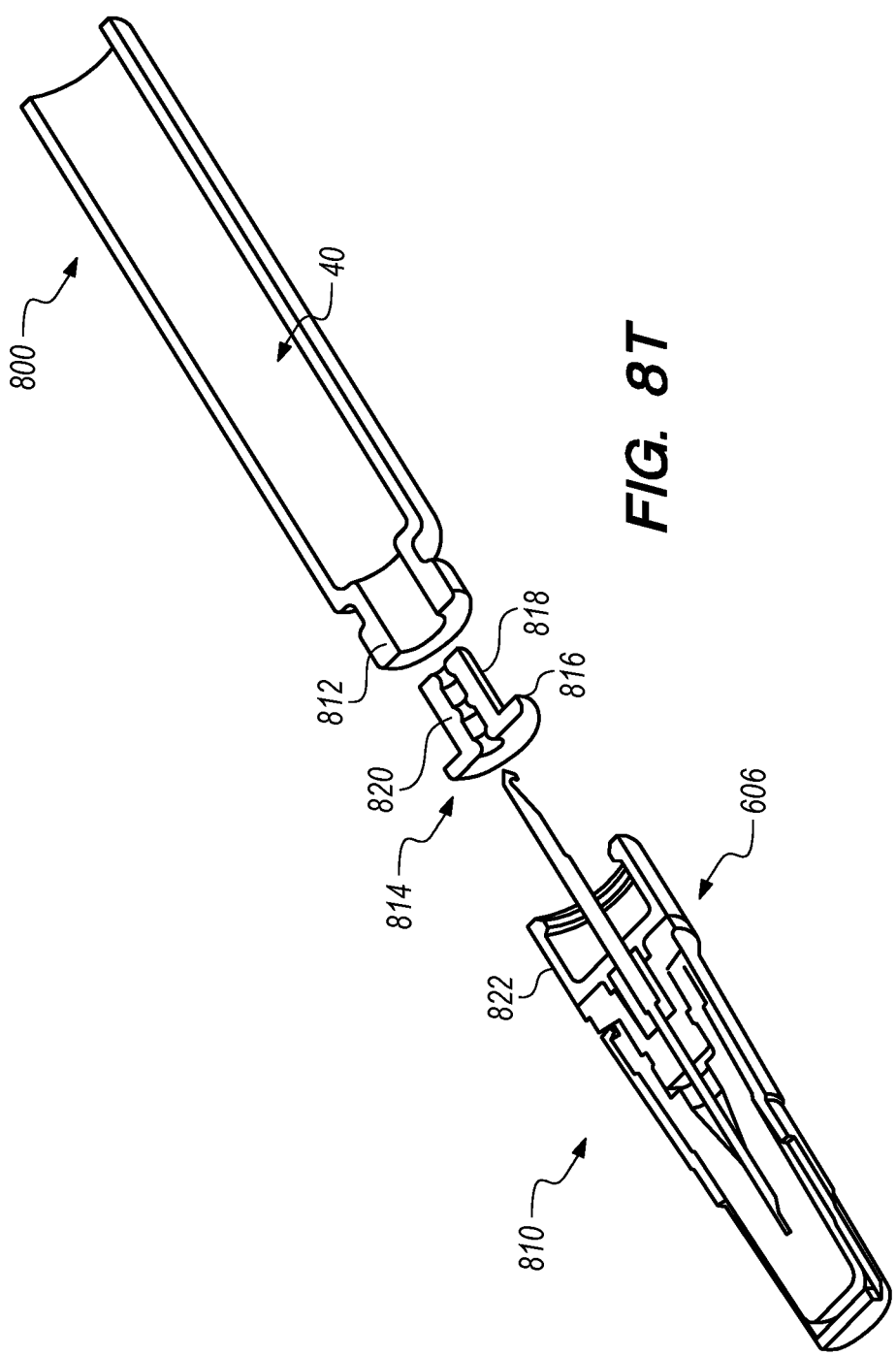
Figure 8U:
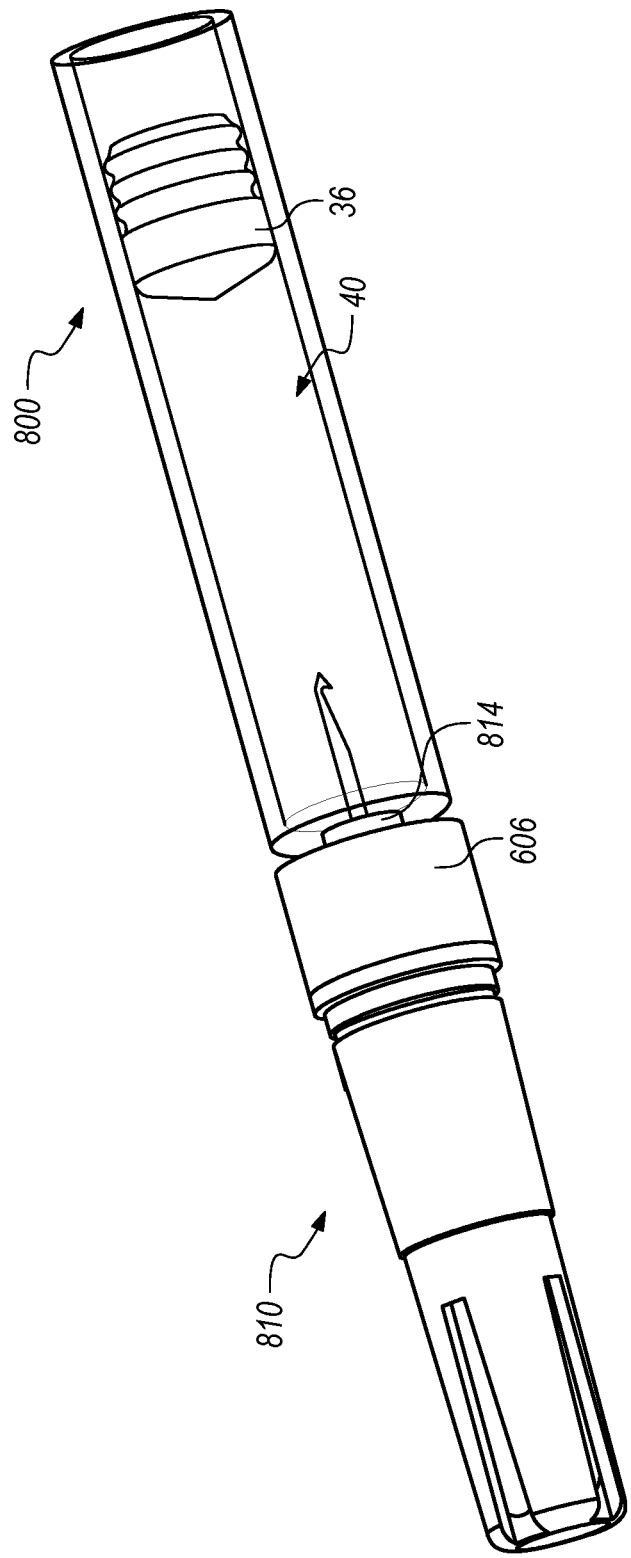

Referring to FIGS. 8A-8U, in another embodiment, configurations similar to those of FIGS. 6A-6Z, or 7A-7R, but without the syringe body flange (33), may be utilized with "pen", "autoinjector" or other "reusable" or "disposable" housing interfaces, such as those depicted in FIGS. 8C, 8F, 8I, 8L, 8O, and 8R. Referring to FIG. 8A, a safe injection configuration similar to that of FIG. 6A is depicted, with the exceptions that the embodiment of FIG. 8A has a syringe body (34) that does not incorporate a proximal flange (element 33 of FIG. 6A), and has a plunger housing (69) without a manual manipulation interface (element 128 of FIG. 6A)—and rather has a proximal end (129) configured to be interfaced with a plunger coupling member (730) distal end of a pen or autoinjector housing configuration. FIG. 8B illustrates a cross sectional view of the configuration of FIG. 8A.

As shown in the assembly view of FIG. 8C, the configuration of FIG. 8A may be at least temporarily housed within the pen, or autoinjector housing assembly; the depicted pen or autoinjector housing assembly comprises a distal housing portion (726) defining a window (724) therethrough to visualize the injection components therein; a proximal housing portion (728) is movably coupled to a plunger coupling member (730), the distal portion of which is removably coupleable to the plunger housing (69) proximal end (129); a plunger manipulation interface (732) is coupled to the proximal end of the plunger coupling member (730). FIGS. 8D, 8E, and 8F illustrate similar configurations as those of FIGS. 8A, 8B, and 8C, respectively, with the protective needle cap (63) removed, and the needle distal tip (48) ready for injection.

Referring to FIGS. 8G, 8J, and 8M (and, respectively, injection assembly cross sections 8H, 8K, and 8N, and pen or reusable housing assembly integration cross sections 8I, 8L, and 8O), the injection assembly is operated as described in relation to FIGS. 6S/6T, 6U/6V, and 6W/6X, with exception that the manual manipulation by the user is not direct to the injection assembly, but is rather to the pen or autoinjector housing, which is at least temporarily coupled to the injection assembly. Upon full insertion of the plunger tip (36), the needle becomes unlatched and is captured proximally by the plunger tip (36), and loading of the proximal rotatable latch member (714) causes retraction of the needle into a protected configuration, as shown in FIGS. 8P, 8Q, and 8R, leaving a safely used and disposable injection assembly cartridge, as shown in FIG. 8S.

Referring back to FIGS. 8H and 8I, the syringe body (34), such as one constructed from a glass material, may comprise a Luer taper or Luer slip on one end for attachment of the staked needle assembly, such as the staked needle coupling assembly (606) described above. In an alternate embodiment, a cartridge syringe body may be utilized which has a glass flange configuration, similar to that on a medicine vial, which consists of a rubber seal and an aluminum crimp (72, FIG. 16A) to seal the medicine inside the glass cartridge (71, FIG. 16A). With such an embodiment, a needle configuration similar to that shown in FIG. 8I may be snapped over the glass flange to seal the medicine in the cartridge; the aluminum crimp may be replaced with a plastic needle housing.

Referring to FIGS. 8T-8U, a method of assembly a medicine cartridge (800) with a retractable safety needle (810) is shown. The medicine cartridge (800) includes a glass flange (812) on its distal end. This glass flange (812) is configured to couple to a distal seal (814). The distal seal (814) is has a proximal facing cartridge sealing surface (816), and/or a proximally projecting cartridge sealing surface (818). The interior of the distal seal (814) also includes at least one sealing gland (820) for sealing on the external surfaces of the needle spine assembly (76). The needle coupling assembly (606) of the retractable safety needle (810) also includes a snap over interface (822) for coupling the needle coupling assembly (606) to the glass flange (812) of the cartridge (800).

Referring to FIG. 8U, the assembled medicine cartridge (800)/retractable safety needle (810) is shown in a configuration for delivery to the end user. The needle coupling assembly (606) and intercoupled distal seal (814) is assembled onto the glass cartridge 800. The medicine is loaded inside the medicine chamber (40). And the stopper (36) is placed holding the medicine in the medicine chamber (40) for storage and shipping to the customer. The plunger rod including the retraction mechanism may be added before or after delivery to the end user, prior to assembly inside the injector housing.

As shown above the pen injector is shown for reference. The pen injector shown is for illustrative purposes and includes the manual application of force to the plunger rod to expel the medicine from the medicine chamber into the patient. Alternatively, the injector assembly could also incorporate automatic mechanisms such as a coiled spring, motor, ball screw, or linear actuator for the automatic delivery of the drug into the patient once commanded by the patient or caregiver. These autoinjectors function similarly to the syringe or the pen injectors to deliver the medicine to the patient, with the exception of the patient is not tasked with continuous application of force to the plunger rod. A motor or mechanism applies the force for the patient. The autoinjector may be configured to be disposable, reusable, or a combination thereof. The force application mechanisms may be configured to be driven by a battery, spring, or other energy storage mechanism. The automatic needle retraction technologies described herein may be configured to be actuated by the auto injector plunger mechanisms.

As noted above, while the configurations of FIGS. 6A-8U are illustrated using a staked needle/needle housing/latch configuration as described in detail here, such configurations may also utilize a removable Luer type (e.g., Luer lock, Luer taper, Luer slip) coupling and associated hardware.

Figure 16A:
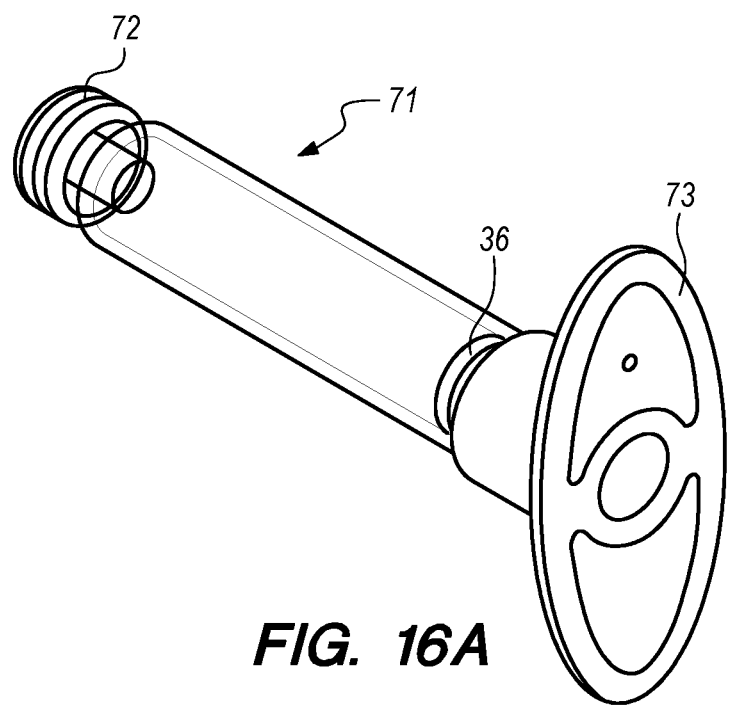
FIGS. 16A-16G illustrate a cartridge safe injection system according to one embodiment.
Figure 16B:
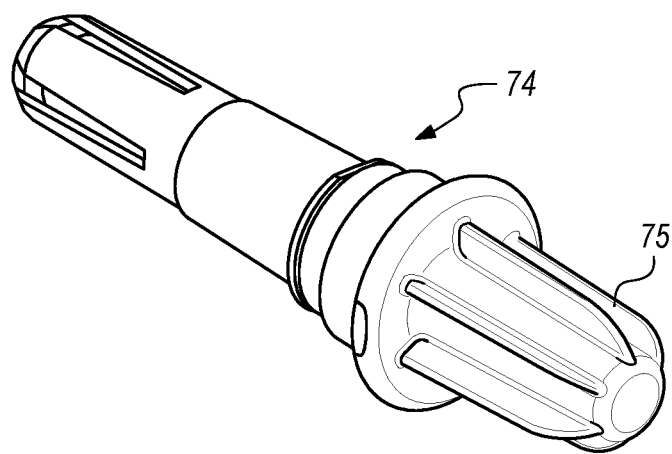
Figure 16C:
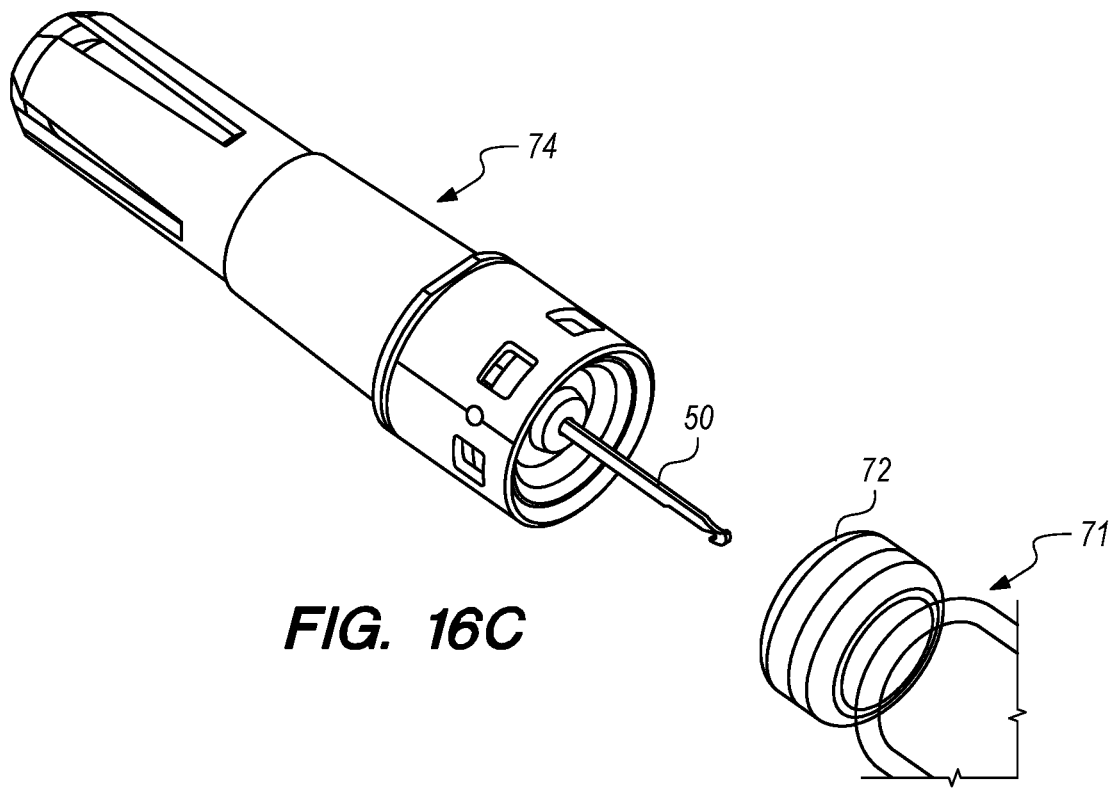
Figure 16D:
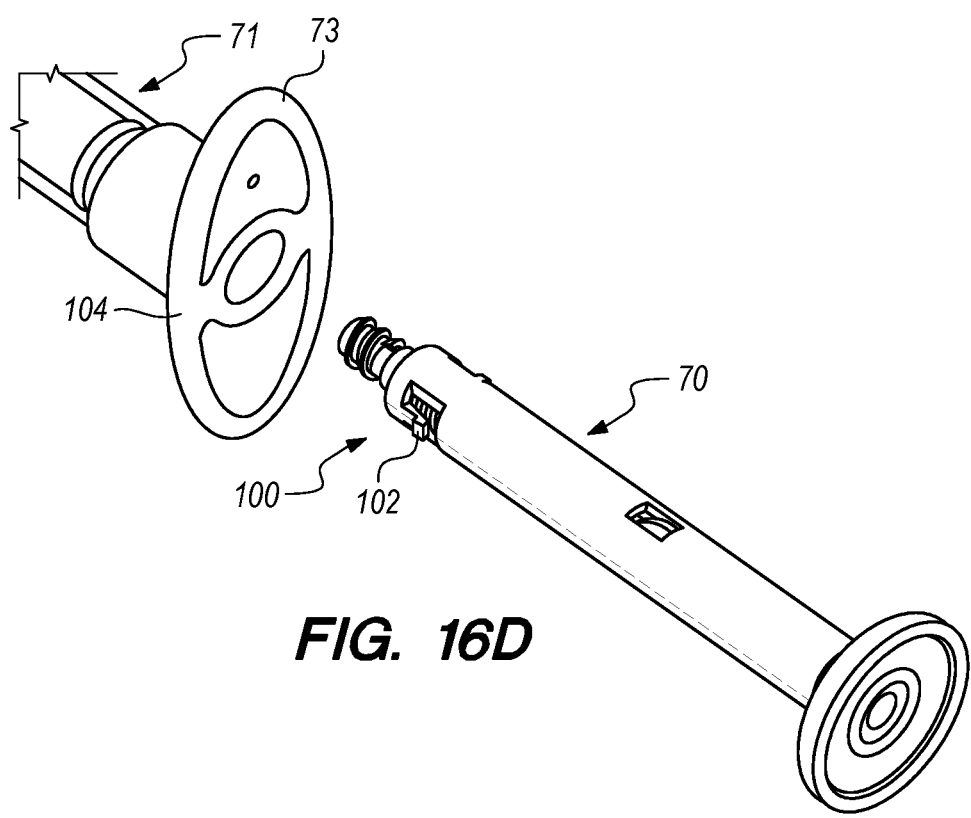
Figure 16E:
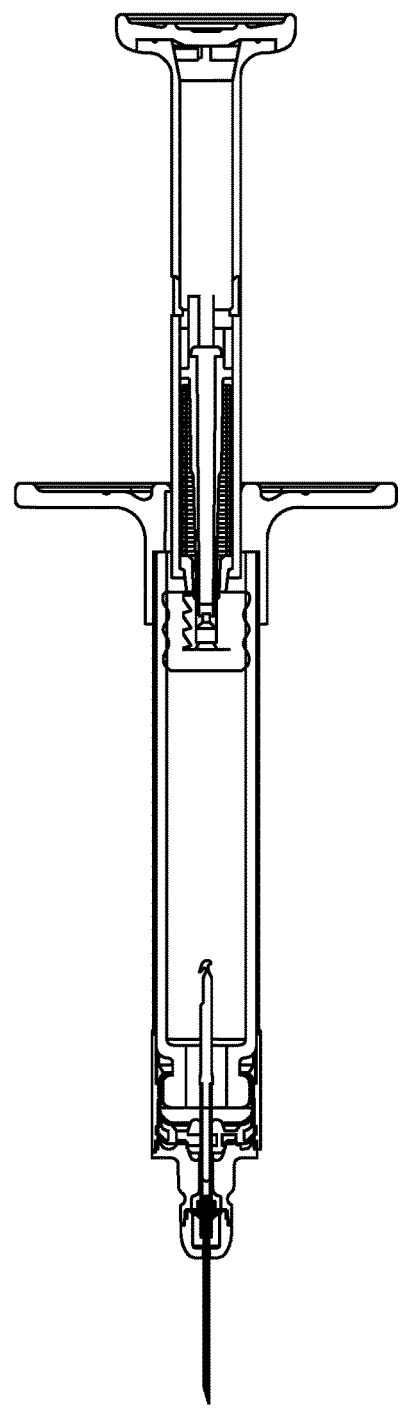
Figure 16F:
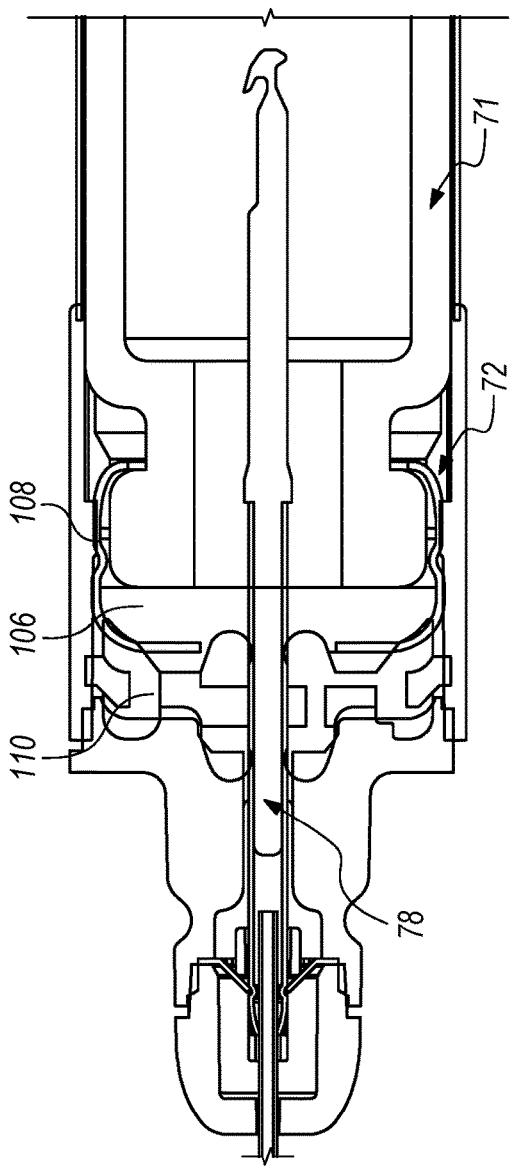
Figure 16G:
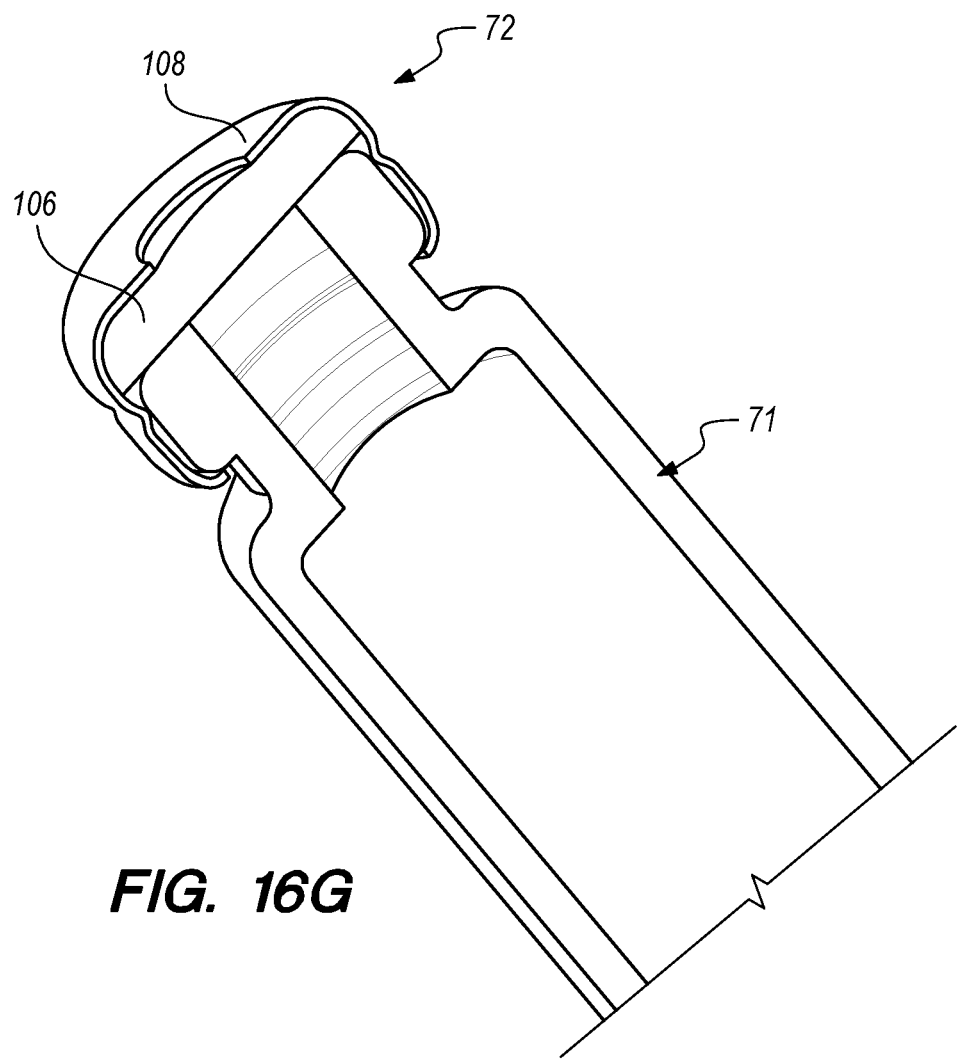
Figure 17A:
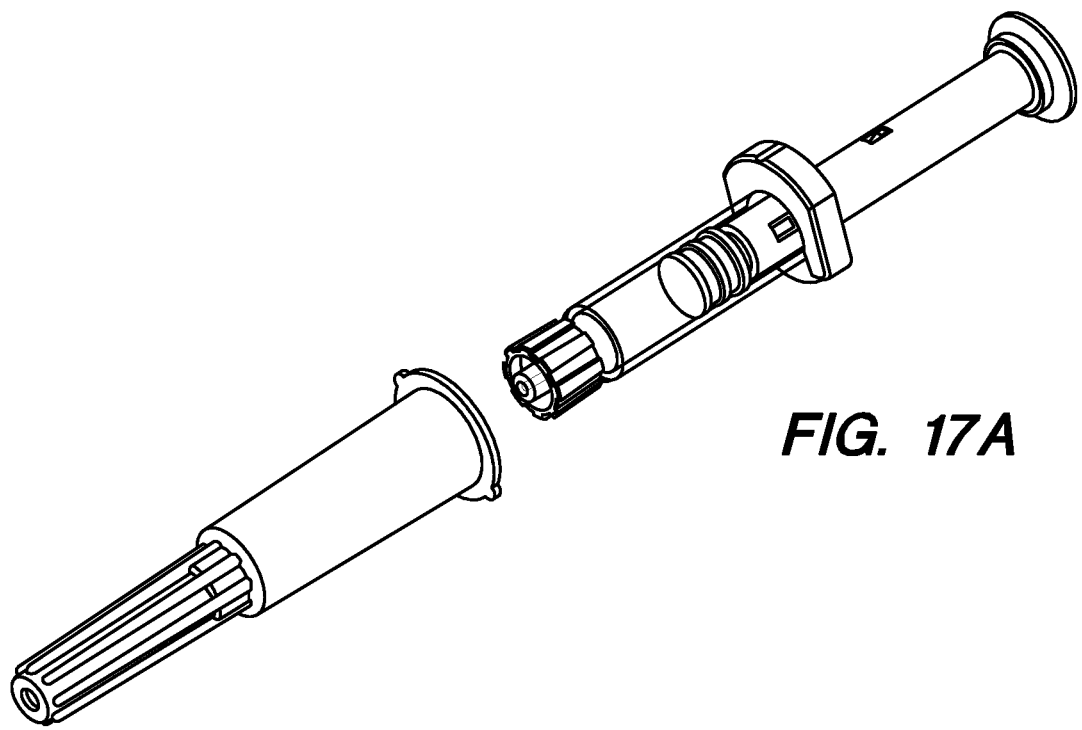
FIGS. 17A-17E illustrate a syringe with an integrated safety needle configured to have a user attachable needle which utilizes a Luer type coupling.
Figure 17B:
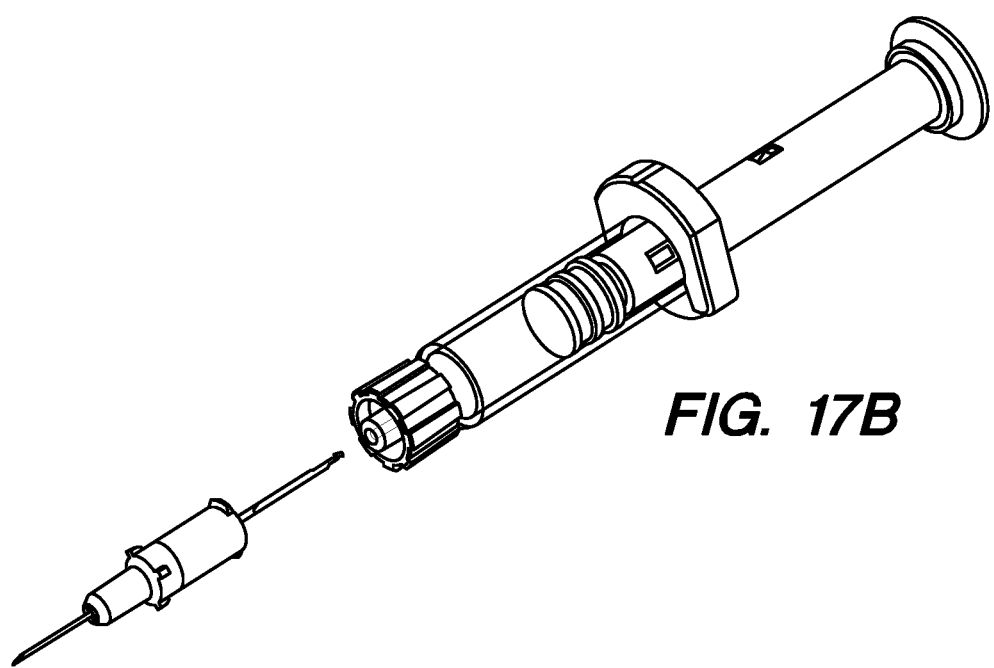
Figure 17C:
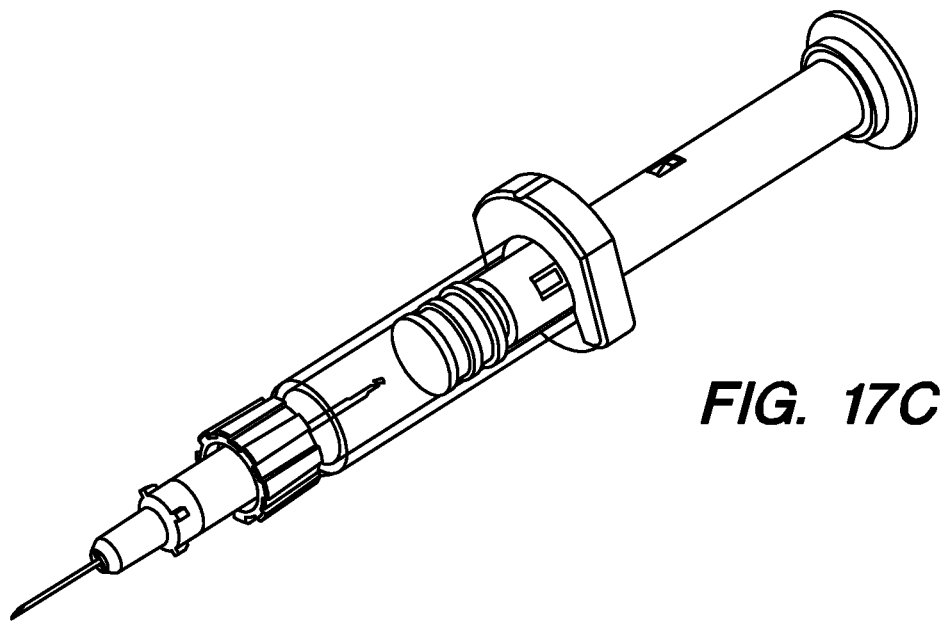
Figure 17D:
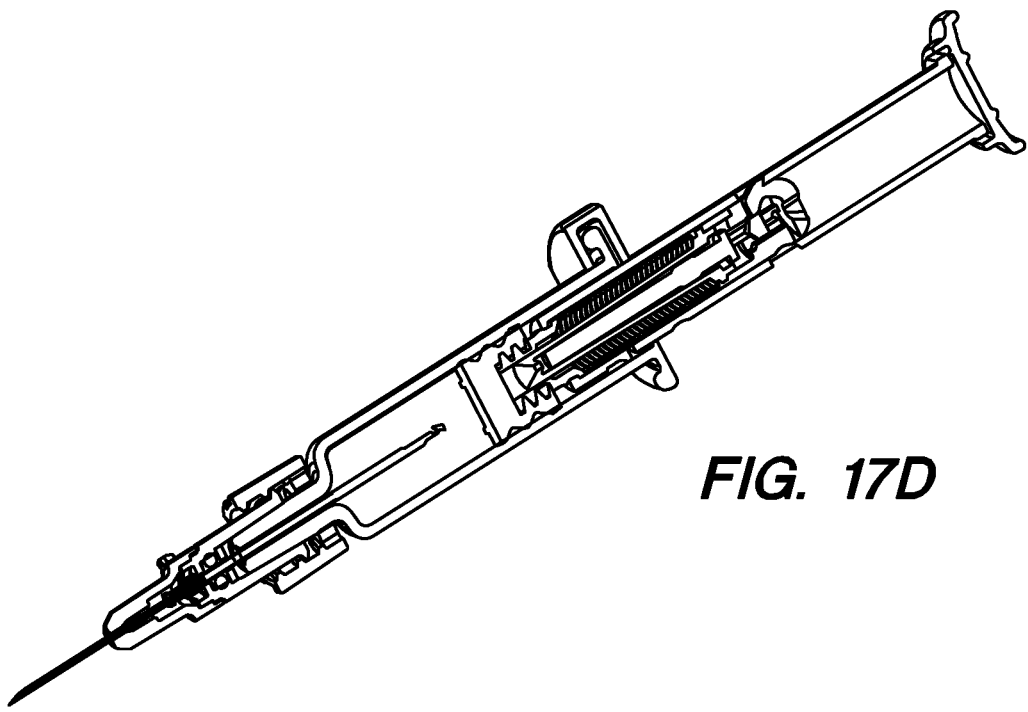
Figure 17E:
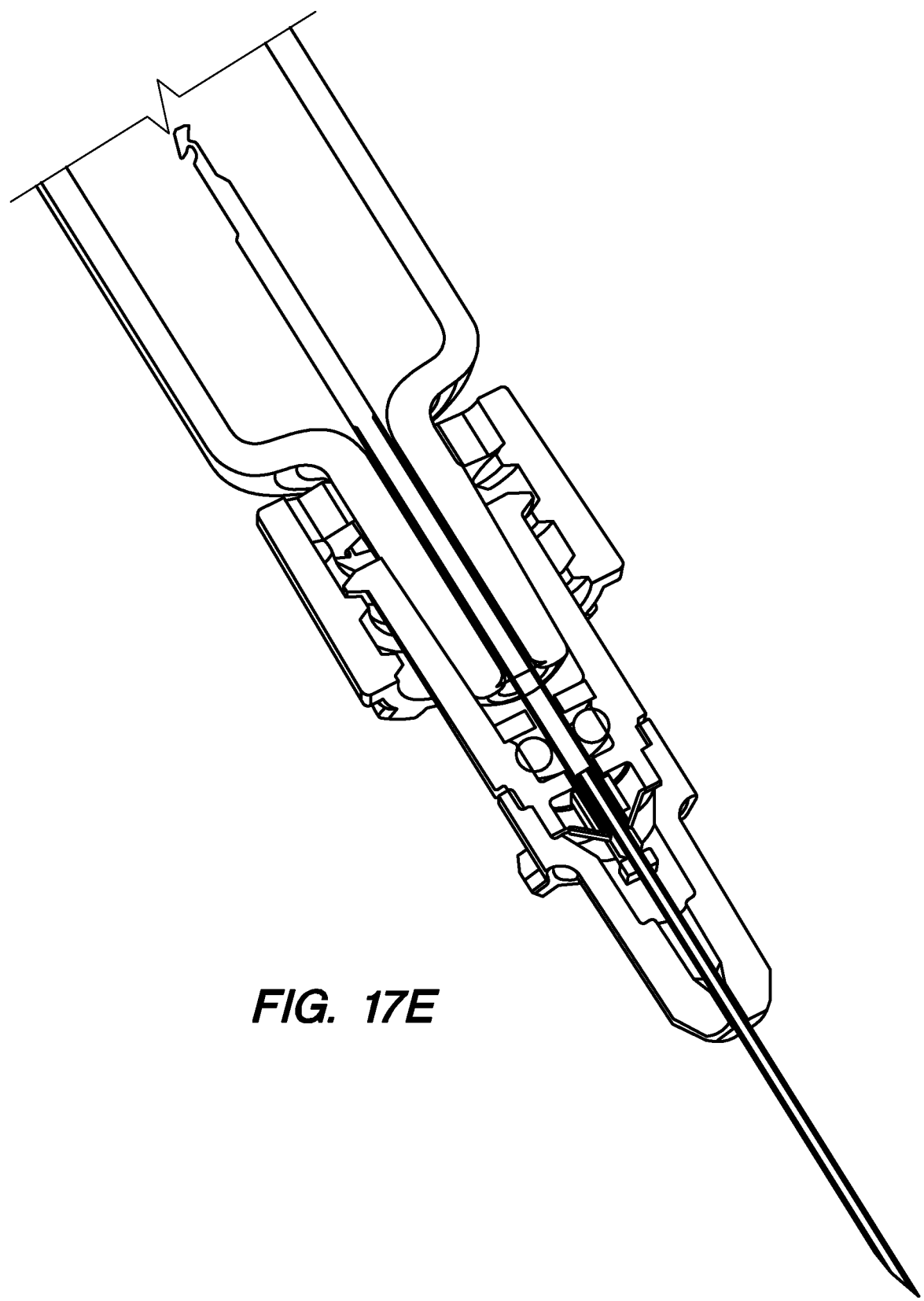

For instance, FIGS. 17A-17E illustrate a syringe with an integrated safety needle configured to have a user attachable needle which utilizes a Luer type (e.g., Luer lock, Luer taper, Luer slip) coupling. FIG. 17A is a Luer type user attachable needle safety syringe where the needle is housed within a needle shield. The needle shield of this type may contain the rotational clutch mechanisms as described in patent Ser. No. 14/696,342, which has been incorporated by reference herein. FIG. 17B shows a user attachable needle in the "ready to be attached state", with the needle shield removed for clarity. FIGS. 17C-17E show perspective and cross sectional views of a syringe with the attachable needle fully attached and ready for the injection to be performed. In certain circumstances, the staked needle configurations may be desired for properties such as glue/adhesive free nature of the described embodiments, silicone films which may be "baked on" due to the fact that adhesive-free staked coupling configurations may not be as limiting on temperatures during processing, and also the tungsten-free nature of the aforementioned staked needle coupling configurations, wherein preferably there is no tungsten pin exposure for forming a needle aperture, as the aforementioned staked coupling configurations utilize Luer-style syringe bodies even for staked coupling, and may be completed using tungsten-free rods. The needle retraction mechanism for the embodiment depicted in FIGS. 17A-17E are similar to the corresponding mechanisms in the embodiments depicted in FIGS. 6A-16G and described above.

Exemplary Needle Assembly Proximal Ends and Needle Retention Features

As described above, the retraction force required to withdraw the needle spine assembly (76) through the stopper (36) and into the plunger housing member (67, 69) is significant compared to the other forces involved in the safe injection systems. For example, in one embodiment, the force required to unlatch the cantilevered latch members (616) to release the needle spine assembly (76) is about 1.5 lbs. In that embodiment, the force required for the needle assembly proximal end (50) to penetrate the stopper (36) and/or the needle retention feature (712) is about 2.5 lbs. The gap between the penetration force (2.5 lbs.) and the unlatching force (1.5 lbs.) ensures that the needle assembly proximal end (50) will not actuate the unlatching member (710) to release the compressed energy-storing member (718) to retract the needle spine assembly (76) before the latch members (716) are unlatched. Once penetrated, the force to pull the needle spine assembly (76) through the stopper (36) and into at least a portion of the plunger assembly is configured to be about 2 lbs. In other embodiments, this needle retraction force is between about 1 lbs. and about 7 lbs. This force depends upon the thickness of the rubber which makes up the distal end of the stopper (36), and the geometry of the needle spine assembly (76). Further, for the staked type syringe, the needle tip (48) is penetrated into the protective cap (63), which can be constructed of a rubber material, for storage of the drug and to prevent leakage of the drug out of the id of the needle tip (48). Upon removal of the protective cap (63), pulling the protective cap (63) distally imparts a distally directed force on the needle tip (48) from the friction between the needle cap (63) and the needle tip (48), in a direction which would attempt to unlock the needle tip (48). Typically, the protective cap (63) imparts between 0.25 lbs. and 1.0 lb. of force on the needle spine assembly (76) during removal of the cap (63). The needle latch (612) and the cantilever members (616) provide a force to resist unlocking the needle spine assembly (76) during removal of the protective cap (63).

When unlatched, the compressed energy-storing member (718) is configured to generate a needle retraction force greater than the force required to pull the needle spine assembly (76) through the stopper (36). In one embodiment, the required needle retraction force is about 3 lbs. In other embodiments, this needle retraction force is about between about 2 lbs. and about 10 lbs. This needle retraction force must be supported by the coupling interaction between the needle assembly proximal end (50) and the needle retention feature (712). The ratio between the needle penetration force and the needle retraction force is defined herein as a penetration/retraction force ratio. The various needle assembly proximal ends (50) and needle retention features (712) described herein are configured to achieve this sizable force differential/ratio in the proximal (insertion/penetration) and distal (retraction) directions.

A. Articulated Needle Assembly Proximal End

Figure 9G:
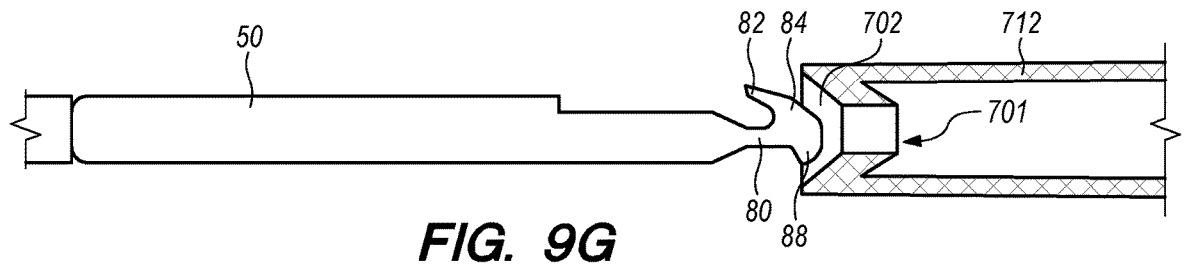
FIGS. 9A-14 illustrate needle assembly proximal ends and/or corresponding needle retention features according to various embodiments.

FIGS. 9A-9I depict a needle assembly proximal end (50) and a corresponding needle retention feature (712) according to one embodiment. As shown in FIGS. 9B and 9D, the most proximal end (84) of the needle assembly proximal end (50) forms an approximate "T" shape that articulates about a pivot (80). The pivot (80) is a "living" metal hinge. The living hinge of the pivot (80) may be configured to be operated by elastic deformation of the metal, plastic deformation of the metal, or a combination thereof. For example, the hinge may elastically deform upon insertion into the needle retention feature (712) to allow for penetration at a sufficiently low force as not to be noticed by the user. Upon needle retraction, the living hinge (80) is configured to plastically deform into a configuration to resist pullout of the needle spine assembly (76) from the needle retention feature (712) at a force sufficiently high to allow for needle retraction through the stopper (36) and into the plunger housing member (67).

Figure 9H:
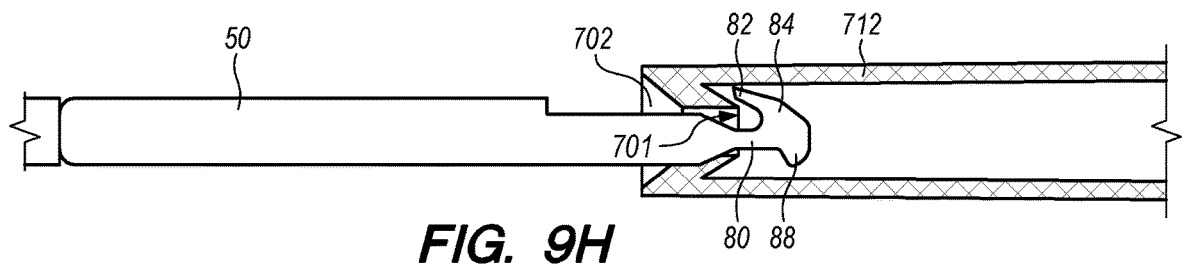
Figure 9I:
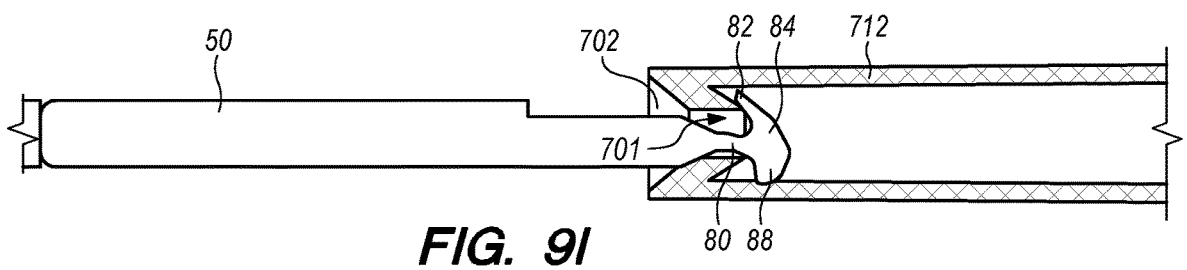

The "T" shaped most proximal end (84) also has a first end (82) and a second end (88). The needle retention feature (712) is a tubular member with a distal opening (701), as shown in FIGS. 9G-9I. The needle retention feature (712) also includes a funnel-shaped flange (702) disposed around the distal opening (701) to guide the most proximal end (84) of the needle spine assembly (76) into the distal opening (701). The needle retention feature (712) is made of an elastically deformable material (e.g., a polymer) such that the distal opening (701) can be enlarged to allow the most proximal end (84) to pass in a proximal direction.

When the "T" shaped most proximal end (84) is being inserted into the needle retention feature (712), it is in an insertion configuration, depicted in FIGS. 9A and 9B. In the insertion configuration, a line (89) connecting the first and second ends (82) (88) is neither orthogonal nor parallel to the longitudinal axis (95) of the needle spine assembly (76). This insertion configuration reduces the profile of the most proximal end (84), thereby reducing the force required to insert the needle assembly proximal end (50) through the stopper 36 and the needle retention feature (712). This insertion is shown in FIGS. 9G and 9H.

When the "T" shaped most proximal end (84) has been inserted into the needle retention feature (712) and is used to retract the needle spine assembly (76), it is in a retraction configuration, depicted in FIGS. 9C and 9D. In the retraction configuration, the line (89) connecting the first and second ends (82) (88) is almost orthogonal to the longitudinal axis (95) of the needle spine assembly (76). This retraction configuration maximizes the profile of the most proximal end (84), thereby increasing the force required to remove the needle assembly proximal end (50) from the needle retention feature (712) and the stopper (36). This retraction configuration is also shown in FIG. 9I.

After the "T" shaped most proximal end (84) has been inserted into the needle retention feature (712), as shown in FIG. 9H, and the compressed energy-storing member (718) is unlatched to retract the needle spine assembly (76), the needle retention feature (712) is retracted proximally and first makes contact with the first end (82) of the most proximal end (84). The force transmitted by the retracting needle retention feature (712) generates a moment about the pivot (80), which plastically deforms the most proximal end (84) such that it permanently converts between the insertion configuration depicted in FIG. 9B to the retraction configuration depicted in FIG. 9D. As shown in FIG. 9I, the most proximal end (84) in the retraction configuration engages opposite sides of the distal end of the needle retention feature (712), thereby coupling the needle retention feature (712) and the needle spine assembly (76) with respect to proximal movement along the longitudinal axis of the needle spine assembly (76) by increasing the surface area contacted between the most proximal end (84) and the needle retention feature (712). The conversion between the insertion configuration and the retraction configuration allows the needle assembly proximal end (50) and the corresponding needle retention feature (712) to have the insertion force/retraction force differential/ratio required for the safe injection system.

FIGS. 9E and 9F depict a needle spine assembly (76) according to the embodiment depicted in FIGS. 9A-9D. The needle spine assembly (76) comprises a sharpened hypodermic needle tip formed on a tubular injection member (78), a hollow joining member (83), and a needle assembly proximal end (50). The hollow joining member (83) couples the tubular injection member (78) and the needle assembly proximal end (50). The injection member (78), the needle proximal end (50), and hollow joining member (83) may be held together with interference fits, welds, and/or adhesives. The needle proximal end (50) may be formed from a thin sheet metal component using laser cutting, etching, stamping, and/or machining techniques, for example. The most proximal end (84) of the needle assembly proximal end (50) has a flat cross-section as illustrated in FIGS. 9E and 9F.

Figure 10C:
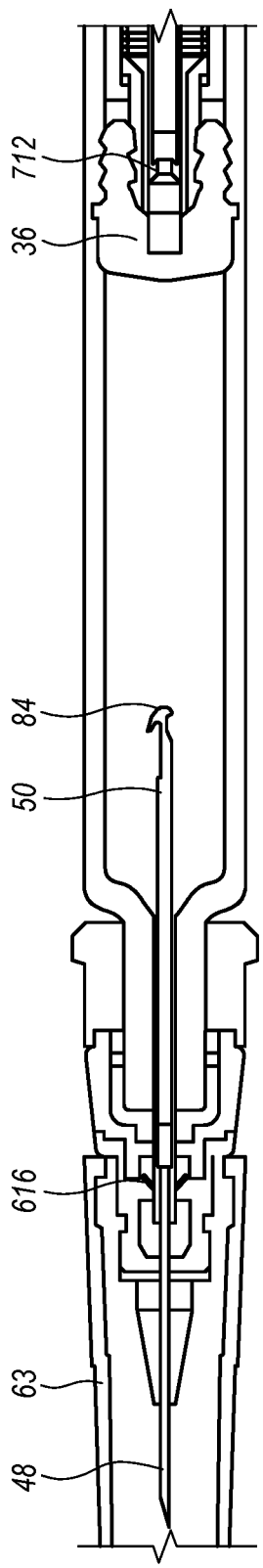
Figure 10D:
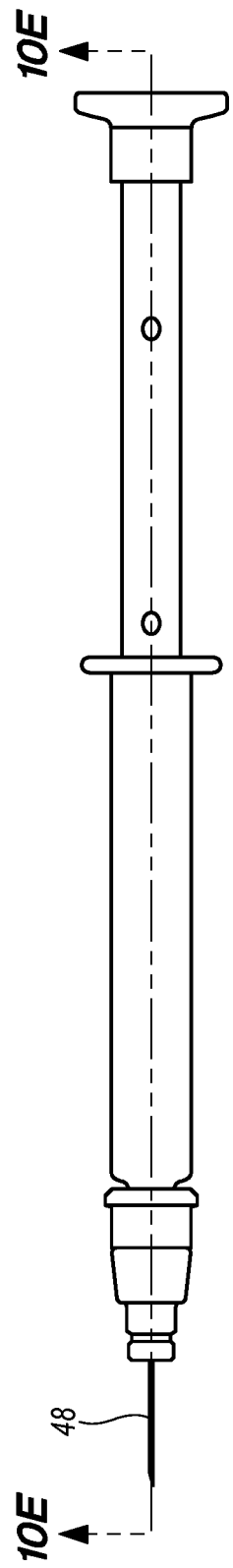
Figure 10E:
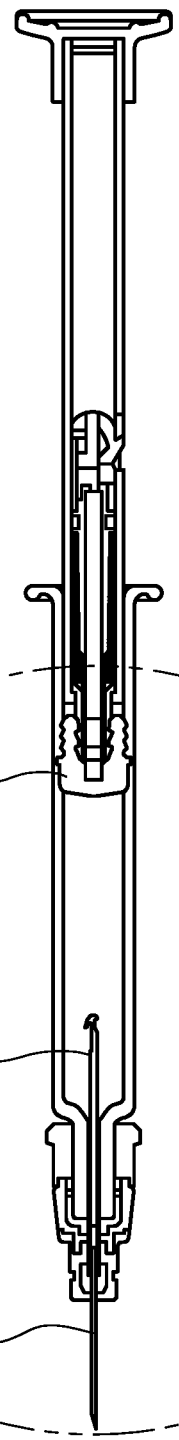
Figure 10F:
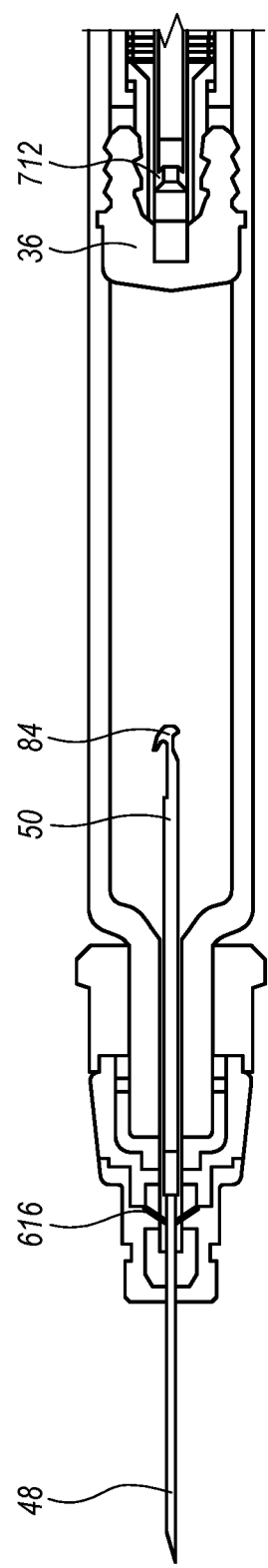
Figure 10G:
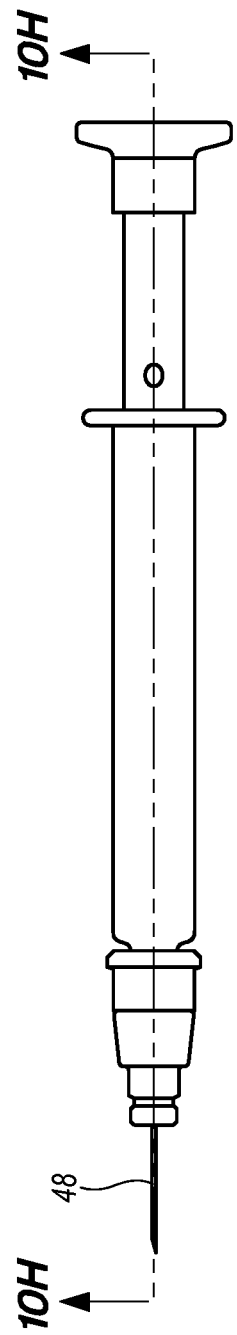
Figure 10H:
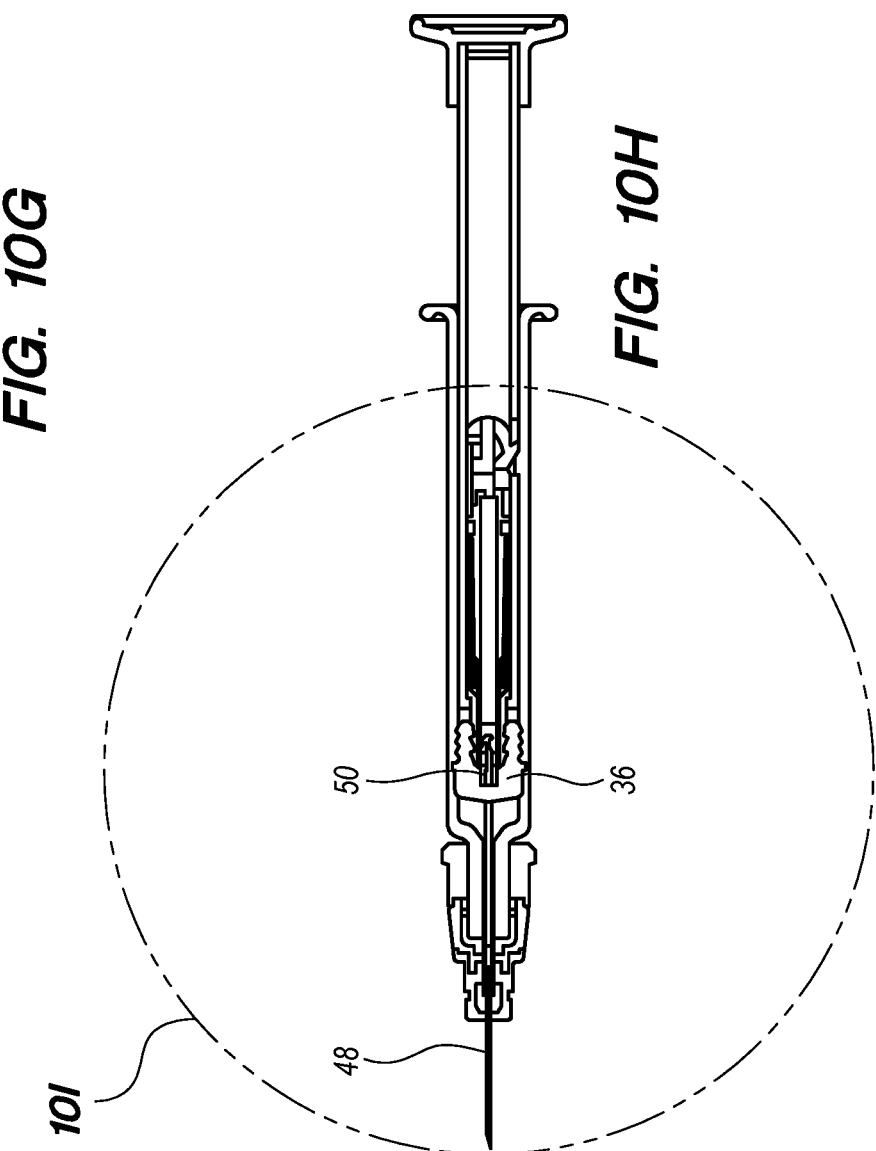
Figure 10I:
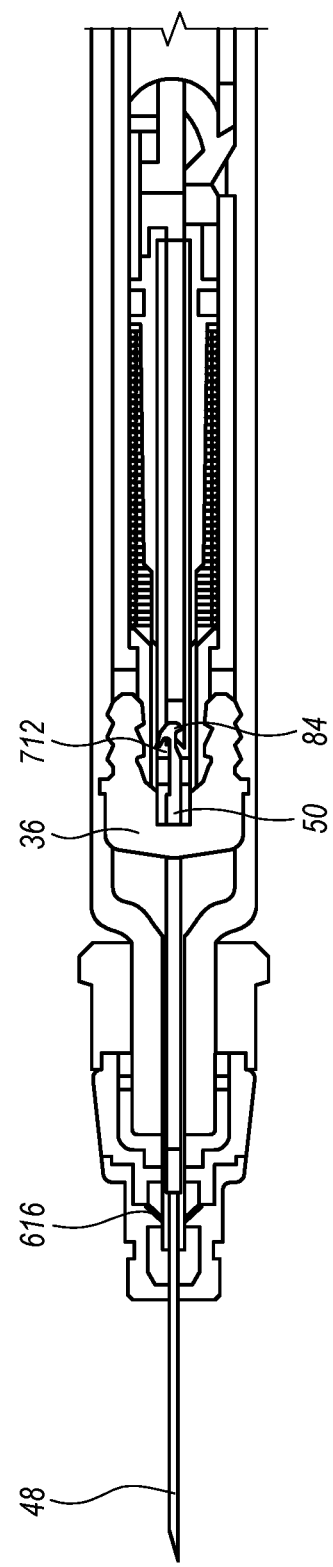
Figure 10L:
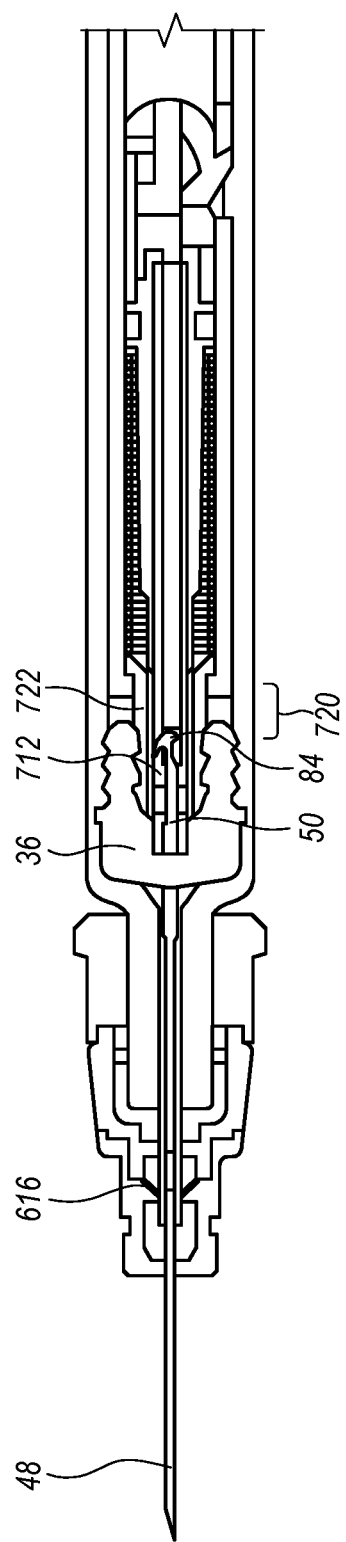
Figure 100:
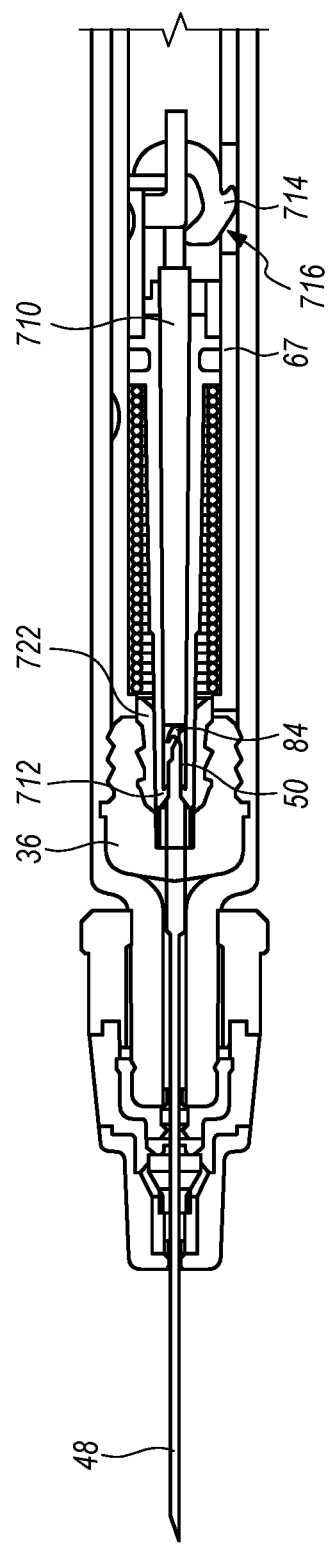
Figure 10P:
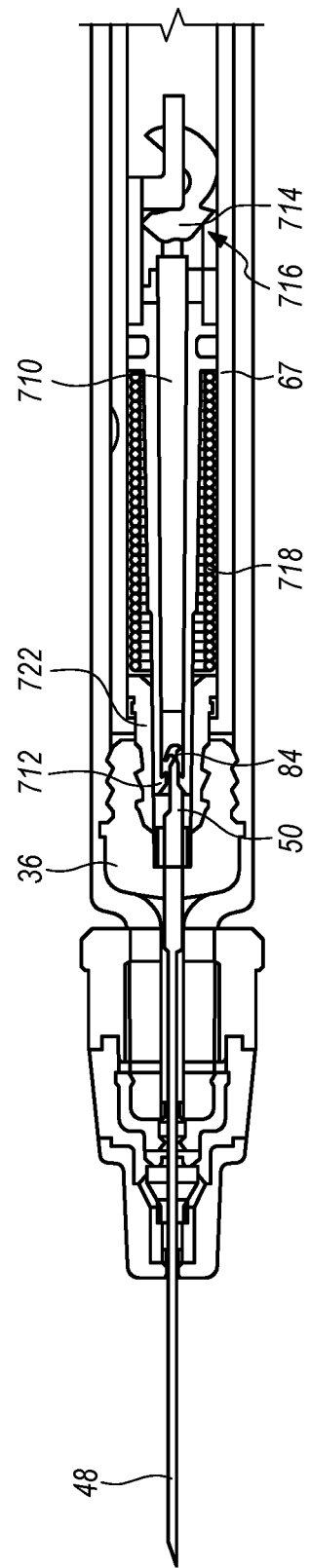
Figure 10Q:
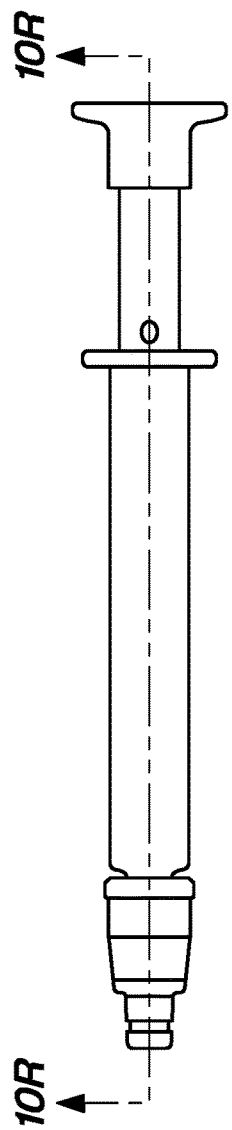
Figure 10R:
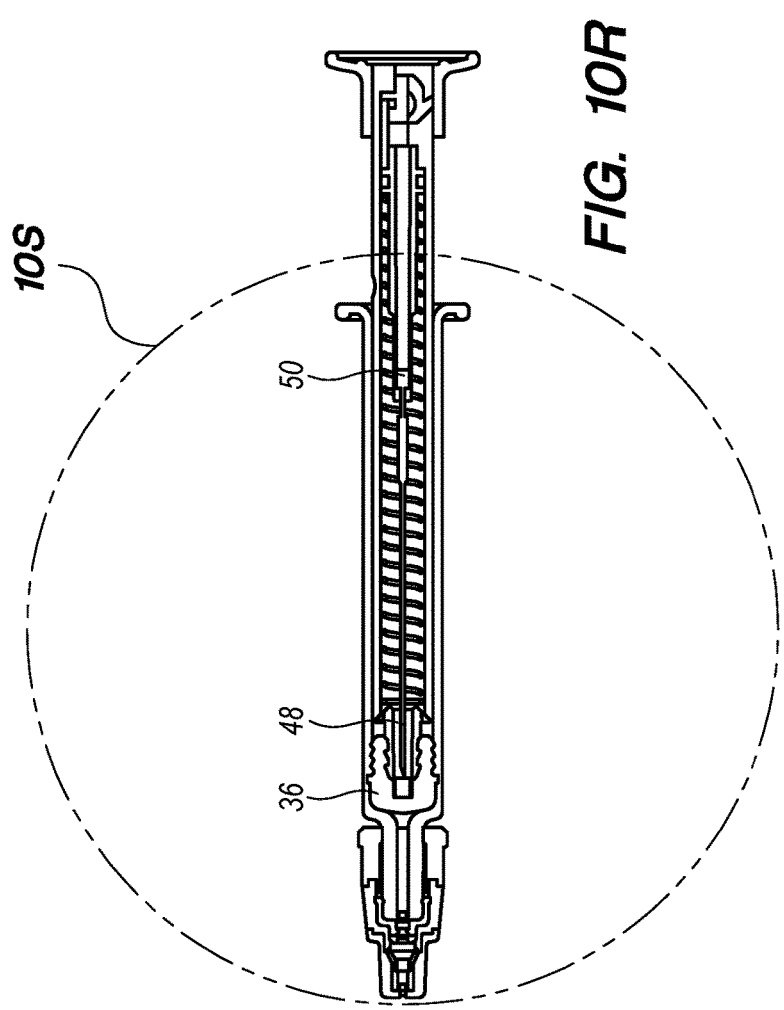
Figure 10S:
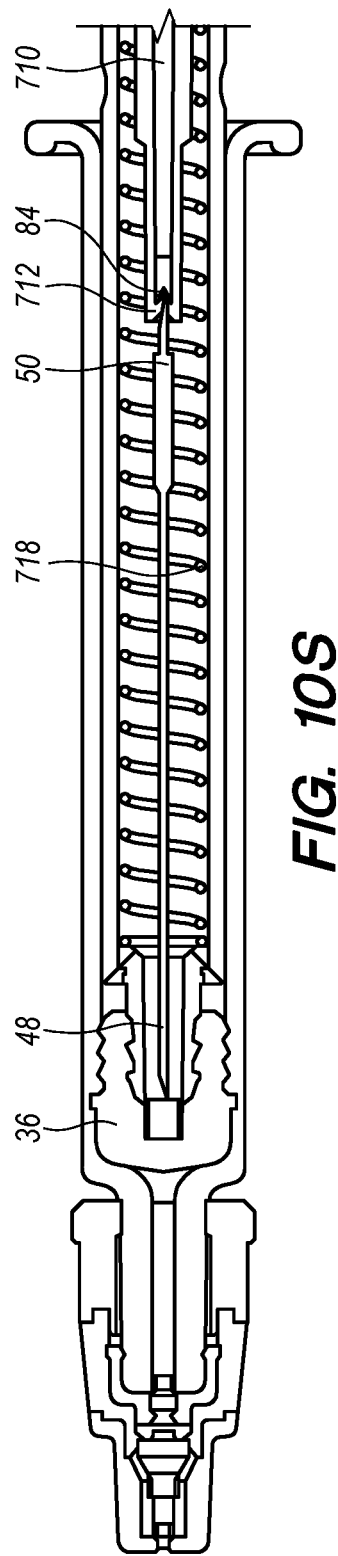

FIGS. 10A-10S depict an injection process using a safe syringe system including the "T" shaped most proximal end (84) depicted in FIGS. 9A-9I. FIGS. 10A-10C illustrate such an injection assembly ready to use with a protective cap (63) isolating the distal needle tip (48). FIG. 10C also illustrates the "T" shaped most proximal end (84) on the needle assembly proximal end (50).

FIGS. 10D-10F illustrate the protective cap (63) removed, ready for injection. FIGS. 10G-10I illustrate an aspiration step, as described above, wherein the plunger may be pulled backwards relative to the syringe to confirm needle location.

Thus in operation, upon full insertion of the plunger tip (36) relative to the syringe body (34), several things happen: the needle latching (616) mechanism becomes unlatched, allowing for retraction of the needle (compare FIGS. 10I and 10L); the insertional load threshold is passed, causing the coupling member (722) to collapse the gap (720) and allow for full capture of the needle proximal end (50) by the needle retention features (712) (compare FIGS. 10L and 10O); and compressive loads from the needle proximal end (50) abutting the unlatching member (710) cause the rotatable latching member (714) to be free to rotate out of the latched position relative to the lock interface window (716) defined into the plunger housing member (67), as shown in FIGS. 10O and 10P. FIGS. 10Q-10S illustrate the condition of the assembly after the needle has been retracted such that the distal needle tip (48) is housed within the plunger housing member (67) and the plunger tip (36) (i.e., into a protected configuration).

Closing the gap (720) causes the most distal end (84) to penetrate the needle retention feature (712), which achieves several results. The penetration generates resistance, which provides a tactile indication that the medicine has been completely delivered. The penetration also couples the most distal end (84) and the needle retention feature (712) in a retracting direction. The penetration further allows the most distal end (84) to engage the unlatching member (710). The unlatching member (710) in turn actuates the rotatable latching member (714) to retract the needle spine assembly (76).

The above-described retraction mechanism requires both the presence of a needle spine assembly (76) (i.e., the most distal end (84) thereof) and the positioning of a plunger (i.e., the unlatching member (710) contained therein) to retract the needle spine assembly (76). Accordingly, injection systems including the above-described retraction mechanism can be used without a needle (e.g., to mix liquid and powder medication in an external vessel) with no risk of accidentally firing the retraction mechanism and rendering the system useless.

While the embodiment depicted in FIGS. 9A-9I and 10A-10S include a most proximal end (84) of the needle assembly proximal end (50) forms an approximate "T" shape that articulates about a pivot (80), other embodiments may including most proximal ends (84) that take different shapes. Embodiments of safety injection systems including an articulated needle assembly proximal end articulate/transform from an insertion configuration to a retraction configuration. In the insertion configuration, the most proximal end is configured to be inserted into the needle retention feature with relatively low force. In the retraction configuration, the most proximal end is configured to remain coupled to the needle retention feature under relatively high retracting/separating force. The structure of the articulated needle assembly proximal end and its corresponding needle retention feature therefore achieves the insertion force/retraction force differential/ratio required for the safe injection system.

B. Needle Assembly Proximal End with Bent Tang(s)

Figure 11A:
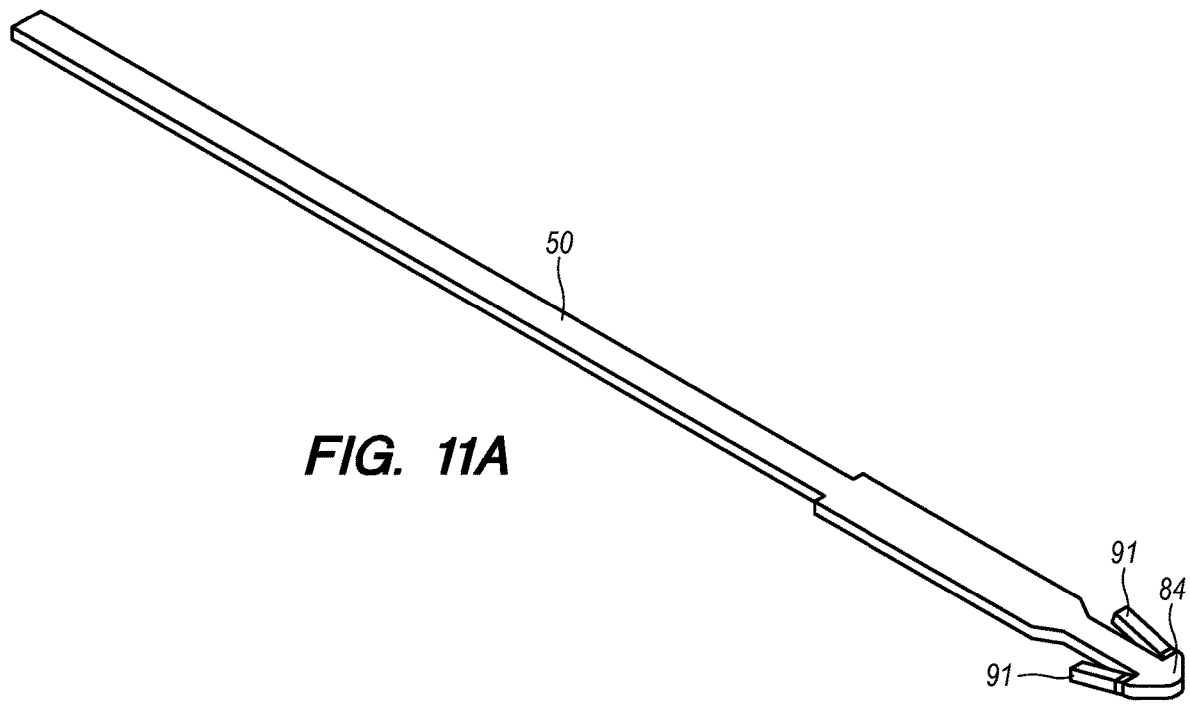
Figure 11B:
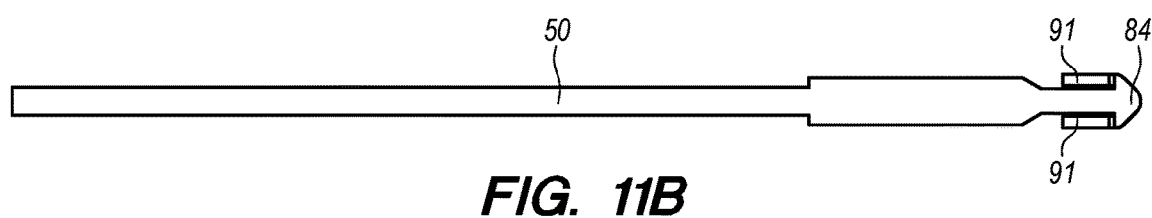
Figure 11C:
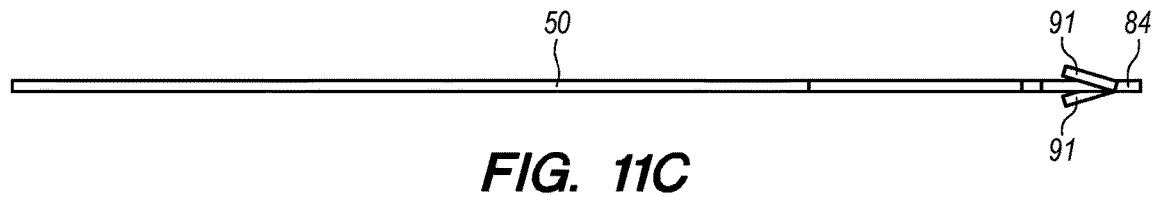

FIGS. 11A-11C depict a needle assembly proximal end (50) according to another embodiment. The most proximal end (84) of the needle assembly proximal end (50) forms a proximally pointed arrowhead shape with a pair of tangs (91) extending backwards (i.e., distally) from the arrowhead.

The needle proximal end (50) may be formed from a thin sheet metal component using stamping, laser cutting, etching, and/or machining techniques, for example. The tangs (91) are biased (e.g., heat set) to deflect out of the plane defined by the needle assembly proximal end (50). Each tang (91) is biased to deflect in a different direction out of the plane.

The needle assembly proximal end (50) depicted in FIGS. 11A-11C is configured to couple to a needle retention feature (712) similar to the one depicted in FIGS. 9G-9I and described above. When the needle assembly proximal end (50) is inserted into the needle retention feature (712), the tangs (91) elastically deflect toward the plane defined by the needle assembly proximal end (50), thereby reducing the axial profile of the most proximal end (84) of the needle assembly proximal end (50) and reducing insertion force. This is the insertion configuration. After the needle assembly proximal end (50) has been inserted into the needle retention feature (712), the tangs (91) return to their biased shape out of the plane defined by the needle assembly proximal end (50). In this retraction configuration, the free distal ends of the tangs (91) catch on the inside of the needle retention feature (712) and increase the retraction force transmitted by the coupled needle assembly proximal end (50) and needle retention feature (712).

While the most proximal end (84) depicted in FIGS. 11A-11C has two tangs (91), alternative embodiments have other tang configuration. For instance, the most proximal end can have a single tang or more than two tangs. Embodiments of safety injection systems including a bent tang needle assembly proximal end are biased to form a retraction configuration and can form an insertion configuration under force (e.g., during insertion through a needle retention feature). In the insertion configuration, the most proximal end is configured to be inserted into the needle retention feature with relatively low force. In the retraction configuration, the most proximal end is configured to remain coupled to the needle retention feature under relatively high retracting/separating force. The structure of the bent tang needle assembly proximal end and its corresponding needle retention feature therefore achieves the insertion force/retraction force differential/ratio required for the safe injection system.

C. Needle Assembly Proximal End Tip with Barb(s)

FIGS. 12A-12D depict a needle assembly proximal end (50) according to still another embodiment. The most proximal end (84) of the needle assembly proximal end (50) is generally cylindrical with a rounded conical proximal end and a pair of barbs (92) extending radially outward and backwards (i.e., distally) from the cylinder forming the most proximal end (84). The barbs (92) are on opposite sides of the cylinder and are displaced from each other longitudinally. The barbs (92) are displaced longitudinally to minimize the amount of material removed from any particular longitudinal portion of the cylinder to form the barbs (92). The needle proximal end (50) may be formed from a metal wire component using machining techniques, for example. The barbs (92) are biased (e.g., heat set) to deflect radially away from the cylinder.

Figure 12A:
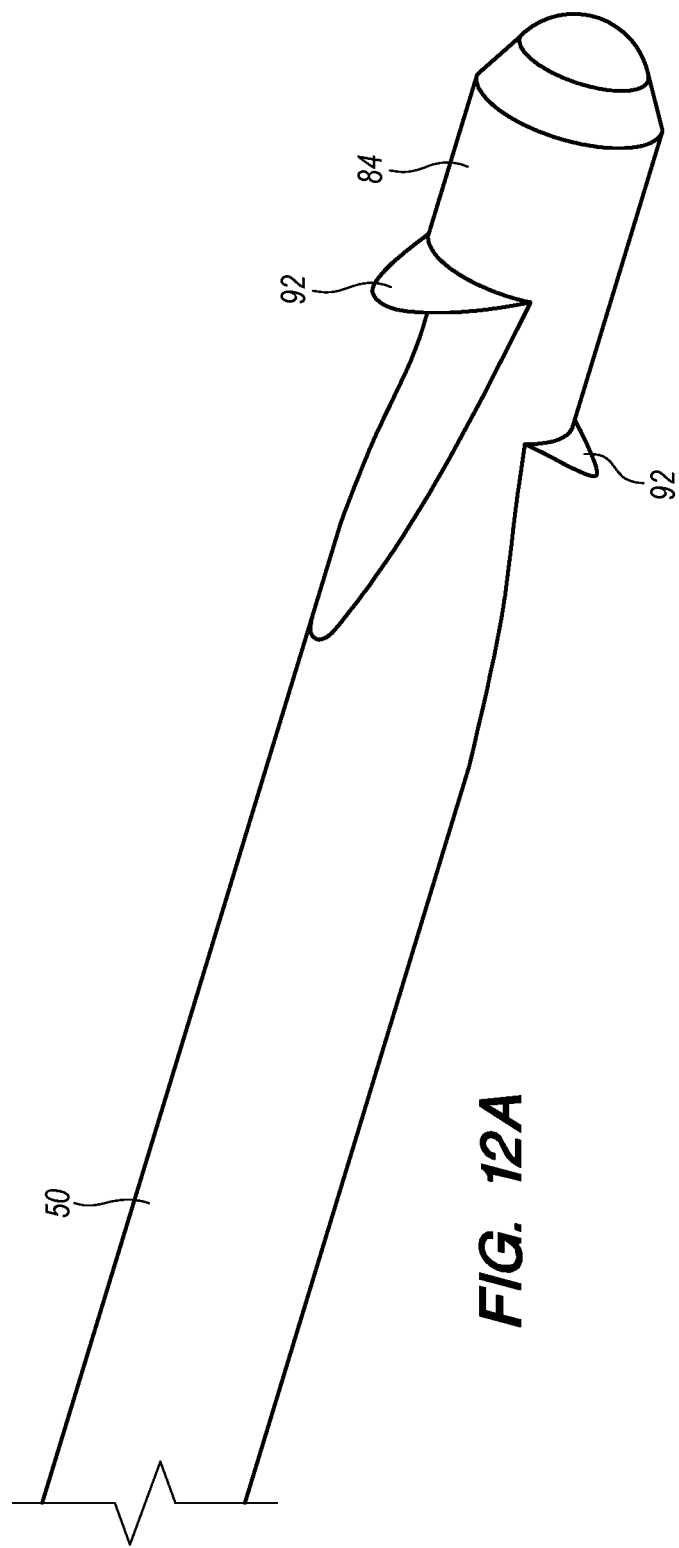
Figure 12B:
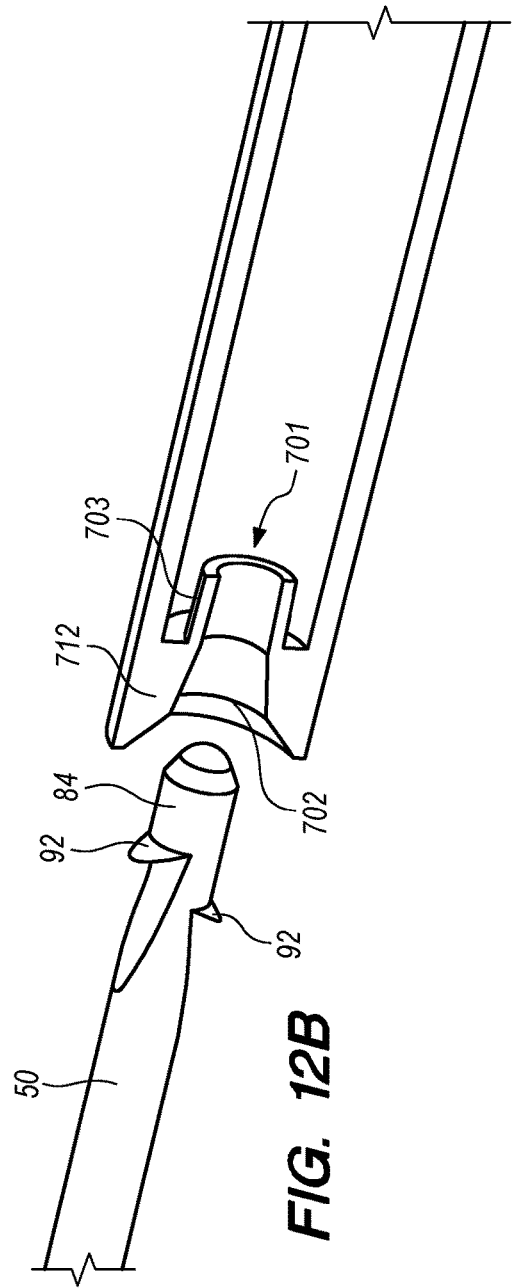
Figure 12C:
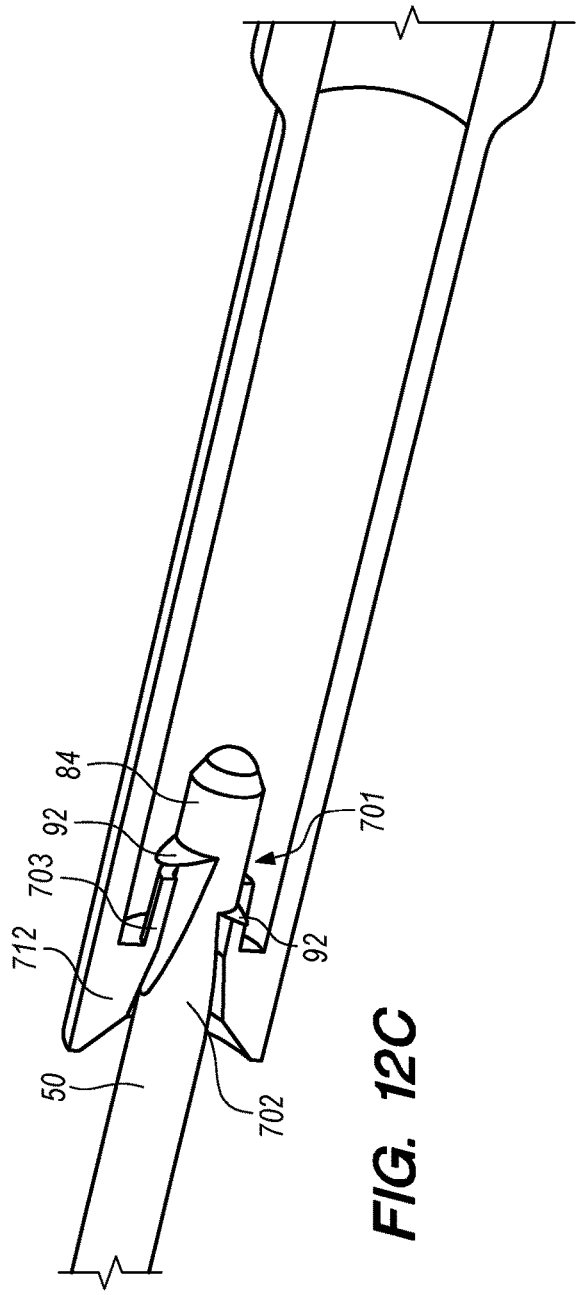
Figure 12D:
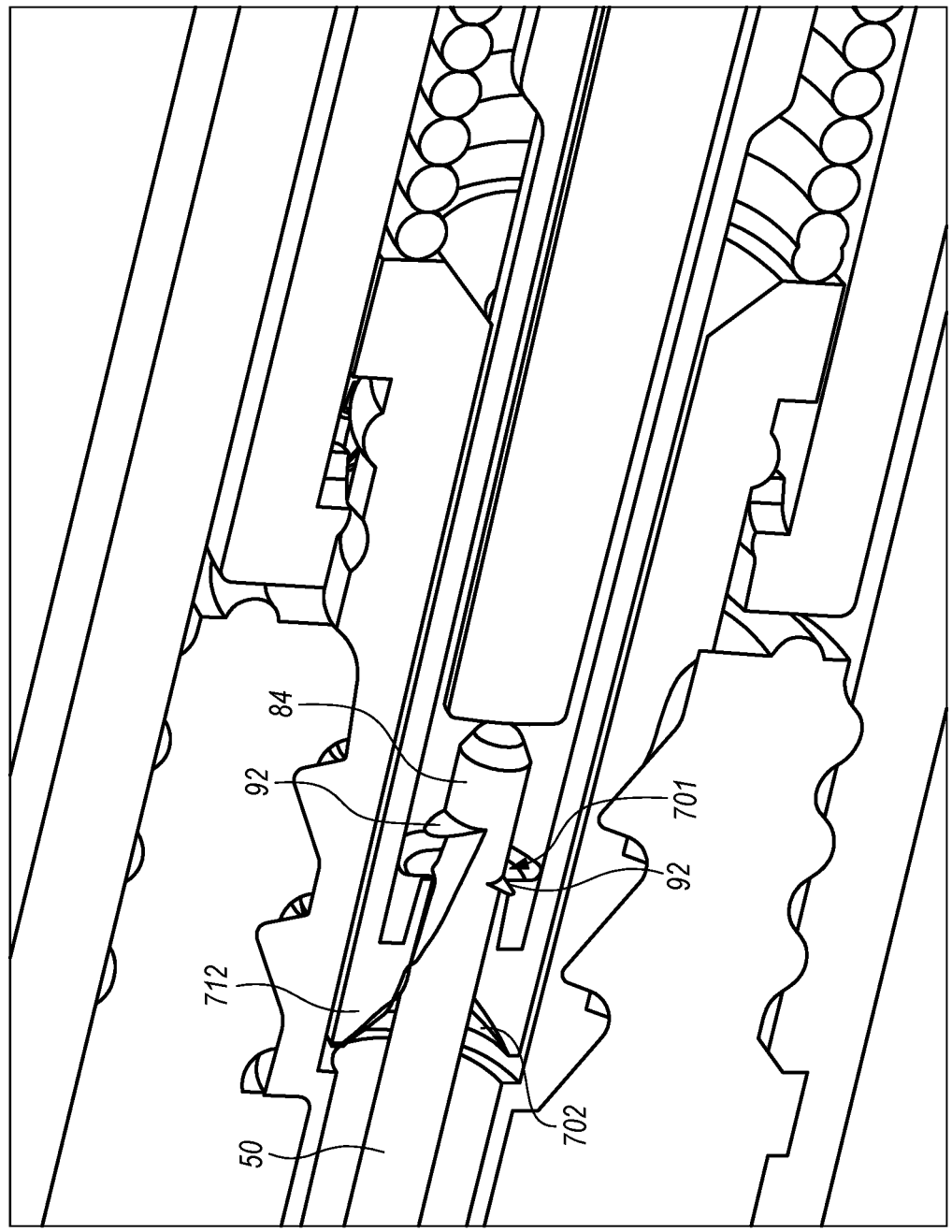
Figure 13A:
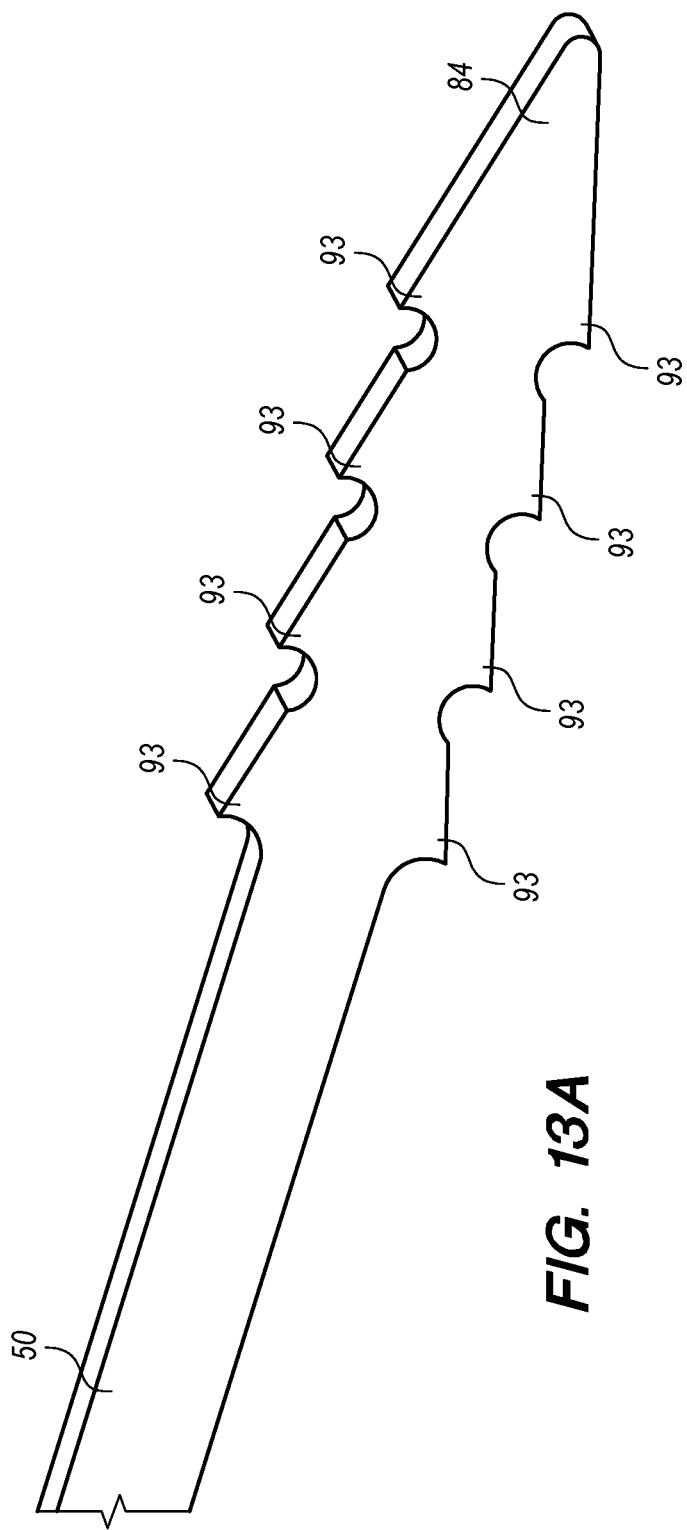
Figure 13B:
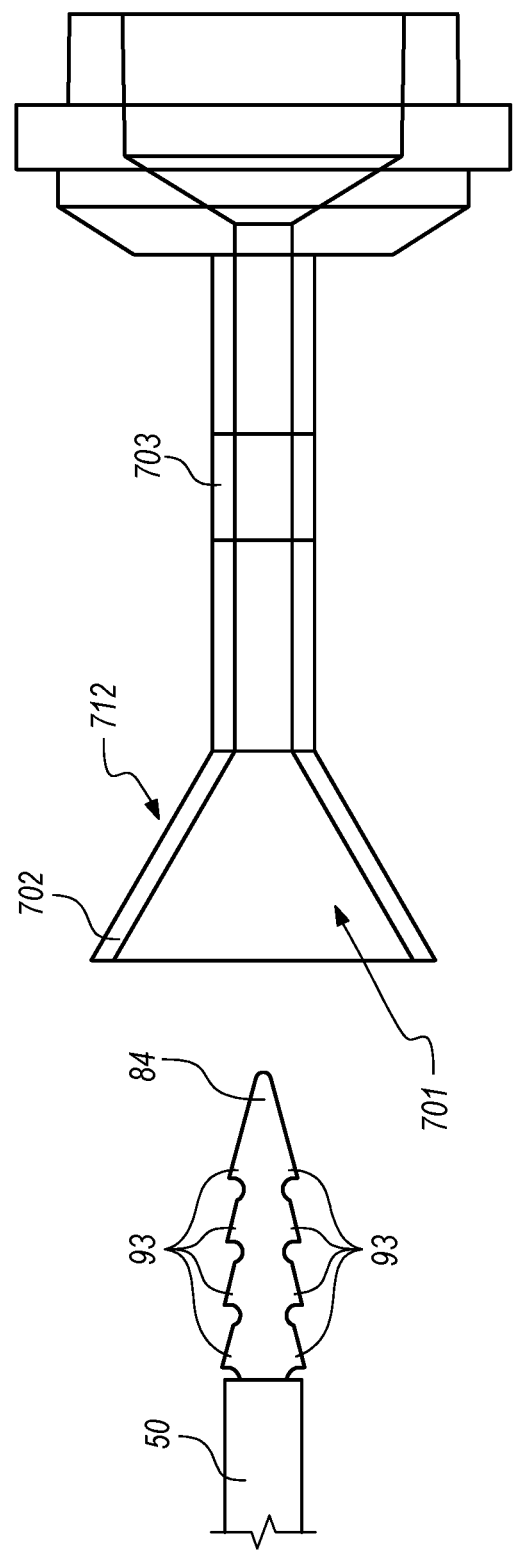
Figure 13C:
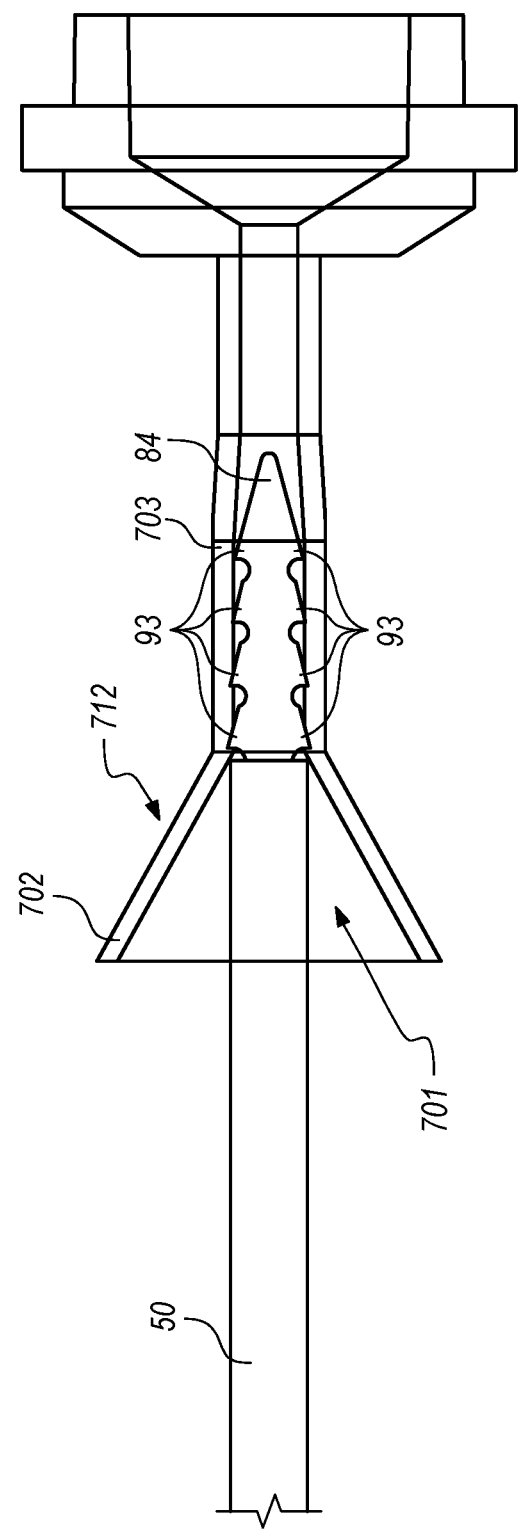
Figure 13D:
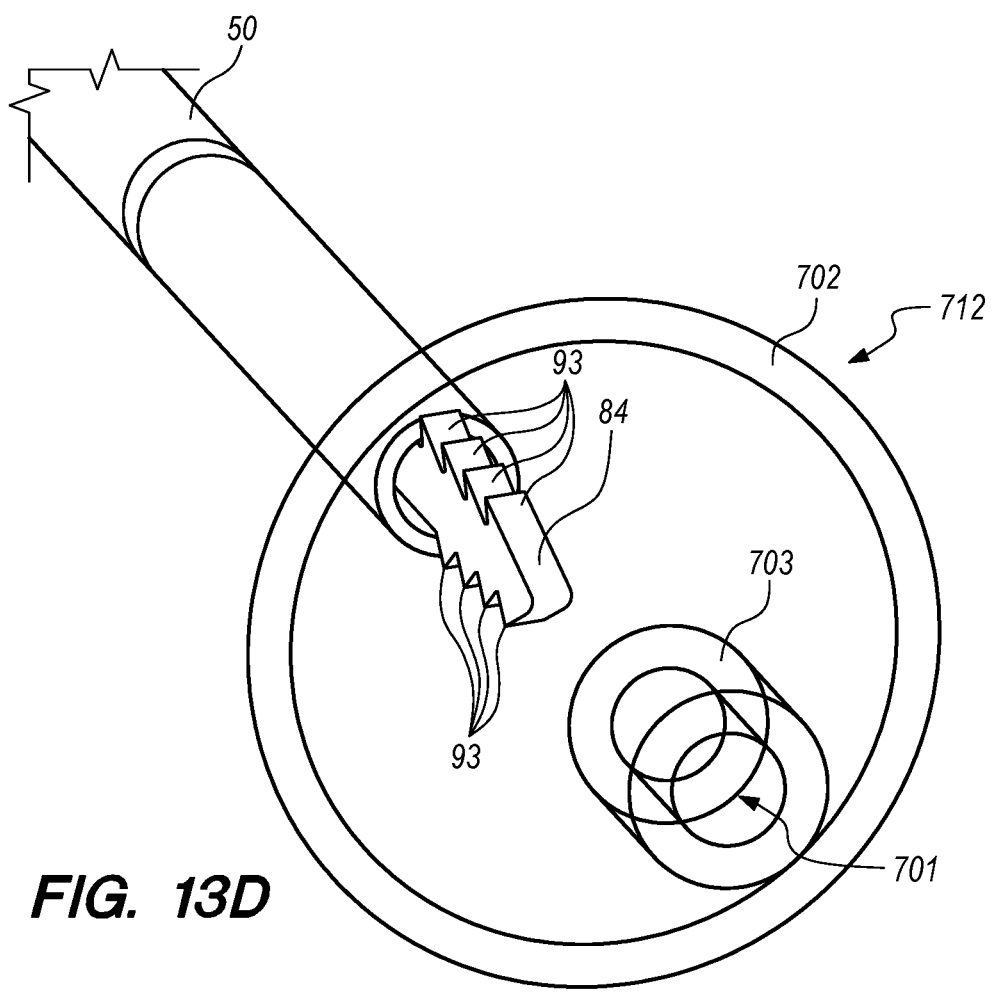
Figure 13E:
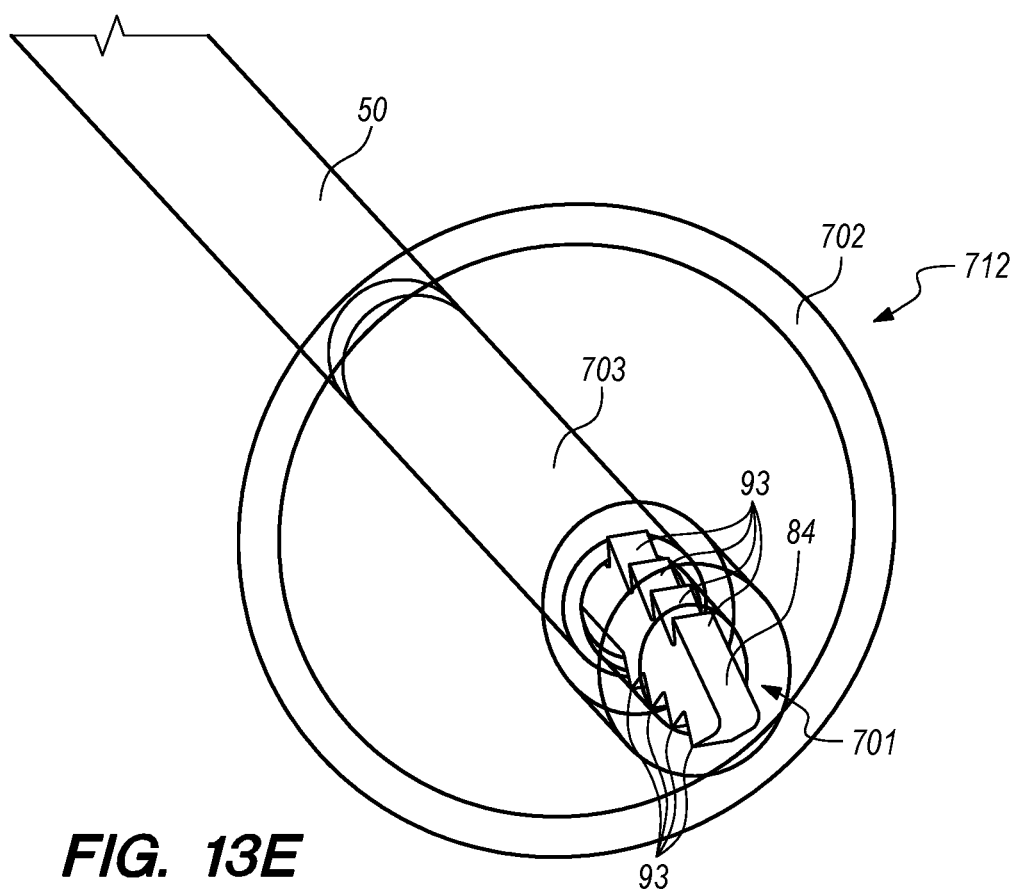

The needle assembly proximal end (50) depicted in FIGS. 12A-12D is configured to couple to a needle retention feature (712) similar to the one depicted in FIGS. 9G-9I and described above. The needle retention feature (712) is a tubular member with a distal opening (701), as shown in FIGS. 12B-12D. The needle retention feature (712) also includes a funnel-shaped flange (702) disposed around the distal opening (701) to guide the most proximal end (84) of the needle spine assembly (76) into the distal opening (701). In addition, the needle retention feature (712) includes a proximally directed collar (703) formed around the inside of the distal opening (701). The collar (703) has a smooth inner diameter. The needle retention feature (712) is made of an elastically deformable material (e.g., a polymer) such that the distal opening (701) and the collar (703) can be enlarged to allow the most proximal end (84) to pass in a proximal direction.

When the needle assembly proximal end (50) is inserted into the needle retention feature (712), the barbs (92) elastically deflect radially toward the cylinder forming the most proximal end (84), thereby reducing the axial profile of the most proximal end (84) of the needle assembly proximal end (50) and reducing insertion force. This is the insertion configuration. After the needle assembly proximal end (50) has been inserted into the needle retention feature (712), the barbs (92) return to their biased shape radially outward from the cylinder. In this retraction configuration, the free distal ends of the barbs (92) catch on the free end and the inside of the collar (703) and increase the retraction force transmitted by the coupled needle assembly proximal end (50) and needle retention feature (712). The collar (703) also deforms to retain the most proximal end (84). Further, one or both of the barbs (92) may scrape the inner diameter of the collar (703) to retain the most proximal end (84). Because the barbs (92) are longitudinally displaced from each other, the barbs (92) can sequentially catch on the collar (703) to minimize strain thereon.

While the most proximal end (84) depicted in FIGS. 12A-12D has two barbs (92), alternative embodiments have other barb configuration. For instance, the most proximal end can have a single barb or more than two barbs. In one embodiment, the most proximal end has three barbs distributed 120 degrees away from each other around a longitudinal axis of the cylinder forming the most proximal end. Embodiments of safety injection systems including a barbed needle assembly proximal end are biased to form a retraction configuration and can form an insertion configuration under force (e.g., during insertion through a needle retention feature). In the insertion configuration, the most proximal end is configured to be inserted into the needle retention feature with relatively low force. In the retraction configuration, the most proximal end is configured to remain coupled to the needle retention feature under relatively high retracting/separating force. The structure of the barbed needle assembly proximal end and its corresponding needle retention feature therefore achieves the insertion force/retraction force differential/ratio required for the safe injection system.

D. Tree-Shaped Needle Assembly Proximal End

FIGS. 13A-13E depict a needle assembly proximal end (50) according to yet another embodiment. The most proximal end (84) of the needle assembly proximal end (50) forms a tree shape with eight non-articulating teeth (93) extending radially outward and backwards (i.e., distally) from the longitudinal axis of the tree shape. The needle proximal end (50) may be formed from a thin sheet metal component using stamping, laser cutting, etching, and/or machining techniques, for example. The teeth (93) are divided in two groups of four on opposite sides of the longitudinal axis and are displaced from each other longitudinally. The teeth (93) are displaced longitudinally to increase the surface area of interaction with the corresponding needle retention feature (712). While one tooth may provide a small amount of resistance to separation of the needle proximal end (50) from the needle retention feature (712), multiple (e.g., eight) teeth provide a significant amount of resistance. The height of the teeth (93) may be variable, for example the distal most teeth (93) may be configured to bite into the needle retention feature (712) at a first radial level, where the successive teeth (93) may be configured to bite into the needle retention feature (712) at increasing radial levels, thereby preserving the ability of the successive following teeth (93) to bite into the material of needle retention feature (712) as the needle proximal end (50) is driven into the needle retention feature (712).

The needle assembly proximal end (50) depicted in FIGS. 13A-13E is configured to couple to a needle retention feature (712) similar to the one depicted in FIGS. 12B-12D and described above. The needle retention feature (712) is a tubular member made of a thin walled plastic with a distal opening (701), as shown in FIGS. 13B-13E. The needle retention feature (712) also includes a funnel-shaped flange (702) disposed around the distal opening (701) to guide the most proximal end (84) of the needle spine assembly (76) into the distal opening (701). In addition, the needle retention feature (712) includes a proximally directed collar (703) formed around the inside of the distal opening (701). The collar (703) has a smooth inner diameter. The needle retention feature (712) is made of an elastically deformable material (e.g., a polymer) such that the distal opening (701) and the collar (703) can be enlarged/deformed to allow the most proximal end (84) to be inserted in a proximal direction. The collar (703) can also "ovalize" to secure and grip the tree shaped most proximal end (84).

When the needle assembly proximal end (50) is inserted into the needle retention feature (712), the teeth (93) are pointed away from direction of travel, thereby reducing insertion force. After the needle assembly proximal end (50) has been inserted into the needle retention feature (712), if the needle retention feature (712) is pulled (proximally) away from the needle assembly proximal end (50), the teeth (93) are pointed toward the direction of travel, thereby increasing the retraction force transmitted by the coupled needle assembly proximal end (50) and needle retention feature (712). The collar (703) deforms and "ovalizes" to retain the most proximal end (84). Further, one or both of the teeth (93) may scrape the inner diameter of the collar (703) to retain the most proximal end (84).

While the most proximal end (84) depicted in FIGS. 13A-13E has eight teeth (93), alternative embodiments have other teeth configurations. For instance, the most proximal end can have a fewer or more than eight teeth, and they can be arranged in any subgroups in any location on the most proximal end. Embodiments of safety injection systems including a needle assembly proximal end with teeth, have teeth that are directed to reduce insertion force and increase retraction force. The structure of the needle assembly proximal end with teeth and its corresponding needle retention feature therefore achieves the insertion force/retraction force differential/ratio required for the safe injection system.

E. Needle Assembly Proximal End Tip Geometry

Figure 14:
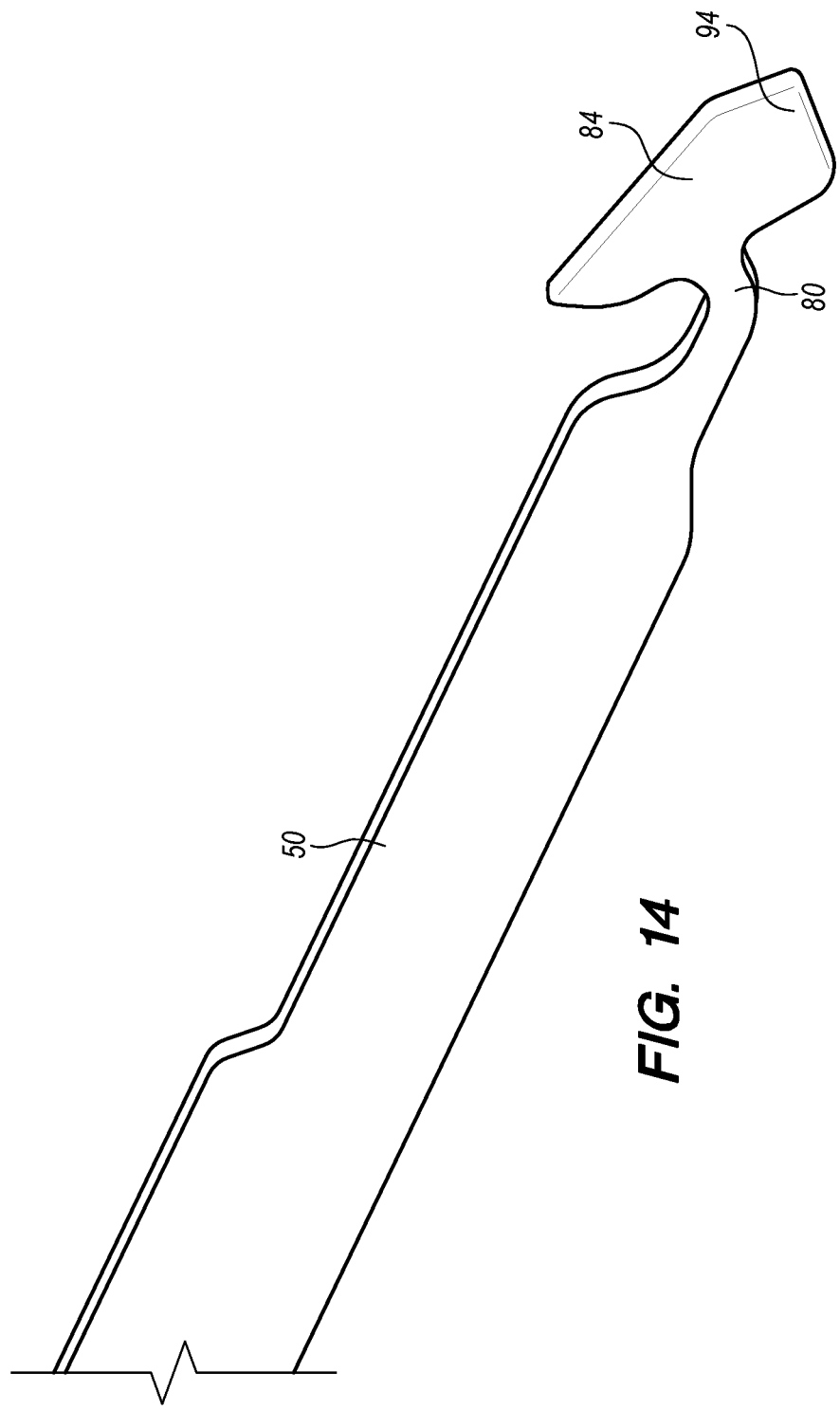

FIG. 14 depicts a most proximal end (84) of a needle assembly proximal end (50) that forms an approximate "T" shape that articulates about a pivot (80), like the one depicted in FIGS. 9A to 9I. The most proximal end (84) depicted in FIG. 14 forms a point (94) in the insertion configuration, but the edges forming the point (94) are not sharp. This is in contrast to an actual arrowhead, which has both a pointed end and sharp knife-like edges for penetration. This pointed, but not sharp geometry is configured to cooperate with a funnel-shaped flange in a needle retention feature to guide the most proximal end (84) into a needle retention feature without the most proximal end (84) penetrating and catching/snagging on the funnel-shaped flange. This pointed, but not sharp geometry can be used with any relatively flat most proximal end design, including those depicted in FIGS. 9A to 9I, 11A-11C, and 13A-13E.

Exemplary Dual-Chamber Safe Injection System

Figure 15:
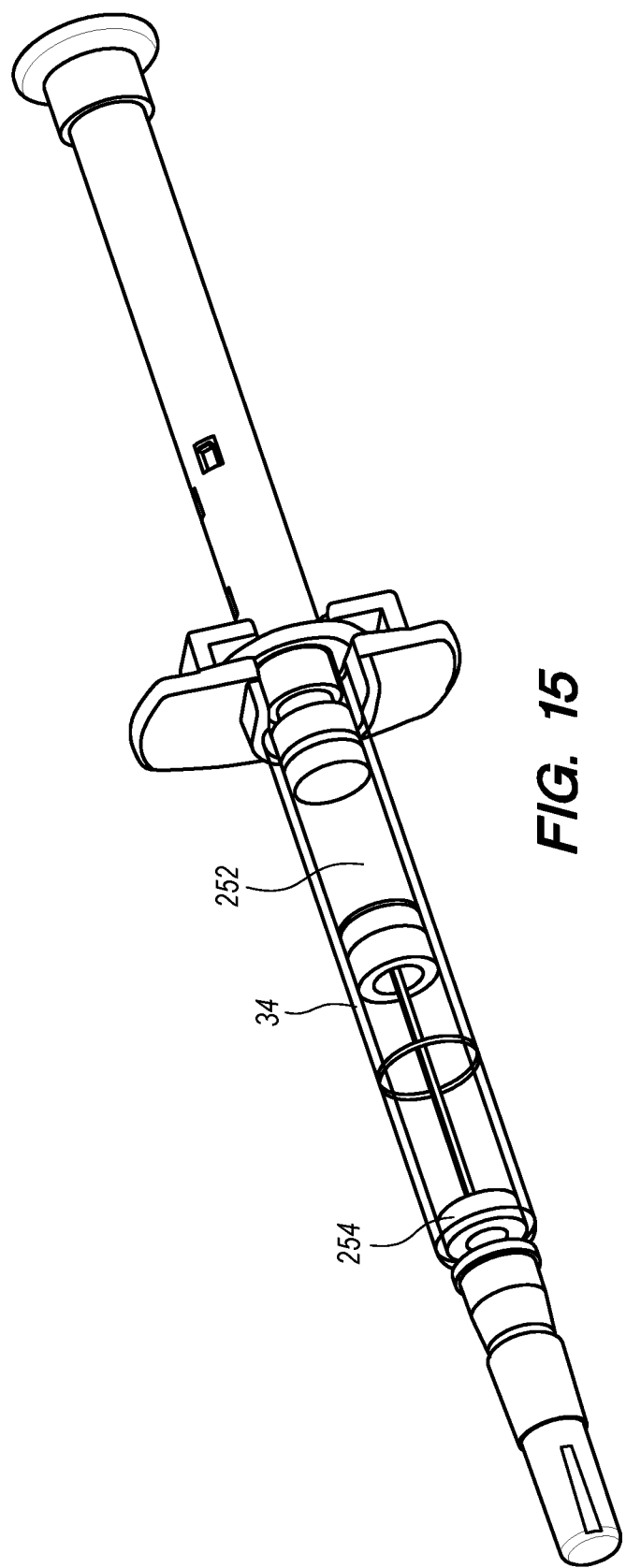
FIG. 15 illustrates a dual-chamber safe injection system according to one embodiment.

The needle assembly proximal ends (50), most proximal ends/harpoons (84), and needle retention features (712) described herein can also be used with dual-chamber safe injection systems. Referring to FIG. 15, various aspects of an embodiment designed to facilitate injection of multi-part medications are illustrated, wherein two or more medication components are combined to form an injection combination or solution shortly before delivery into the patient. In one embodiment, a liquid diluent (252) may be combined with a substantially non-liquid form (254), such as a powdered form, of a drug agent, such as a freeze-dried or lyophilized drug component, shortly before injection. The embodiment depicted in FIG. 15 is a dual-chamber configuration, wherein two chambers within the same syringe body (34) are utilized to carry, mix, and inject an injection solution. Examples of such dual-chamber safe injection systems are described in U.S. patent application Ser. No. 14/696,342, the contents of which have been incorporated herein by reference.

Exemplary Cartridge Safe Injection System

The needle assembly proximal ends (50), most proximal ends/harpoons (84), and needle retention features (712) described herein can also be used with cartridge safe injection systems. Referring to FIGS. 16A-16D, various aspects of an embodiment of a cartridge safe injection system are illustrated. FIG. 16A depicts a cartridge (71) that is assembled with a drug (252), a cartridge cap (72), a stopper (36) inside of the cartridge (71), and a finger flange (73). FIG. 16B depicts a needle hub (74) including a proximal cap (75) covering the needle assembly proximal end (50). FIG. 16C depicts the needle hub (74) with the proximal (75) removed. In this configuration, the needle assembly proximal end (50) can be inserted through the cartridge cap (72) and into the cartridge (71). FIG. 16D depicts a plunger rod (70) in a position relative to the cartridge (71) to be inserted into the finger flange (73) and screwed into the stopper (36).

Further depicted in FIG. 16D is a plunger rod removal brake (100) which is constructed of at least one externally projecting surface (102) that interlocks with a distally facing surface on the finger flange (104) to prevent removal of the plunger rod (70) after the injection has been performed. To minimize the length of the plunger rod (70), it may be desirable to retract the needle only behind the distal most end of the needle hub (74). In this case, the sharpened needle tip (48) is not retracted into the plunger rod (70) as the plunger rod (70) is too short to accommodate the whole needle length. The plunger rod (70) must be prevented from being removed from the syringe body (34) or cartridge (71) after the injection has been performed to prevent exposure of the needle tip (48).

Referring to FIGS. 16E-16G, a cross sectional view of the cartridge safe injection system is depicted. This embodiment of the cartridge based system includes a cap (72) which is constructed of a rubber cartridge seal (106) which is enclosed within a metal crimp (108). The cap (72) seals the medicine within the cartridge (71). The needle spine assembly (78) may be placed over the cap (72) and the needle proximal end (50) is penetrated through the cartridge seal (106). The penetration of the cartridge seal (106) may be performed at the factory prior to being shipped to the user, or may be performed at the point of use. A backup seal (110) may be disposed between the cartridge seal (106) and the needle coupling assembly (606) to take up assembly tolerances between the needle coupling assembly (606) and the cap (72). FIG. 16G depicts a cross sectional view of the cartridge (71) and cap (72) assembly prior to needle penetration. The embodiment of the cartridge safe injection system depicted in FIGS. 16A-16F is similar to the "pen" or "reusable" injection system depicted in FIGS. 8A-8U and described above. Examples of such cartridge safe injection systems are described in U.S. patent application Ser. No. 14/696,342, the contents of which have been incorporated herein by reference.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
   a syringe body defining a proximal opening and a distal needle interface;
   a plunger member defining a plunger interior and configured to be manually manipulated to insert a stopper member relative to the syringe body, the plunger member including
      a needle retention feature disposed in the plunger interior,
      an energy-storage member disposed in the plunger interior, and
      an energy-storage member latching member disposed in the plunger interior; and
   a needle hub assembly coupled to the distal needle interface of the syringe body, the needle hub assembly including
      a needle having a needle proximal end feature,
      a hub, and
      a needle latching member configured to couple the needle to the hub, wherein the needle is at least partially retractable into the plunger interior upon manipulation of the plunger member relative to the syringe body to transform the energy-storage member latching member from a latched state to an unlatched state, wherein the energy-storage member latching member is intercoupled between an interior surface of the plunger member and the needle retention feature;

wherein the needle proximal end feature is configured to deform from a first pre-insertion configuration to a second post-insertion configuration;

wherein the second post-insertion configuration has a larger axial profile relative to the first pre-insertion configuration, wherein the needle proximal end feature comprises an articulating hinge, wherein the needle retention feature comprises an opening sized to allow passage of the needle proximal end feature in the first pre-insertion configuration and to prevent passage of the needle proximal end feature in the second post-insertion configuration, and wherein the articulating hinge is configured to plastically deform the needle proximal end feature from the first pre-insertion configuration to the second post-insertion configuration.

2. The system of claim 1, wherein the needle proximal end feature and the needle retention feature are configured to selectively couple the needle to the needle retention feature.

3. The system of claim 1, wherein the articulating hinge is a living hinge.

4. The system of claim 1, wherein the needle proximal end feature comprises a longitudinal portion coupled to an articulating portion by the articulating hinge.

5. The system of claim 4, wherein the longitudinal portion has a longitudinal portion longitudinal axis that is closer to orthogonal to a longitudinal axis of the articulating portion in the second post-insertion configuration compared to the first pre-insertion configuration.

6. The system of claim 1, wherein the needle proximal end feature has a "T" shape.

7. The system of claim 1, wherein the needle proximal end feature has a flat cross-section.

8. The system of claim 1, wherein the needle retention feature comprises a funnel-shaped flange defining the opening and configured to guide the needle proximal feature into the opening.

9. The system of claim 1, wherein after a proximal end of the needle proximal end feature has been inserted through the opening into the needle retention feature, proximal movement of the needle retention feature moves the needle proximal end feature from the first pre-insertion configuration to the second post-insertion configuration.

10. The system of claim 1, wherein the articulating hinge is configured to elastically deform upon insertion of the articulating hinge into the needle retention feature.

* * * * *